United States Patent
Olson et al.

(10) Patent No.: US 10,231,788 B2
(45) Date of Patent: Mar. 19, 2019

(54) ROBOTIC CATHETER SYSTEM

(71) Applicant: St. Jude Medical, Atrial Fibrillation Division, Inc., St. Paul, MN (US)

(72) Inventors: Eric S. Olson, Maplewood, MN (US); John A. Hauck, Shoreview, MN (US); Nicholas A. Patronik, Minneapolis, MN (US); Mark B. Kirschenman, Waverly, MN (US); Cem M. Shaquer, Los Gatos, CA (US); Yusof Ganji, Milton (CA)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 508 days.

(21) Appl. No.: 14/878,183

(22) Filed: Oct. 8, 2015

(65) Prior Publication Data
US 2016/0106957 A1     Apr. 21, 2016

Related U.S. Application Data

(63) Continuation of application No. 12/751,843, filed on Mar. 31, 2010, now Pat. No. 9,161,817, which is a
(Continued)

(51) Int. Cl.
*A61B 34/20* (2016.01)
*A61M 25/01* (2006.01)
(Continued)

(52) U.S. Cl.
CPC .............. *A61B 34/20* (2016.02); *A61B 5/042* (2013.01); *A61B 34/30* (2016.02); *A61B 34/37* (2016.02);
(Continued)

(58) Field of Classification Search
CPC ..... A61B 8/12; A61B 319/2203; A61B 19/56; A61B 2034/301; A61B 34/20; A61B 34/30; G06T 17/05; Y10S 715/976
See application file for complete search history.

(56) References Cited

U.S. PATENT DOCUMENTS

| | | |
|---|---|---|
| 3,091,130 A | 5/1963 | Payerle et al. |
| 3,605,725 A | 9/1971 | Bentov |

(Continued)

FOREIGN PATENT DOCUMENTS

| | | |
|---|---|---|
| EP | 0151479 | 8/1985 |
| EP | 0904796 | 3/1999 |

(Continued)

OTHER PUBLICATIONS

Title: Supplemental European Search Report Citation: EP Application No. 11763450.1 Publication Date: Oct. 29, 2014 9 pages.
(Continued)

*Primary Examiner* — Nathan R Price
*Assistant Examiner* — Melissa A Snyder
(74) *Attorney, Agent, or Firm* — Dykema Gossett PLLC

(57) ABSTRACT

A robotic system for manipulating a catheter with a plurality of steering wires longitudinally situated within a length of the catheter includes a user interface configured to display a view of an anatomical model and to receive one or more user inputs; a catheter manipulator assembly configured to linearly actuate one or more control members of a catheter; and a robotic controller configured to provide a view of an anatomical model to the user interface; accept one or more user inputs from the user interface; register the one or more user inputs to a coordinate system associated with the anatomical model; compute one or more actuator commands from the one or more registered inputs; and cause the catheter manipulator assembly to linearly actuate one or more control members of a catheter in accordance with the computed actuator commands.

17 Claims, 79 Drawing Sheets

Related U.S. Application Data continuation-in-part of application No. 12/347,811, filed on Dec. 31, 2008, now Pat. No. 8,343,096.

(60) Provisional application No. 61/040,143, filed on Mar. 27, 2008, provisional application No. 61/099,904, filed on Sep. 24, 2008.

(51) Int. Cl.
| | | |
|---|---|---|
| *A61B 5/042* | (2006.01) | |
| *A61B 34/37* | (2016.01) | |
| *A61B 17/00* | (2006.01) | |
| *A61B 34/00* | (2016.01) | |
| *A61B 19/00* | (2006.01) | |
| *A61B 90/00* | (2016.01) | |
| *A61B 34/30* | (2016.01) | |
| *A61B 34/10* | (2016.01) | |

(52) U.S. Cl.
CPC .............. *A61B 34/71* (2016.02); *A61B 34/76* (2016.02); *A61B 34/77* (2016.02); *A61M 25/0147* (2013.01); *A61B 34/25* (2016.02); *A61B 2017/00026* (2013.01); *A61B 2017/00477* (2013.01); *A61B 2019/2211* (2013.01); *A61B 2019/2219* (2013.01); *A61B 2019/2242* (2013.01); *A61B 2034/107* (2016.02); *A61B 2034/301* (2016.02); *A61B 2034/305* (2016.02); *A61B 2034/741* (2016.02); *A61B 2034/742* (2016.02); *A61B 2090/064* (2016.02); *A61B 2090/372* (2016.02); *A61M 2205/33* (2013.01); *A61M 2205/505* (2013.01); *A61M 2210/125* (2013.01)

(56) References Cited

U.S. PATENT DOCUMENTS

| | | |
|---|---|---|
| 3,893,449 A | 7/1975 | Lee et al. |
| 4,160,508 A | 7/1979 | Frosch et al. |
| 4,348,556 A | 9/1982 | Gettig et al. |
| 4,393,728 A | 7/1983 | Larson et al. |
| 4,494,417 A | 1/1985 | Larson |
| 4,543,090 A | 9/1985 | McCoy |
| 4,758,222 A | 7/1988 | McCoy |
| 4,784,042 A | 11/1988 | Paynter |
| 4,802,487 A | 2/1989 | Martin et al. |
| 4,884,557 A | 12/1989 | Takehana |
| 4,962,448 A | 10/1990 | DeMaio |
| 4,974,151 A | 11/1990 | Advani et al. |
| 5,078,140 A | 1/1992 | Kwoh |
| 5,107,080 A | 4/1992 | Rosen |
| 5,170,817 A | 12/1992 | Sunderland |
| 5,238,005 A | 8/1993 | Imran |
| 5,298,930 A | 3/1994 | Asakura |
| 5,303,148 A | 4/1994 | Mattson et al. |
| 5,318,525 A | 6/1994 | West |
| 5,339,799 A | 8/1994 | Kami et al. |
| 5,396,266 A | 3/1995 | Brimhall et al. |
| 5,410,638 A | 4/1995 | Colgate et al. |
| 5,441,483 A | 8/1995 | Avitall |
| 5,449,345 A | 9/1995 | Taylor |
| 5,520,644 A | 5/1996 | Imran |
| 5,533,967 A | 7/1996 | Imran |
| 5,545,200 A | 8/1996 | West |
| 5,579,442 A | 11/1996 | Kimoto |
| 5,607,158 A | 3/1997 | Chan |
| 5,607,462 A | 3/1997 | Imran |
| 5,623,582 A | 4/1997 | Rosenberg |
| 5,630,783 A | 5/1997 | Steinberg |
| 5,661,253 A | 8/1997 | Aoki |
| 5,684,512 A | 11/1997 | Schoch et al. |
| 5,706,827 A | 1/1998 | Ehr |
| 5,755,577 A | 5/1998 | Gillio |
| 5,767,839 A | 6/1998 | Rosenberg |
| 5,784,542 A | 6/1998 | Ohm et al. |
| 5,791,908 A | 8/1998 | Gillio |
| 5,800,178 A | 9/1998 | Gillio |
| 5,805,140 A | 9/1998 | Rosenberg et al. |
| 5,807,377 A | 9/1998 | Madhani |
| 5,808,665 A | 9/1998 | Green |
| 5,828,813 A | 10/1998 | Ohm |
| 5,854,622 A | 12/1998 | Brannon |
| 5,861,024 A | 1/1999 | Rashidi |
| 5,876,325 A | 3/1999 | Mizuno et al. |
| 5,897,488 A | 4/1999 | Ueda |
| 5,907,487 A | 5/1999 | Rosenberg et al. |
| 5,913,820 A | 6/1999 | Bladen et al. |
| 5,917,898 A | 6/1999 | Bassa et al. |
| 6,007,550 A | 12/1999 | Wang et al. |
| 6,040,758 A | 3/2000 | Sedor |
| 6,063,095 A | 5/2000 | Wang |
| 6,096,004 A | 8/2000 | Meglan et al. |
| 6,113,395 A | 9/2000 | Hon |
| 6,201,196 B1 | 3/2001 | Wergen |
| 6,233,476 B1 | 5/2001 | Strommer et al. |
| 6,233,504 B1 | 5/2001 | Das et al. |
| 6,251,015 B1 | 6/2001 | Caprai |
| 6,290,683 B1 | 9/2001 | Erez |
| 6,348,911 B1 | 2/2002 | Rosenberg |
| 6,358,207 B1 | 3/2002 | Lathbury et al. |
| 6,385,509 B2 | 5/2002 | Das et al. |
| 6,396,232 B2 | 5/2002 | Haanpaa |
| 6,432,112 B2 | 8/2002 | Brock |
| 6,498,944 B1 | 12/2002 | Ben-Haim et al. |
| 6,500,167 B1 | 12/2002 | Webster |
| 6,522,141 B2 | 2/2003 | Debbins et al. |
| 6,540,685 B1 | 4/2003 | Rhoads et al. |
| 6,610,007 B2 | 8/2003 | Belson et al. |
| 6,663,559 B2 | 12/2003 | Hale et al. |
| 6,671,533 B2 | 12/2003 | Chen et al. |
| 6,681,880 B2 | 1/2004 | Bernhardt et al. |
| 6,709,667 B1 | 3/2004 | Lowe |
| 6,726,675 B1 | 4/2004 | Beyar |
| 6,770,027 B2 | 8/2004 | Banik et al. |
| 6,785,358 B2 | 8/2004 | Johnson |
| 6,850,252 B1 | 2/2005 | Hoffberg |
| 6,869,390 B2 | 3/2005 | Elliott |
| 6,869,396 B2 | 3/2005 | Belson |
| 6,968,223 B2 | 11/2005 | Hanover |
| 7,016,469 B2 | 3/2006 | Johnson et al. |
| 7,056,123 B2 | 6/2006 | Gregorio et al. |
| 7,193,521 B2 | 3/2007 | Moberg |
| 7,197,354 B2 | 3/2007 | Sobe |
| 7,199,790 B2 | 4/2007 | Rosenberg |
| 7,247,139 B2 | 7/2007 | Yudkovitch et al. |
| 7,259,906 B1 | 8/2007 | Islam |
| 7,263,397 B2 | 8/2007 | Hauck |
| 7,276,044 B2 | 10/2007 | Ferry |
| 7,308,831 B2 | 12/2007 | Cunningham et al. |
| 7,356,448 B2 | 4/2008 | Schaeffer |
| 7,386,339 B2 | 6/2008 | Strommer et al. |
| 7,455,288 B2 | 12/2008 | Dudney et al. |
| 7,672,849 B2 | 3/2010 | Yudkovitch et al. |
| 7,698,966 B2 | 4/2010 | Gosselin |
| 7,742,803 B2 | 6/2010 | Viswanathan et al. |
| 7,850,642 B2 | 12/2010 | Moll |
| 7,880,717 B2 | 2/2011 | Berkley et al. |
| 7,945,546 B2 | 5/2011 | Bliss et al. |
| 7,955,316 B2 | 6/2011 | Weitzner et al. |
| 7,963,288 B2 | 6/2011 | Rosenberg et al. |
| 8,164,573 B2 | 4/2012 | DaCosta et al. |
| 8,317,744 B2 | 11/2012 | Kirschenman |
| 8,317,745 B2 | 11/2012 | Kirschenman |
| 8,332,072 B1 | 12/2012 | Schaible et al. |
| 8,390,438 B2 | 3/2013 | Olson |
| 8,416,203 B2 | 4/2013 | Tsui |
| 8,560,118 B2 | 10/2013 | Greer et al. |
| 8,926,511 B2 | 1/2015 | Bar-Tar |
| 2001/0018591 A1 | 8/2001 | Brock |
| 2001/0025183 A1 | 9/2001 | Shahidi |
| 2002/0004423 A1 | 1/2002 | Minami et al. |

(56) References Cited

U.S. PATENT DOCUMENTS

| | | |
|---|---|---|
| 2002/0065485 A1 | 5/2002 | DuBois et al. |
| 2002/0068868 A1 | 6/2002 | Thompson et al. |
| 2002/0072704 A1 | 6/2002 | Mansouri-Ruiz |
| 2002/0087048 A1 | 7/2002 | Brock |
| 2002/0184055 A1 | 12/2002 | Naghavi et al. |
| 2003/0018232 A1 | 1/2003 | Elliott |
| 2003/0050733 A1 | 3/2003 | Wang et al. |
| 2003/0114962 A1 | 6/2003 | Niemeyer |
| 2003/0121382 A1 | 7/2003 | Morson |
| 2003/0176948 A1 | 9/2003 | Green |
| 2004/0050247 A1 | 3/2004 | Topping |
| 2004/0068173 A1 | 4/2004 | Viswanathan |
| 2004/0133189 A1 | 7/2004 | Sakurai |
| 2004/0138530 A1 | 7/2004 | Kawai et al. |
| 2004/0145563 A9 | 7/2004 | Rosenberg et al. |
| 2004/0146388 A1 | 7/2004 | Khajepour et al. |
| 2004/0193239 A1 | 9/2004 | Falwell et al. |
| 2004/0223636 A1 | 11/2004 | Edic |
| 2004/0243147 A1 | 12/2004 | Lipow |
| 2004/0247267 A1 | 12/2004 | Gilboa |
| 2005/0004515 A1 | 1/2005 | Hart et al. |
| 2005/0024331 A1 | 2/2005 | Berkley et al. |
| 2005/0038333 A1 | 2/2005 | Sra |
| 2005/0059960 A1 | 3/2005 | Simaan et al. |
| 2005/0075538 A1 | 4/2005 | Banik |
| 2005/0172405 A1 | 8/2005 | Menkedick et al. |
| 2005/0197623 A1 | 9/2005 | Leeflang et al. |
| 2005/0203382 A1 | 9/2005 | Govari |
| 2005/0222554 A1 | 10/2005 | Wallace |
| 2005/0234293 A1 | 10/2005 | Yamamoto et al. |
| 2005/0234320 A1 | 10/2005 | Balasubramanian |
| 2006/0052664 A1 | 3/2006 | Julian |
| 2006/0089637 A1 | 4/2006 | Werneth et al. |
| 2006/0095022 A1 | 5/2006 | Moll et al. |
| 2006/0137476 A1 | 6/2006 | Bull |
| 2006/0155321 A1 | 7/2006 | Bressler et al. |
| 2006/0276775 A1* | 12/2006 | Rosenberg ....... A61B 17/00234 606/1 |
| 2006/0293643 A1 | 12/2006 | Wallace et al. |
| 2007/0016008 A1 | 1/2007 | Schoenefeld |
| 2007/0022384 A1 | 1/2007 | Abbott et al. |
| 2007/0043338 A1 | 2/2007 | Moll et al. |
| 2007/0060833 A1 | 3/2007 | Hauck |
| 2007/0073137 A1 | 3/2007 | Schoenefeld |
| 2007/0100254 A1 | 5/2007 | Murakami et al. |
| 2007/0120512 A1 | 5/2007 | Albu-Schaffer et al. |
| 2007/0135803 A1 | 6/2007 | Belson |
| 2007/0142726 A1 | 6/2007 | Carney |
| 2007/0161857 A1 | 7/2007 | Durant et al. |
| 2007/0172803 A1 | 7/2007 | Hannaford et al. |
| 2007/0185404 A1 | 8/2007 | Hauck et al. |
| 2007/0185485 A1 | 8/2007 | Hauck |
| 2007/0185486 A1 | 8/2007 | Hauck |
| 2007/0197896 A1 | 8/2007 | Moll et al. |
| 2007/0197939 A1 | 8/2007 | Wallace |
| 2007/0198008 A1 | 8/2007 | Hauck et al. |
| 2007/0233044 A1 | 10/2007 | Wallace |
| 2007/0233045 A1 | 10/2007 | Weitzner |
| 2007/0257821 A1 | 11/2007 | Son et al. |
| 2007/0268269 A1 | 11/2007 | Chang et al. |
| 2007/0270650 A1 | 11/2007 | Eno et al. |
| 2007/0270685 A1 | 11/2007 | Kang |
| 2007/0276214 A1 | 11/2007 | Dachille |
| 2007/0298877 A1 | 12/2007 | Rosenberg et al. |
| 2008/0009791 A1 | 1/2008 | Cohen et al. |
| 2008/0013809 A1 | 1/2008 | Zhu |
| 2008/0112842 A1 | 5/2008 | Edwards |
| 2008/0201847 A1 | 8/2008 | Menkedick |
| 2008/0297490 A1 | 12/2008 | Adkins |
| 2008/0312536 A1 | 12/2008 | Dala-Krishna |
| 2009/0012533 A1 | 1/2009 | Barbagli |
| 2009/0033623 A1 | 2/2009 | Lin |
| 2009/0061928 A1 | 3/2009 | Lee et al. |
| 2009/0123111 A1 | 5/2009 | Udd |
| 2009/0137952 A1 | 5/2009 | Ramamurthy et al. |
| 2009/0177454 A1 | 7/2009 | Bronstein |
| 2009/0192519 A1 | 7/2009 | Omori et al. |
| 2009/0195514 A1 | 8/2009 | Glynn et al. |
| 2009/0247993 A1 | 10/2009 | Kirschenman et al. |
| 2009/0264156 A1 | 10/2009 | Burghardt et al. |
| 2009/0322697 A1 | 12/2009 | Cao |
| 2009/0327886 A1 | 12/2009 | Whytock |
| 2010/0066676 A1 | 3/2010 | Kramer et al. |
| 2010/0073150 A1 | 3/2010 | Olson et al. |
| 2010/0079386 A1 | 4/2010 | Scott et al. |
| 2010/0082039 A1 | 4/2010 | Mohr et al. |
| 2010/0103127 A1 | 4/2010 | Park et al. |
| 2010/0256558 A1 | 10/2010 | Olson et al. |
| 2010/0268067 A1 | 10/2010 | Razzaque et al. |
| 2010/0314031 A1 | 12/2010 | Heideman et al. |
| 2011/0040547 A1 | 2/2011 | Gerber et al. |
| 2011/0128555 A1 | 6/2011 | Rotschild et al. |
| 2011/0137156 A1 | 6/2011 | Razzaque et al. |
| 2011/0152882 A1 | 6/2011 | Wenderow et al. |
| 2011/0289441 A1 | 11/2011 | Venon et al. |
| 2011/0306986 A1 | 12/2011 | Lee et al. |
| 2012/0071891 A1 | 3/2012 | Itkowitz et al. |
| 2012/0133601 A1 | 5/2012 | Marshall et al. |
| 2012/0158011 A1* | 6/2012 | Sandhu .................. A61B 34/30 606/130 |
| 2012/0277663 A1 | 11/2012 | Millman et al. |
| 2013/0006268 A1 | 1/2013 | Swarup et al. |
| 2013/0154913 A1 | 6/2013 | Genc et al. |
| 2013/0165854 A1 | 6/2013 | Sandhu et al. |
| 2013/0166484 A1* | 6/2013 | Hartmann ................ G06N 3/08 706/16 |
| 2013/0176220 A1 | 7/2013 | Merschon et al. |
| 2013/0179162 A1 | 7/2013 | Merschon et al. |

FOREIGN PATENT DOCUMENTS

| | | |
|---|---|---|
| GB | 2211280 | 6/1989 |
| GB | 2397177 | 7/2007 |
| JP | S60221280 | 11/1985 |
| JP | H06344285 | 12/1994 |
| JP | H8-280709 | 10/1996 |
| JP | H10216238 | 8/1998 |
| JP | 2003024336 | 1/2003 |
| JP | 2007-325936 | 12/2007 |
| WO | 9320535 | 10/1993 |
| WO | 1996/039944 | 12/1996 |
| WO | 9639944 | 12/1996 |
| WO | 03/024336 A1 | 3/2003 |
| WO | 2003049596 | 6/2003 |
| WO | 2006/120666 | 11/2006 |
| WO | 2007056590 | 5/2007 |
| WO | 2007/088208 | 8/2007 |
| WO | 2007/098494 | 8/2007 |
| WO | 2007/120329 | 10/2007 |
| WO | 2007136803 | 11/2007 |
| WO | 2007/146325 | 12/2007 |
| WO | 2007143859 | 12/2007 |
| WO | 2008045831 | 4/2008 |
| WO | 2008101228 | 8/2008 |
| WO | 2008103212 | 8/2008 |
| WO | 2009/120982 | 10/2009 |
| WO | 2009/120992 | 10/2009 |
| WO | 2009120940 | 10/2009 |
| WO | 2009120992 | 10/2009 |
| WO | 2010025338 | 3/2010 |
| WO | 2010059179 | 5/2010 |
| WO | 2010068783 | 6/2010 |
| WO | 2010107916 | 9/2010 |

OTHER PUBLICATIONS

Title: International Search Report Citation: PCT Application No. PCT/US2011/030656 Publication Date: Jun. 13, 2011 8 pages.
Title: Emotiv—Brain Computer Interface Technology (online) Citation: <URL: http://www.emotiv.com> Publication Date: Aug. 11, 2011 3 pages.
Title: Supplemental European Search Report Citation: EP Application No. 09726364.4 Publication Date: Jan. 22, 2013 7 pages.

(56) References Cited

OTHER PUBLICATIONS

Title: Supplemental European Search Report Citation: EP Application No. 09723739.0 Publication Date: Jul. 10, 2012 6 pages.
Title: Supplemental European Search Report Citation: EP Application No. 09724550.0 Publication Date: Jul. 10, 2012 6 pages.
Title: International Search Report Citation: PCT Application No. PCT/US2009/058121 Publication Date: Nov. 19, 2009 2 pages.
Title: International Search Report Citation: PCT Application No. PCT/US2009/038536 Publication Date: May 28, 2009 2 pages.
Title: International Search Report Citation: PCT Application No. PCT/US2009/038534 Publication Date: May 27, 2009 2 pages.
Supplementary European Search Report for EP Application No. 11763410.5, dated Jun. 10, 2015. 7 pages.
Title: International Search Report Citation: PCT Application No. PCT/US2009/038597 Publication Date: May 18, 2009 2 pages.
Title: International Search Report Citation: PCT Application No. PCT/US2009/038618 Publication Date: May 22, 2009 2 pages.
International Search Report for PCT Application No. PCT/US2009/069712, dated Feb. 25, 2010 10 pgs.
Supplementary European Search Report for EP Application No. 09725131.8, dated Feb. 20, 2013. 7 pgs.
Title: International Search Report Citation: PCT Application No. PCT/US2009/038525 Publication Date: May 27, 2009 2 pages.
Title: International Search Report Citation: PCT Application No. PCT/US2009/038531 Publication Date: May 19, 2009 3 pages.
Title: International Search Report Citation: PCT Application No. PCT/US2009/038533 Publication Date: Jun. 17, 2009 2 pages.
Title: The Aurora Electromagnetic Tracking System, Aurora Electromagnetic Measurement System—3D Tracking for Medical Guidance Citation: Northern Digital, Inc. <URL: http://www.ndigital.com/medical/aurora.pho?act=print> Publication Date: (actual publication date unknown) 3 pages.
Title: Apple Wins Strategic Multitouch and Music Tempo Workout Patents Citation: Patently Apple <URL: http://www.patentlyapple.com/patently-apple/2010/04/apple-wins-strategic-multitouch-music-tempo-workout-patents.html> Publication Date: (actual publication date unknown) 5 pages.
Polaris Family of Optical Tracking Systems, Polaris Vicra & Spectra—Optical Measurement Systems for Medical Citation: Northern Digital Inc. <URL: http://www.ndigital.com/medical/polarisfamily.php?act=print> Publication Date: (actual publication date unknown) 5 pages.
Author: LaBelle, Kathryn Title: Evaluation of Kinect Joint Tracking for Clinical and In-Home Stroke Rehabilitation Tools Citation: <http://netscale.cse.nd.edu/twiki/pub/Edu/KinectRehabilitation/Eval_of_Kinect_for_Rehab.pdf> Publication Date: Dec. 2011 67 pages.
Author: Padoy, Nicolas Title: Needle Insertion Revisted (tele-surgery in depth), (online) Citation: The John Hopkins University <URL: http://www.youtube.com/watch?v=YsY_A0kLh-g> Publication Date: Jan. 2011 25 pages.
Title: Emotiv EPOC Software Development Kit—EPOC neuroheadset (online) Citation: <URL: http://www.emotiv.com/store/hardware/epoc/bci/epoc-neuroheadseU> Publication Date: (actual publication date unknown) 2 pages.
Title: Wii Remote—Wikipedia, the free encyclopedia (online) Citation: <URL: http://en.wikipedia.org/wiki/Wii_Remote> Publication Date: (actual publication date unknown) 17 pages.
Title: About the Kinect for Windows SDK—Microsoft Research (online) Citation: <URL: http://research.microsoft.com/en-us/um/redmond/projects/kinectsdk/about.aspx> Publication Date: (actual publication date unknown) 2 pages.
Title: Kinect—Wikipedia, the free encyclopedia (online) Citation: <URL: http://en.wikipedia.org/wiki/Kinect> Publication Date: (actual publication date unknown) 15 pages.
Title: International Search Report & Written Opinion Citation: PCT/US2012/031008 Publication Date: Jul. 20, 2012 10 pages.
Title: International Search Report and Written Opinion Citation : PCT/US2011/030764 Publication Date: Aug. 15, 2011 8 pages.
Ghobadi, et al. "Real Time Hand Based Robot Control Using Multimodal Images", IAENG International Journal of Computer Sciences, 35:4, IJCS_35_4_08; Nov. 20, 2008. 6 pgs.
Robot.pdf (Robot—Definition Robot at Dictionary.com, Oct. 27, 2015, http://dictionary.reference.com/browse/robot, pp. 1-5).

\* cited by examiner

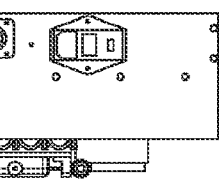
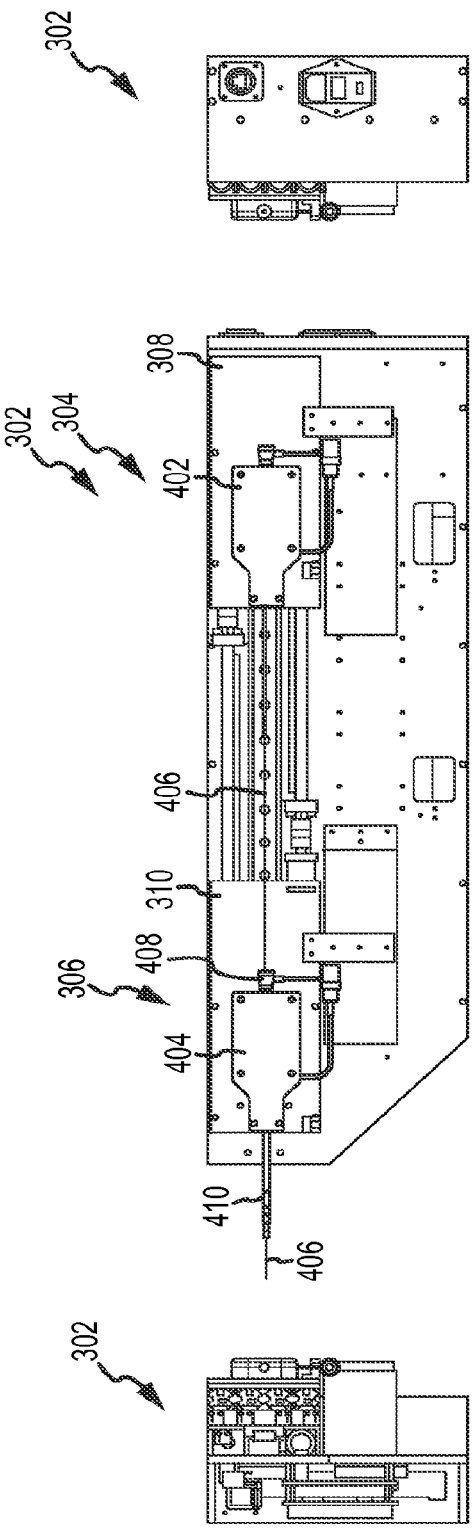
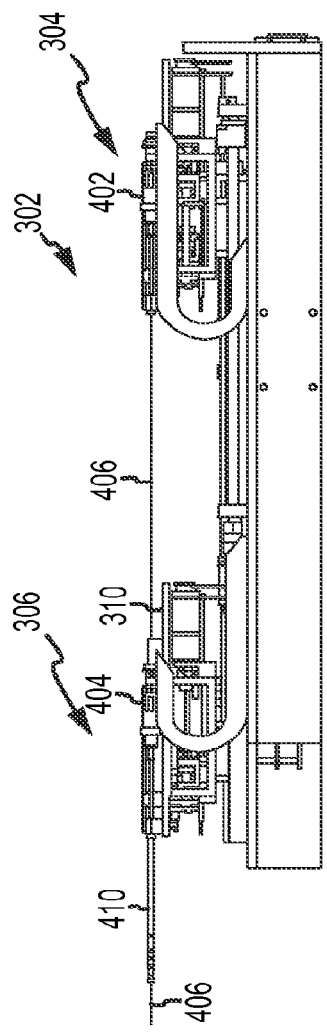

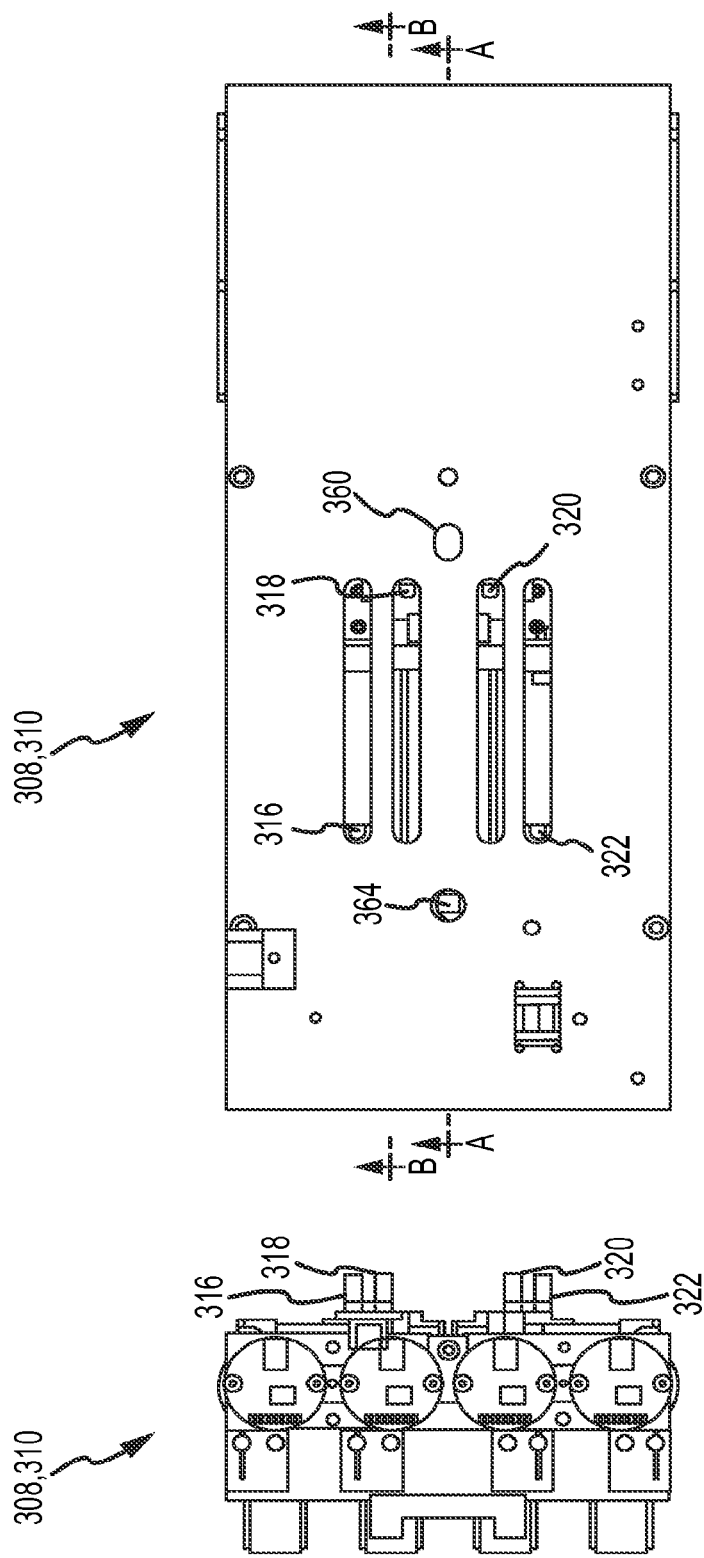

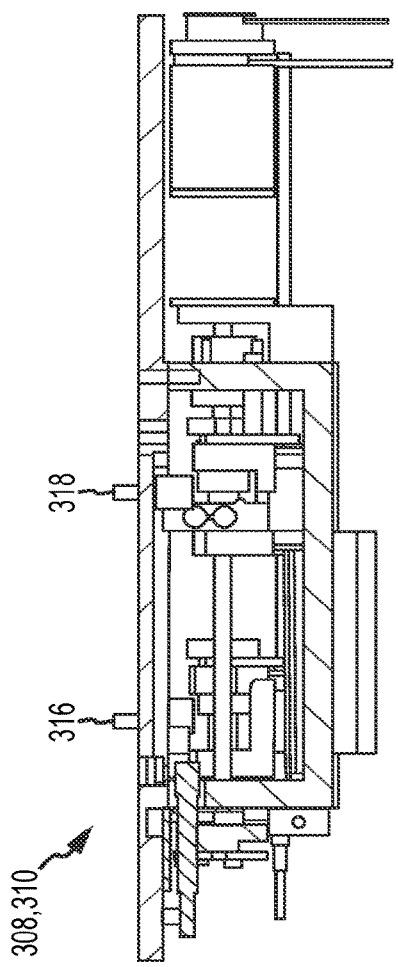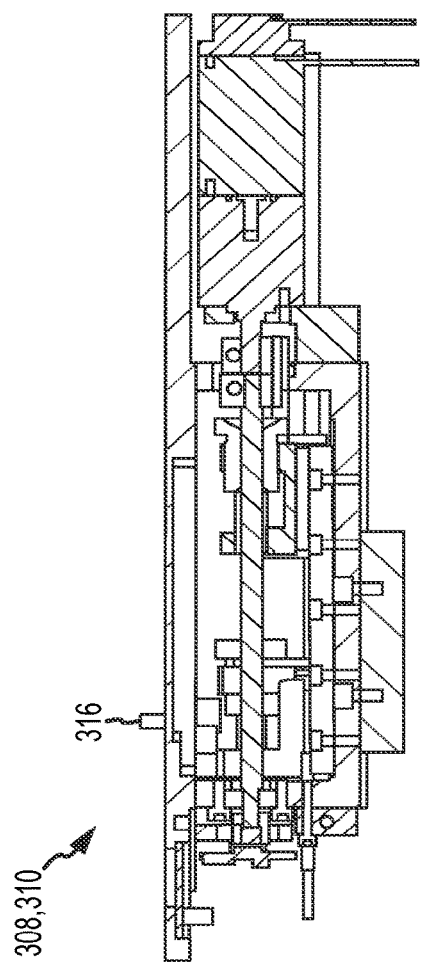
FIG.4f
FIG.4g

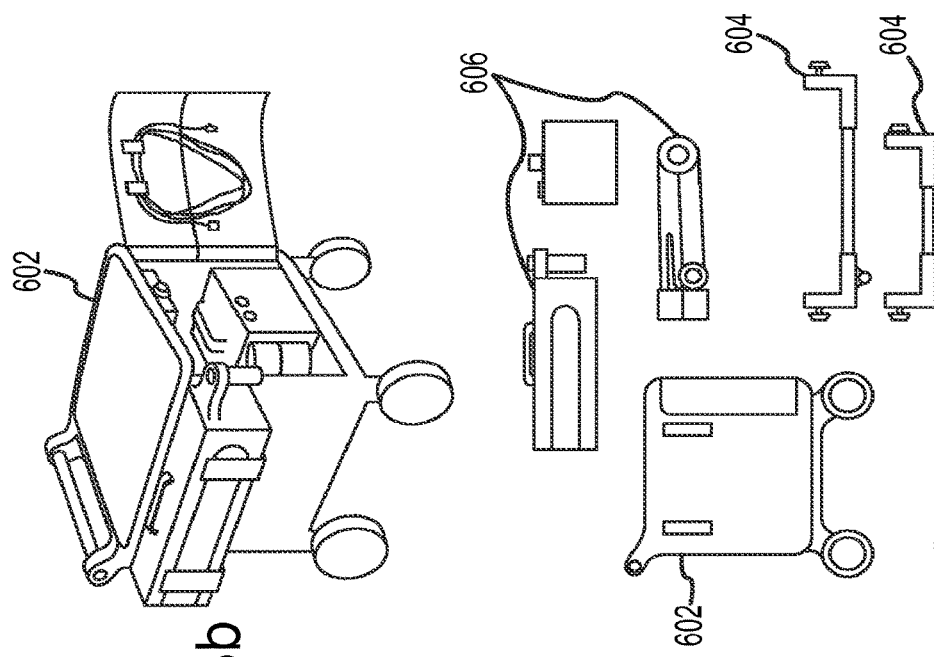
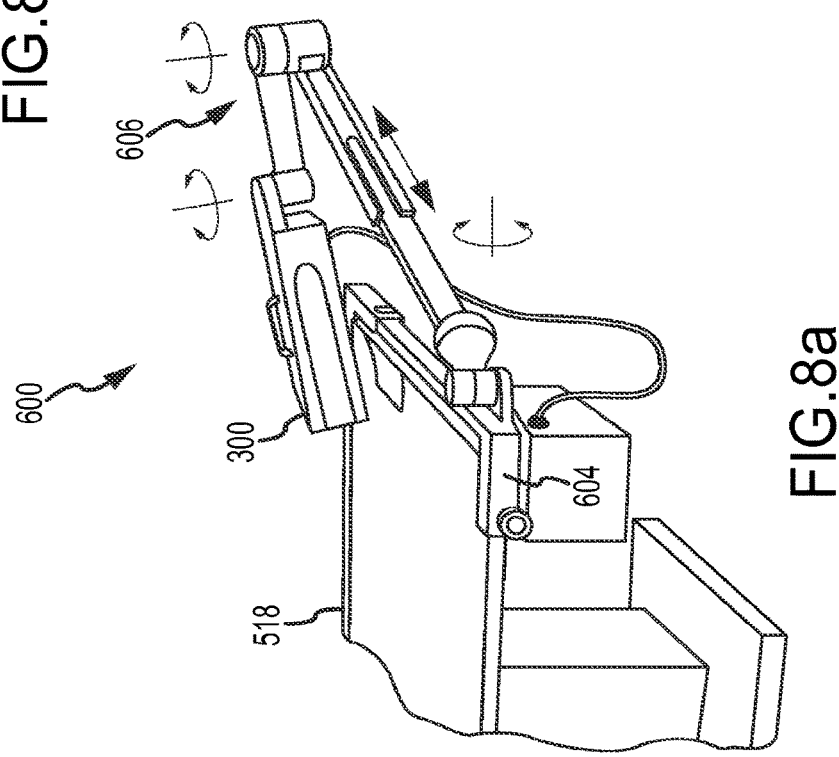
FIG.8b
FIG.8c
FIG.8a

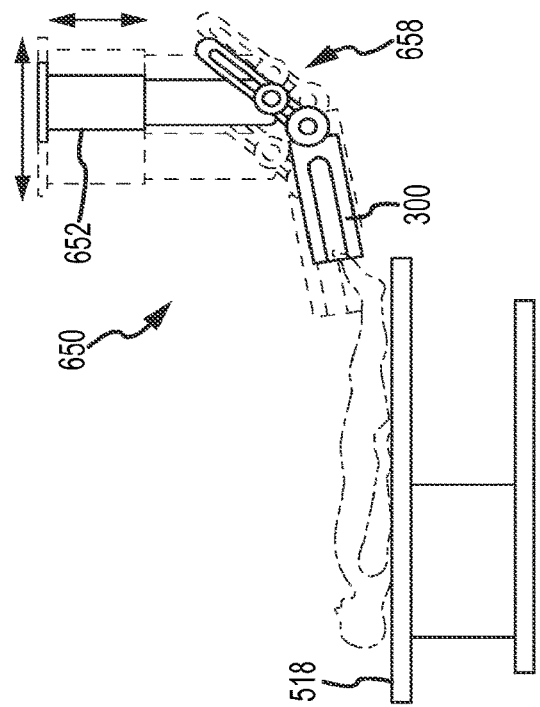
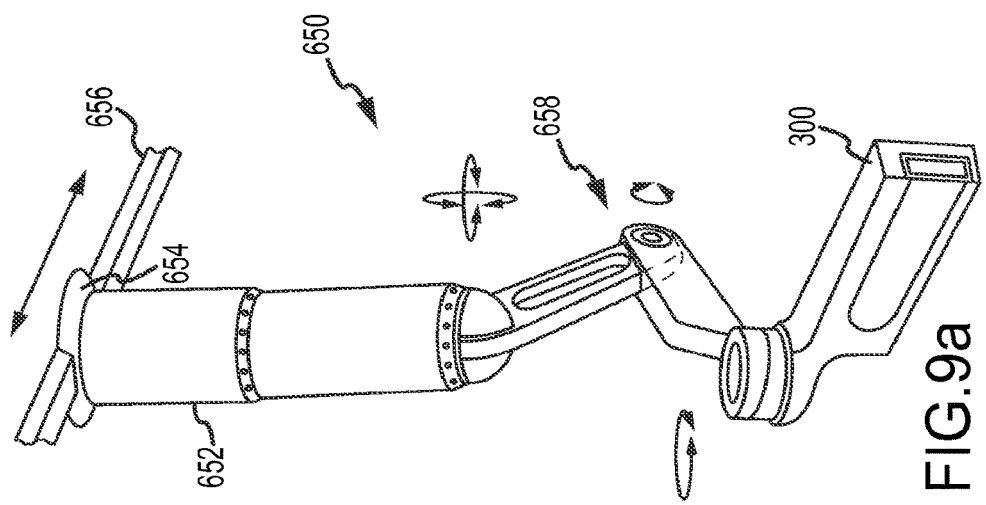

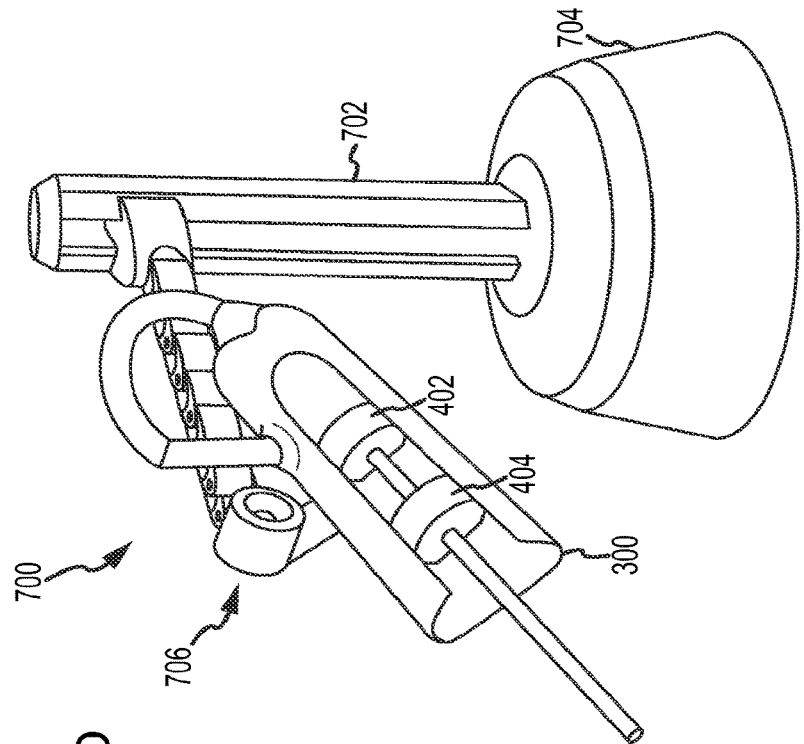
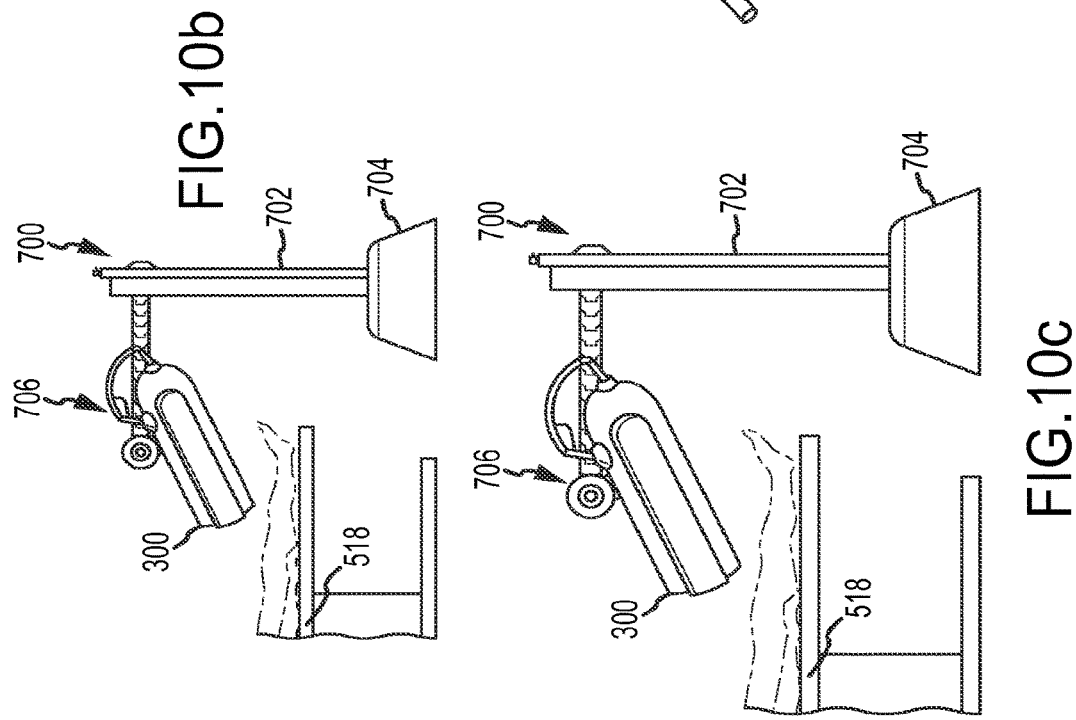

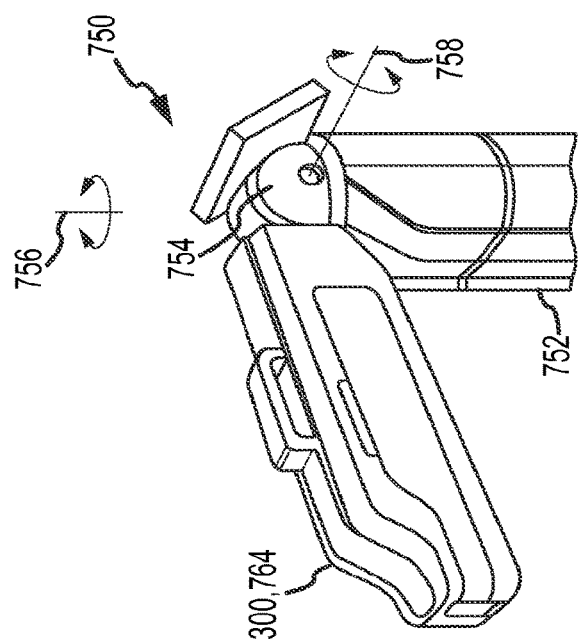
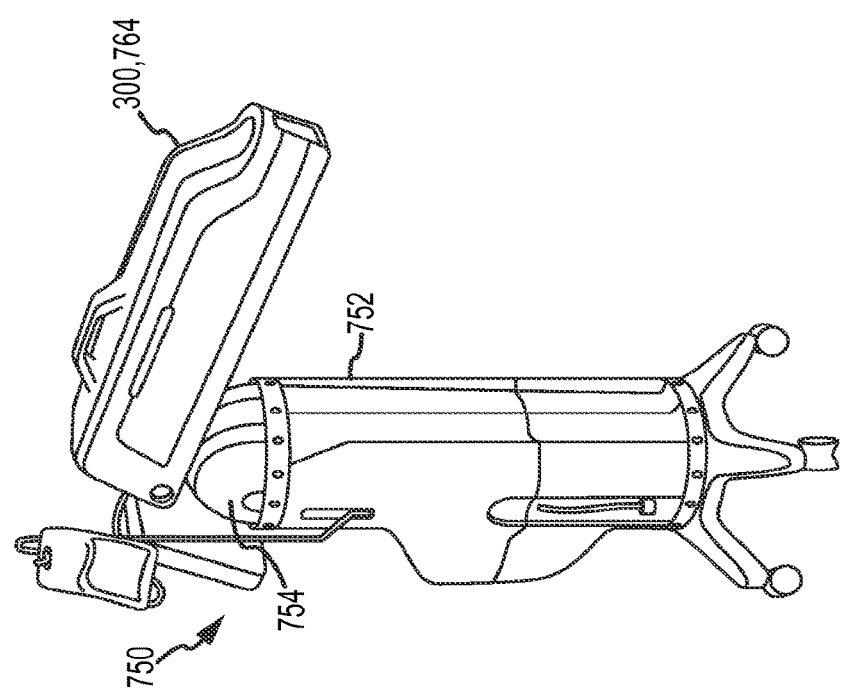
FIG. 11b
FIG. 11a

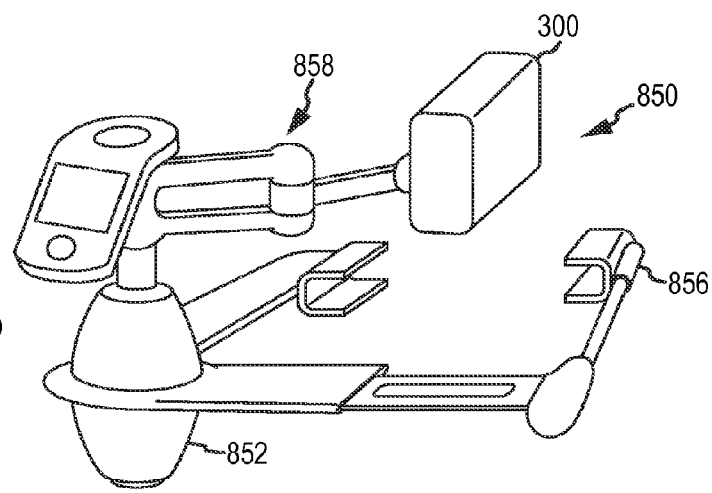
FIG.13b
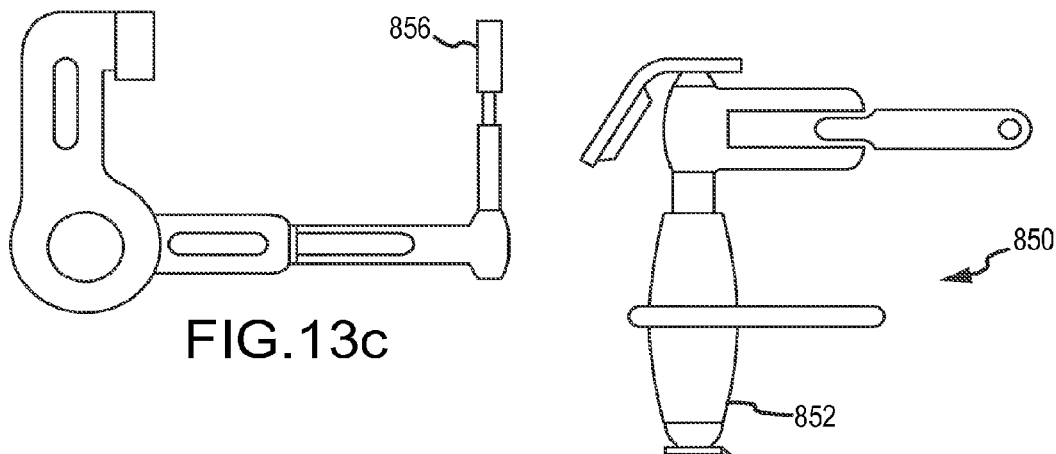
FIG.13c
FIG.13a

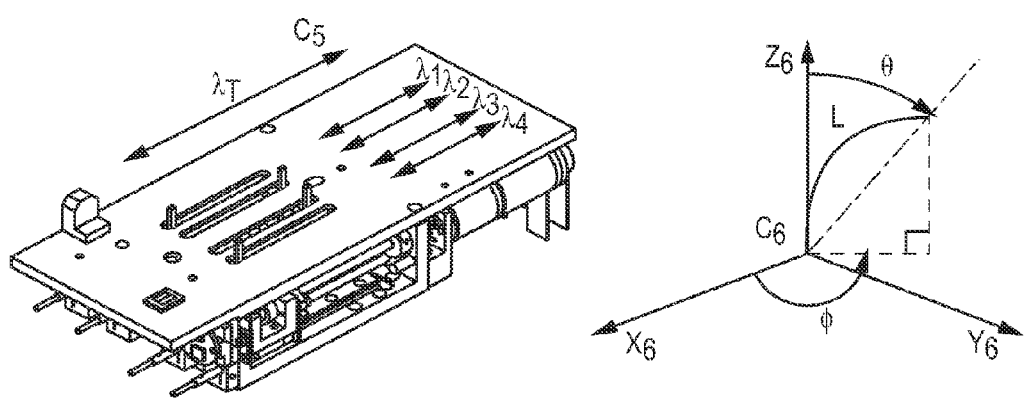
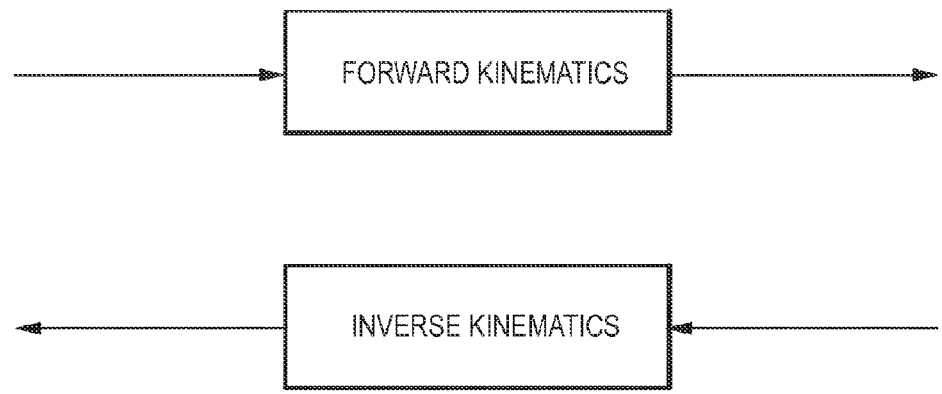
FIG.34

ROBOTIC CATHETER SYSTEM

CROSS REFERENCE TO RELATED APPLICATIONS

This application relates to and is a continuation of and claims the benefit of and priority to U.S. patent application Ser. No. 12/751,843 filed 31 Mar. 2010 which is a continuation-in-part of and claims the benefit of and priority to U.S. patent application Ser. No. 12/347,811 filed 31 Dec. 2008 (the '811 application), which in turn claims the benefit of and priority to U.S. provisional patent application Nos. 61/040,143 filed 27 Mar. 2008 (the '143 application) and 61/099,904 filed 24 Sep. 2008 (the '904 application), the entire disclosure of each of the '811 application, the '143 application, and the '904 application are hereby incorporated by reference as though fully set forth herein.

BACKGROUND OF THE INVENTION a. Field of the Invention

This invention relates to a robotic catheter system and method for automated control of a catheter and related components. In particular, the instant invention relates to a robotic catheter system for manipulating a catheter and related components, for example, for diagnostic, therapeutic, mapping and ablative procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

The inventors herein have thus recognized a need for a system and method for precise and dynamic automated control of a catheter and its related components, for example, for diagnostic, therapeutic, mapping and ablative procedures, that will minimize and/or eliminate procedural variability due to a user's skill level. The inventors herein have also recognized a need for a system and method for performing user-specified procedures at the patient site or from a remote location.

BRIEF SUMMARY OF THE INVENTION

A robotic system for manipulating a catheter with a plurality of steering wires longitudinally within a length of the catheter includes a user interface configured to display a view of an anatomical model and to receive one or more user inputs; a catheter manipulator assembly configured to linearly actuate one or more control members of a catheter, and a robotic controller configured to provide a view of an anatomical model to the user interface; accept one or more user inputs from the user interface; register the one or more user inputs to a coordinate system associated with the anatomical model; compute one or more actuator commands from the one or more registered inputs; and cause the catheter manipulator assembly to linearly actuate one or more control members of a catheter in accordance with the computed actuator commands. In an embodiment, the actuator commands may be computed, for example, by calculating an inverse Jacobian Matrix In an embodiment, the robotic system may additionally include a positioning system configured to provide an indication of a position of the catheter to the controller. The user interface may include an input device and a display device, and in an embodiment, may be a multi-touch display interface that can receive one or more touch-based inputs from a user. The display may include selectable on-screen menu buttons to activate functions such as pan, rotate, zoom, direct catheter movement, or may place lesion markers, waypoints, virtual sensors, automated movement targets, or draw movement lines.

In an embodiment, the input device may include a detectable glove or stylus that can be located in three dimensional space using a magnetic field, electrostatic field, optical positioning system, or the like. Alternatively, the input device may be designed similar to a traditional catheter handle.

BRIEF DESCRIPTION OF THE DRAWINGS

FIGS. 3d-3i are respectively enlarged left side, right side, top, front, back and a corresponding left side view of a first embodiment of a robotic catheter manipulator assembly.

FIGS. 4d-4g are respectively enlarged top and right side, and respectively sections A-A and B-B taken generally along lines A-A and B-B in FIG. 4d, of a first embodiment of a manipulation base;

FIGS. 8a-8c are isometric and related diagrammatic views of a third embodiment of a robotic catheter manipulator support structure, and various components thereof;

FIGS. 9a and 9b are isometric and related diagrammatic views of a fourth embodiment of a robotic catheter manipulator support structure;

FIGS. 10a-10c are isometric and related diagrammatic views of a fifth embodiment of a robotic catheter manipulator support structure;

FIGS. 11a-11h are isometric and related diagrammatic views of a sixth embodiment of a robotic catheter manipulator support structure, and various components thereof;

FIG. 34 is an illustration of forward and inverse kinematic relationships;

DETAILED DESCRIPTION OF EMBODIMENTS OF THE INVENTION

Figure 1:
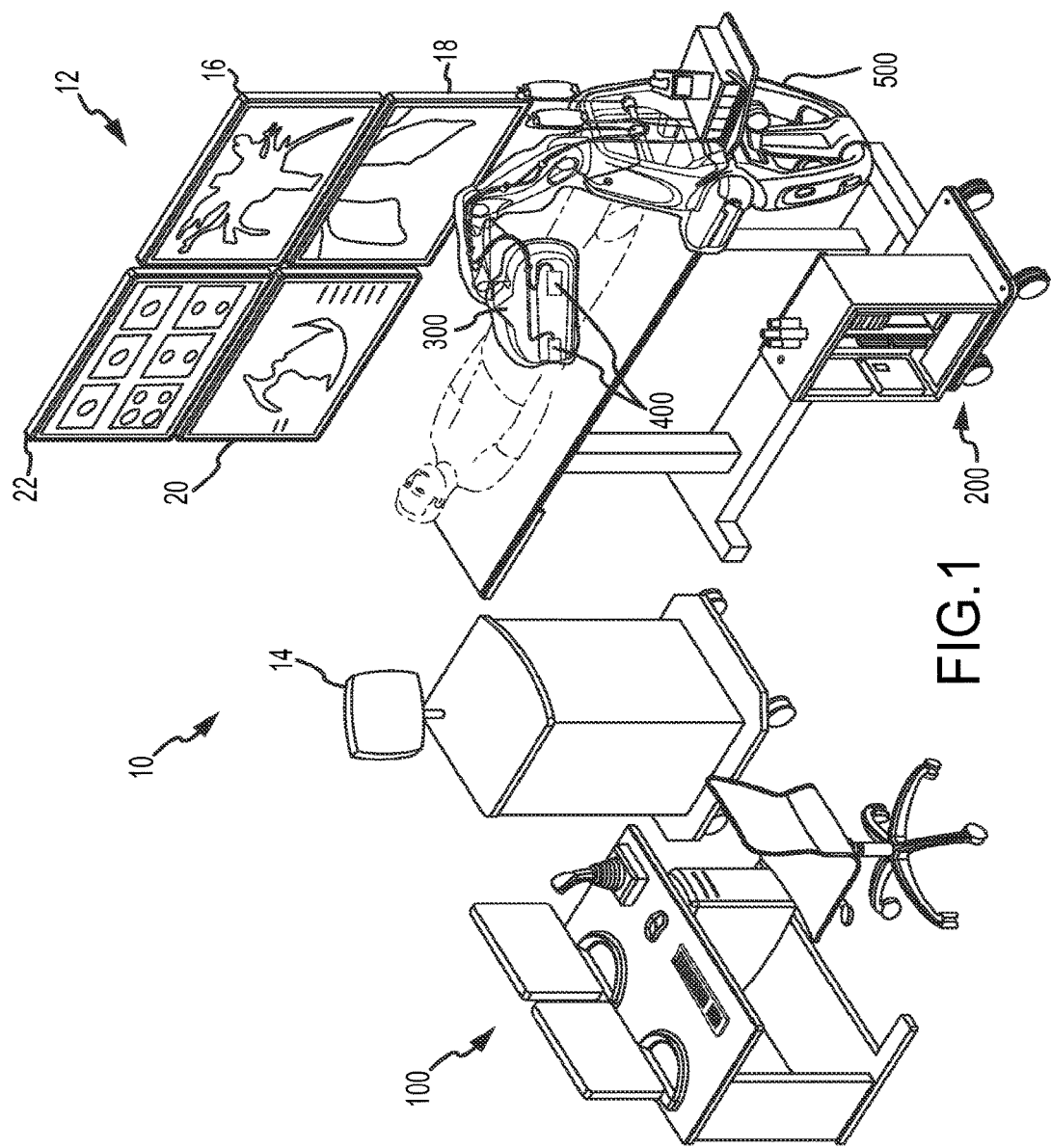
FIG. 1 is an isometric diagrammatic view of a robotic catheter system, illustrating an exemplary layout of various system components.

Referring now to the drawings wherein like reference numerals are used to identify identical components in the various views, an embodiment of robotic catheter system 10 (described in detail below), also referred to as "the system," may be likened to power steering for a catheter system. The system may be used, for example, to manipulate the location and orientation of catheters and sheaths in a heart chamber or in another body cavity. As shown in FIG. 1 and described in detail below, robotic catheter system 10 may generally incorporate a human input device and control system (referred to as "input control system") 100, e.g., a joystick and related controls, that a user such as an electrophysiologist (EP) may interact with, an electronic control system 200 that translates motions of the user at the input device into a resulting movement of a catheter tip, and a visualization system 12 that provides a user with real-time or near-real-time positioning information concerning the catheter tip. The system may further include closed-loop feedback using an EnSite NavX system 14, or similar positioning systems such as, for example, the gMPS system, commercially available from Mediguide Ltd., a robotic catheter manipulator assembly 300 for operating a robotic catheter device cartridge 400 and manipulator support structure 500 (described in detail below). The system provides the user with a similar type of control provided by a conventional manual system, but allows for repeatable, precise, and dynamic movements. The respective disclosures of the above-identified and other commonly owned and copending applications discussed in this application are incorporated herein by reference.

An embodiment of robotic catheter system 10 may involve automated catheter movement. A user, such as an EP, could identify locations (potentially forming a path) on a rendered computer model of the cardiac anatomy. The system can be configured to relate those digitally selected points to positions within a patient's actual/physical anatomy, and may command and control the movement of a catheter to defined positions. Once in position, either the user or system could then perform the desired treatment or therapy—which may further be in accordance with a defined algorithm. This system could enable full robotic control by using optimized path planning routines together with closed-loop position control. Furthermore, the system could automate certain "best-practices," such as pulling the catheter across the surface, or making contact at an oblique angle.

Referring to FIG. 1, input control system 100 will be described briefly.

The input control system 100 may generally allow a user to control the movement and advancement of both the catheter and sheath. Generally, several types of input devices may be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. The input device may be configured to directly control the movement of the catheter and sheath, or may be configured to, for example, manipulate a target or cursor on an associated display. In embodiments, for example and without limitation, the joystick may be spring centering so that any movement from the center position causes an incremental movement of the actual catheter tip, or the joystick may work in absolute terms. Haptic feedback may also be incorporated to provide a user with a sense of when contact has been made.

Referring to FIG. 1, electronic control system 200 will be described briefly.

Many additional features may be included with embodiments of the system to, for example, improve the accuracy or effectiveness of the system. Such features may include, closed-loop feedback using an EnSite NavX system or gMPS system 14 for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

Referring to FIG. 1, visualization system 12 will be described briefly.

Visualization system 12 may provide a user with real-time or near-real-time positioning information concerning the catheter tip. In an exemplary embodiment, system 12 may include an EnSite NavX monitor 16 or other similar monitor for displaying cardiac chamber geometries or models, displaying activation timing and voltage data to identify arrhythmias, and for facilitating guidance of catheter movement. A fluoroscopy monitor 18 may be provided for displaying a real-time x-ray image or for assisting a physician with catheter movement. Additional exemplary displays may include an ICE and EP Pruka displays, 20, 22, respectively.

Referring to FIG. 1, EnSite NavX system 14 will be described briefly.

EnSite NavX system 14 (described in detail in U.S. Pat. No. 7,263,397, titled "Method and Apparatus for Catheter Navigation and Location and Mapping in the Heart," incorporated by reference in its entirety) may be provided for creating realistic cardiac chamber geometries or models, displaying activation timing and voltage data to identify arrhythmias, and guiding precise catheter movement. EnSite NavX system 14 may collect electrical position data from catheters and use this information to track or navigate their movement and construct three-dimensional (3-D) models of the chamber.

In an embodiment, position data from the catheter may be obtained using a gMPS system, commercially available from Mediguide Ltd., and generally shown and described in U.S. Pat. No. 7,386,339 entitled "Medical Imaging and Navigation System," which is incorporated herein by reference in its entirety.

Referring to FIGS. 1-6c, robotic catheter manipulator assembly 300 for operating robotic catheter device cartridges 400 will be described briefly.

As generally shown in FIGS. 1-6c, robotic catheter system 10 may include one or more robotic catheter manipulator assemblies 300 that serve as the mechanical control for the movements or actions of one or more robotic catheter device cartridges 400. FIG. 1 illustrates a generally vertically oriented manipulator assembly 300 for minimizing approach angle; FIG. 2a illustrates a manipulator assembly 380 slightly angled from a generally horizontal position; and FIG. 2d illustrates an embodiment where multiple manipulator assemblies can be used for a single procedure. FIGS. 3a and 6a-6c respectively illustrate first-fourth embodiments of assemblies 300, namely assemblies 302, 370, 372 and 374. Manipulator assembly 302 and its associated components will be described herein for facilitating an understanding of robotic catheter system 10.

Referring to FIGS. 1 and 3a-5e, the catheter and sheath configuration of robotic catheter manipulator assembly 300 and robotic catheter device cartridges 400 will be described in detail.

As generally shown in FIGS. 1 and 3a-5e and discussed in greater detail below, the first embodiment of manipulator assembly 302 may respectively include both catheter and sheath manipulator mechanisms 304, 306. In this arrangement, the catheter and sheath manipulator mechanisms 304, 306 may be aligned such that the catheter can pass through the sheath in a coaxial arrangement. Each mechanism 304, 306 may be further capable of independent advancement/retraction (shown generally as directions $D_1$ and $D_2$) and independent four-wire steering control (e.g., eight total steering wires, comprising four sheath control wires and four catheter control wires), as discussed in detail below. It should also be understood that, while both the catheter and sheath may be capable of independent control, in alternative embodiments the system may only provide for control of one device while allowing the other device to remain passive (e.g., the sheath is actively controlled while the catheter is passive or "along for the ride"). In a configuration where one passive device is used, it may not be necessary to include control wires in the passive device.

With a configuration of robotic catheter system 10, such as shown in FIGS. 1 and 3a-5e, there will be relative travel of a first embodiment of catheter and sheath cartridges 402, 404 and relative movement associated with a portion of a catheter 406 between the two cartridges 402, 404. For many embodiments, there may be a water-tight fit of a proximal sheath opening 408, which can sometimes create resistance to catheter advancement. In order to help eliminate/reduce the potential issue of columnar buckling of catheter 406, a length of stiff material, such as, for example, a solid metal rod or fiber reinforced composite, may be incorporated on the interior of the proximal portion of catheter 406. Such a material may locally increase the catheter's bending stiffness and provide enhanced buckling support. Thus catheter 406 may be proximally stiffened so that the length of the catheter proximally extending from sheath cartridge 404 is less likely to buckle during relative translation, as the entire length of catheter 406 extends into sheath 410.

Referring to FIGS. 1 and 3a-5e, the first embodiment of robotic catheter manipulator assembly 302 will be described in detail.

Figure 3A:
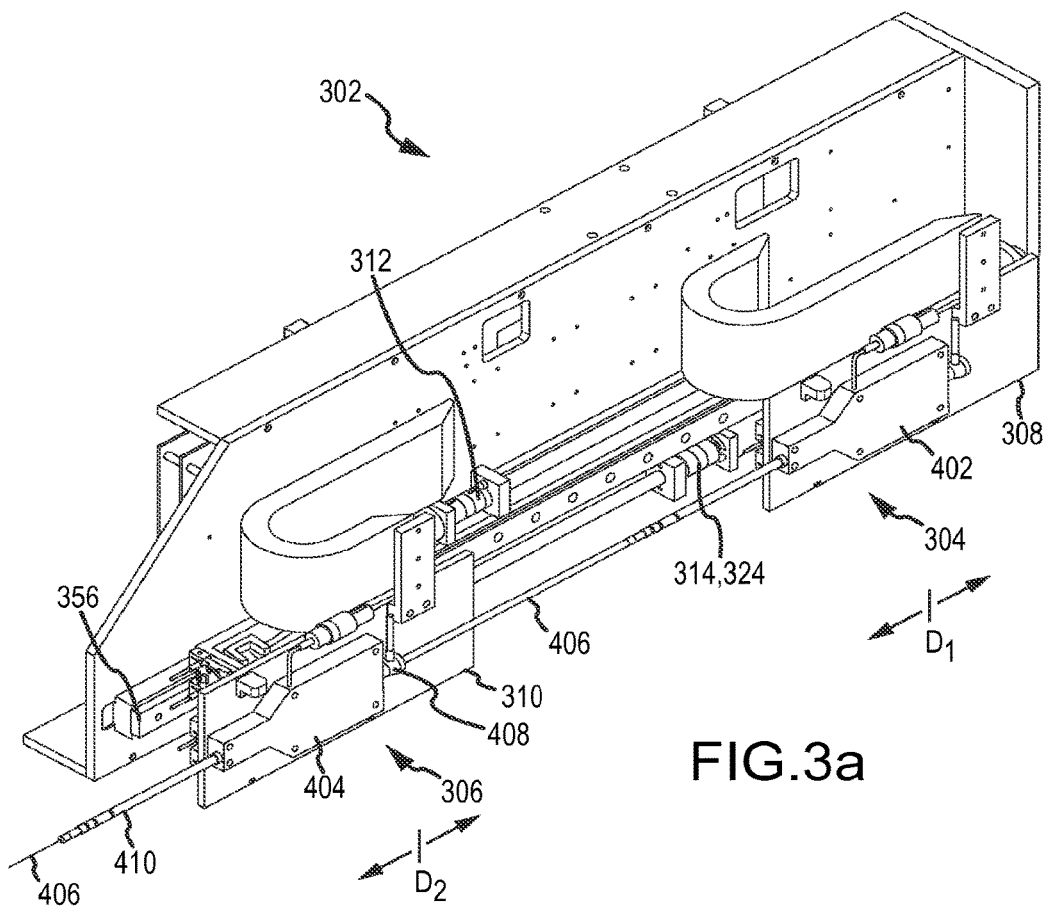
FIGS. 3a-3c are enlarged isometric.
Figure 3B:
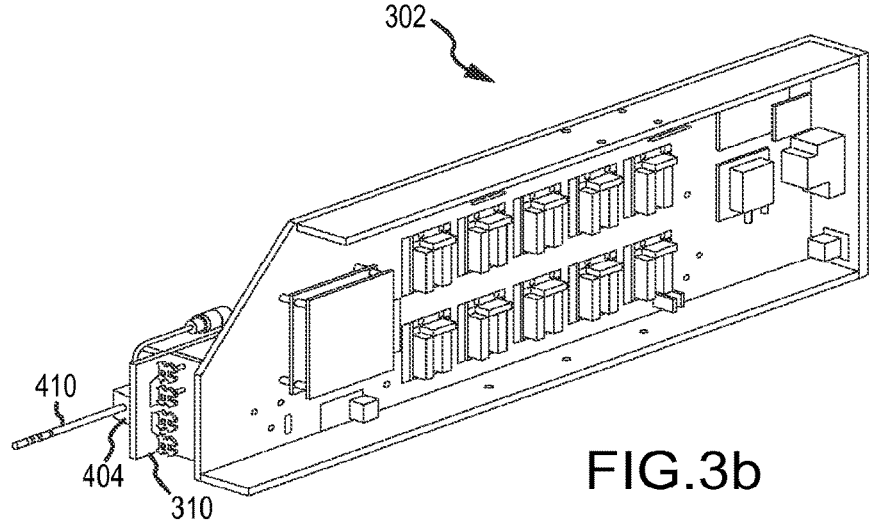
Figure 3C:
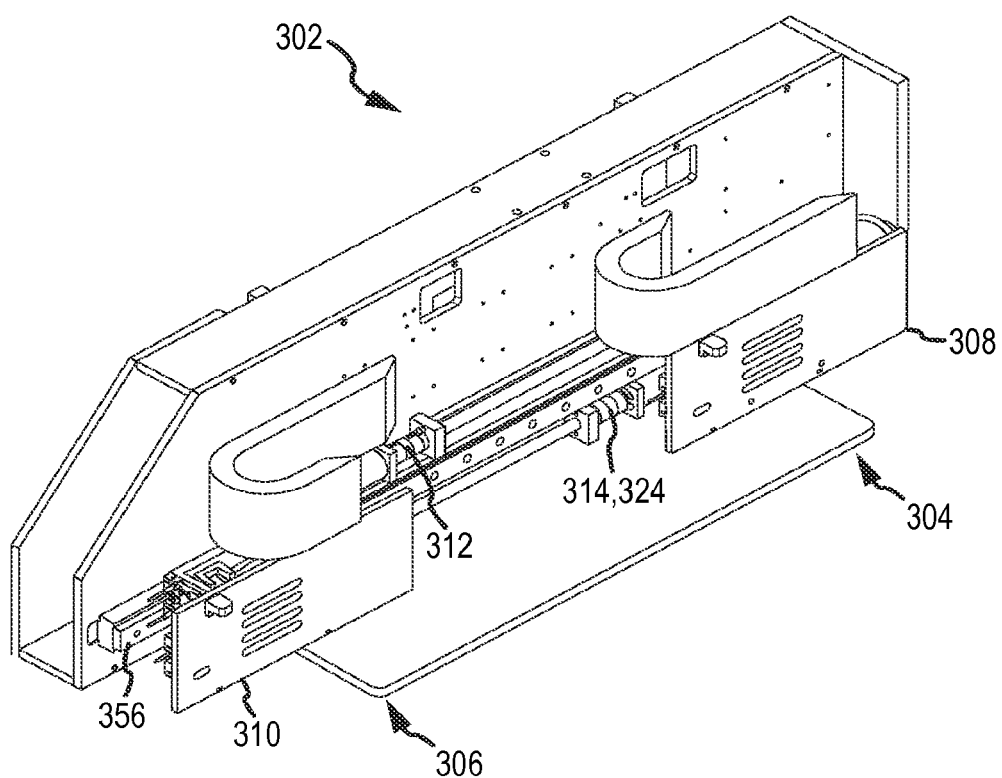
Figure 3H:
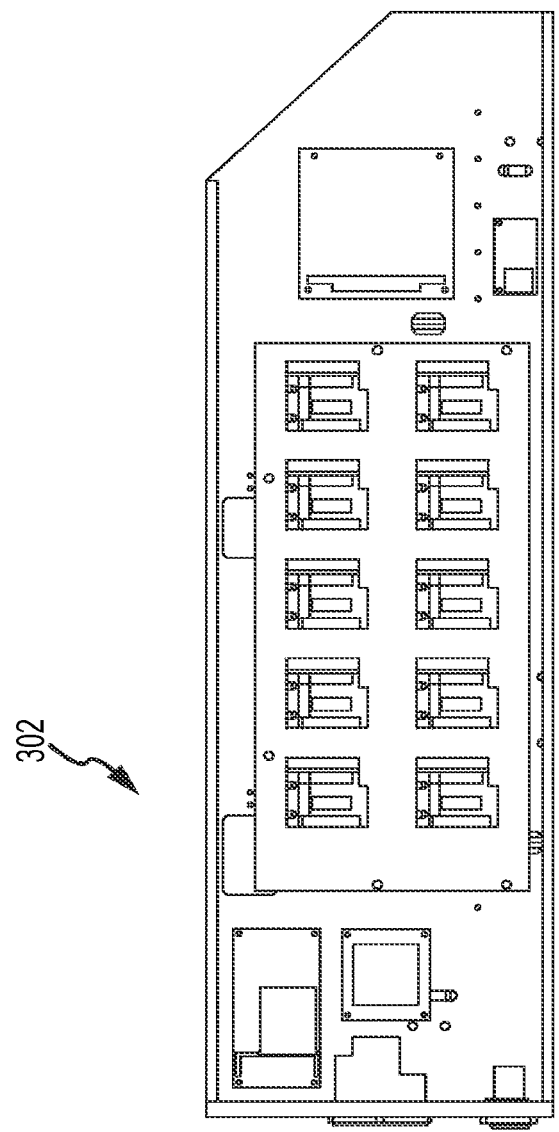
Figure 3I:
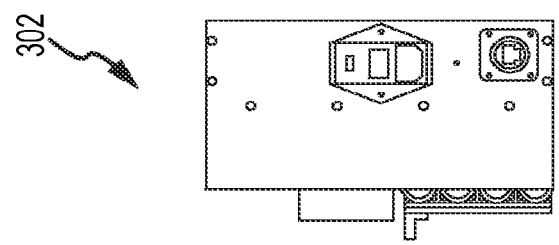

As generally shown in FIGS. 1 and 3a-5e, robotic catheter system 10 which includes one or more robotic catheter manipulator assemblies 300, includes the first embodiment of robotic catheter manipulator assembly 302 including both catheter and sheath manipulation mechanisms 304, 306 for manipulating, for example, catheter and sheath cartridges 402, 404. Manipulator assembly 302 may include interconnected/interlocking manipulation bases 308, 310 for catheter and sheath cartridges 402, 404, and likewise may include electrical "handshake" functionality as discussed below. Each interlocking base 308, 310 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 3a, each interlocking base may be translated by high precision drive mechanisms 312, 314. Such drive mechanisms may include, for example and without limitation, a motor driven lead screw or ball screw.

Figure 4A:
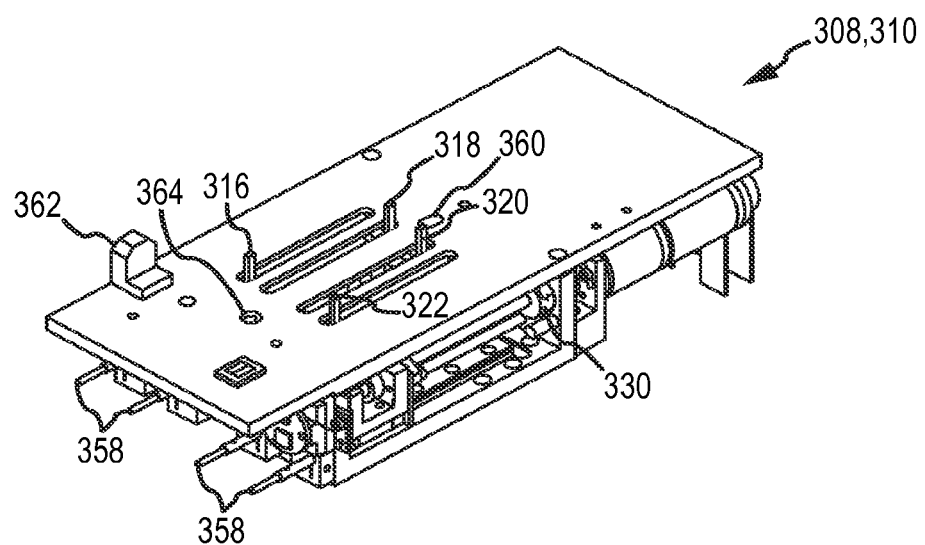
FIGS. 4a-4c are enlarged isometric views.
Figure 4B:
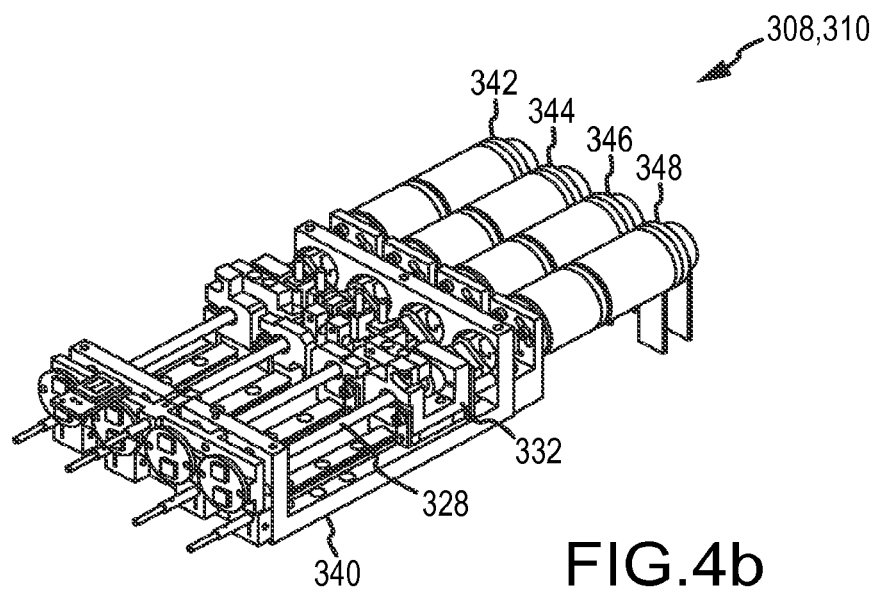
Figure 4C:
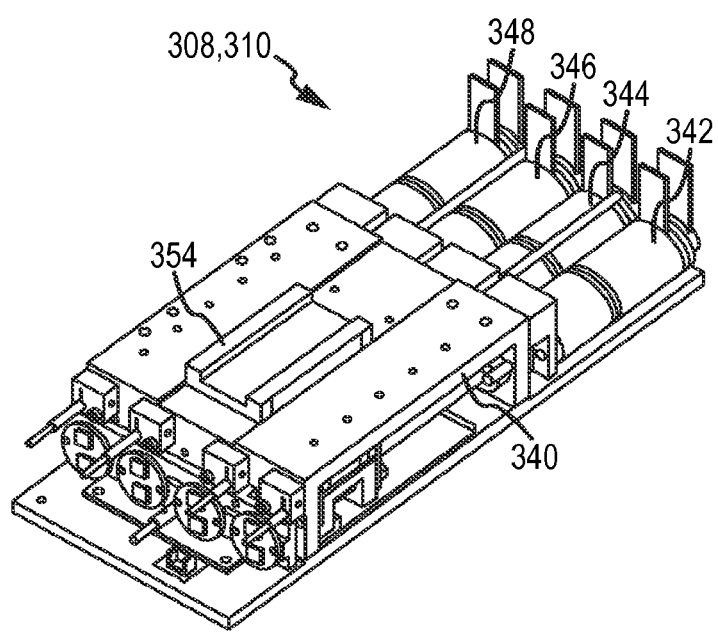

As shown in FIGS. 3a-3i and 4a-4g, for each cartridge 402, 404, an associated manipulation base 308, 310 may include a plurality of fingers 316, 318, 320 and 322, (e.g., one per steering wire) that extend or protrude upwardly to contact and interact with the steering wire slider blocks (such as slider blocks 412, 414, 416, 418) to independently tension select steering wires 420, 422, 424, 426. Each finger can be configured to be independently actuated by a precision drive mechanism, such as a motor driven ball screw 324, and may be outfitted with steering wire force sensors to measure corresponding steering wire tension. Each motor driven ball screw (for both finger control and cartridge translation control) may further include encoders to measure a relative and/or an absolute position of each element of the system. As shown in FIG. 4a, bearing 332 and coupler 330 of ball screw 324 may engage frame 340 of respective bases 308, 310 and a corresponding finger 316, 318, 320 or 322 may be mounted adjacent a strain gauge for measuring the corresponding steering wire tension.

Referring to FIGS. 4a-4g, bases 308, 310 may include exemplary components such as motors 342, 344, 346 and 348, respectively coupled to fingers 316, 318, 320 and 322. A bearing 354 may be provided for sliding of bases 308, 310 on track 356. A plurality of inductive sensors (e.g. home sensors) 358 may be provided for guiding each manipulation base to a safe position.

Manipulator assembly 302 may be disposed in a vertical configuration (see FIG. 1) for minimizing both the approach angle of the catheter and the distance the catheter must extend from the patient, or slightly angled from a generally horizontal position (see FIG. 2). In the vertical configuration of FIG. 1, the approach angle and catheter extension distance may be minimized by vertically orienting the backplane of the manipulator head, with the interlocking cartridges positioned at the lower extreme such that they may travel nearly horizontally and substantially in line with the point of entry into the patient (e.g., as generally illustrated in FIG. 1). In such an embodiment, with the backplane of the manipulator head vertically oriented, the positioning of the manipulator head structure may allow the proximal control of the catheter/sheath to be held closely to the patient's body without substantial structural interference. In an embodiment, high-precision drive mechanisms 312, 314 for translating each of the catheter and sheath cartridges 402, 404 may be positioned generally below the manipulator bases 308, 310 to allow the respective cartridges to be positioned toward the lower area of the manipulator. By holding a close distance, the ingress angle of the catheter/sheath may be minimized, and the manipulator control may be positioned more closely to an insertion site.

Figure 3J:
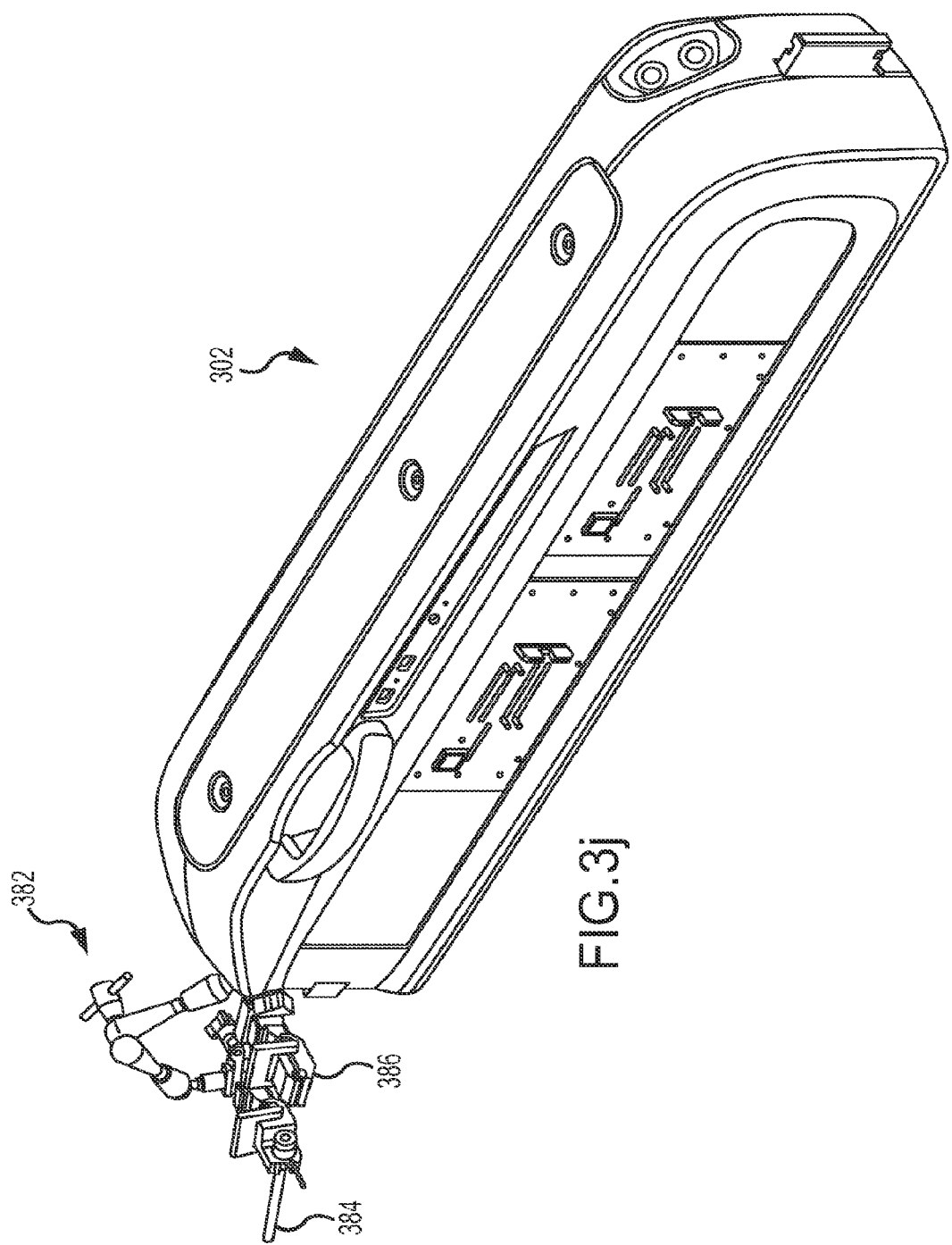
FIG. 3j is a catheter manipulator assembly including a support device.
Figure 3K:
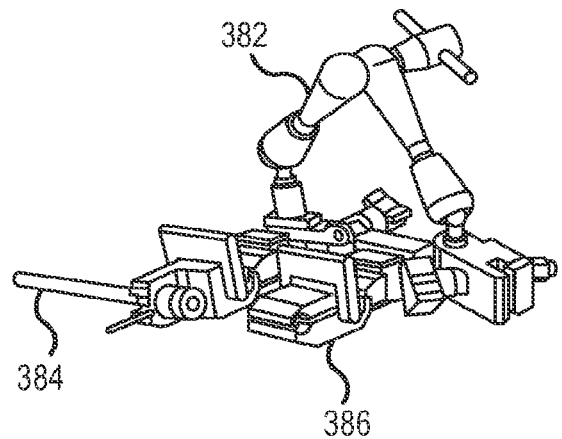
FIGS. 3k-3m illustrate embodiments of a support device.
Figure 3L:
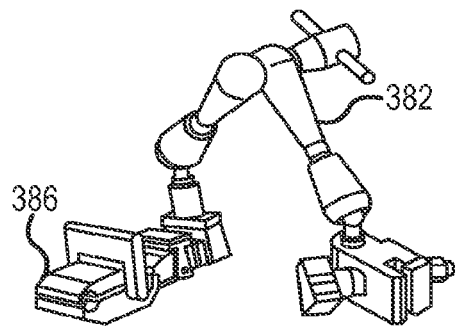
Figure 3M:
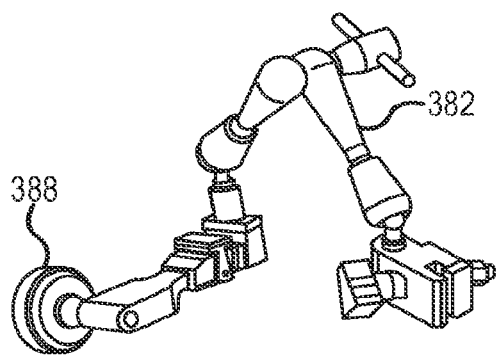
Figure 3O:
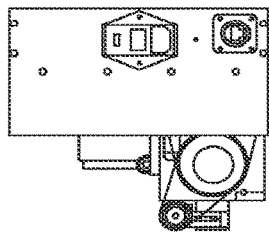
FIGS. 3n-3q are respectively enlarged left side, right side, top and front views of the robotic catheter manipulator assembly of FIG. 3a, illustrating use of the manipulator assembly with a robotic catheter rotatable device cartridge.
Figure 3P:
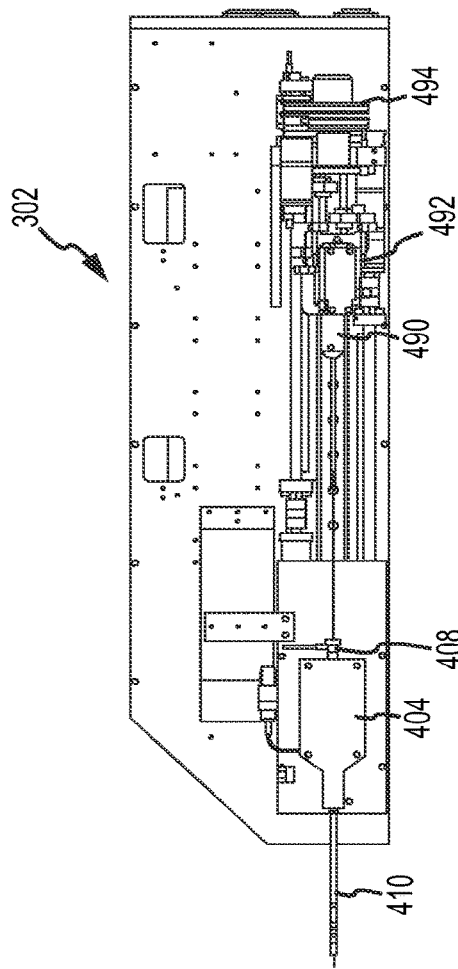
Figure 3N:
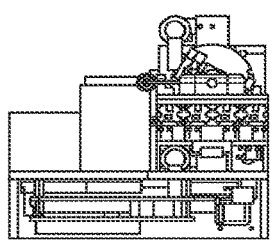

Referring to FIG. 3j, manipulator assembly 302 may include a support device 382 positioned on the distal end of the manipulator assembly and configured to receive one or more ancillary tools, such as, for example, an introducer 384, a guide 386, or a hemostasis pad 388. Various configurations of support devices and ancillary tools are illustrated in FIGS. 3k-3m. In an embodiment the support device 382 and ancillary tools, are configured to interact with a portion of the catheter and/or sheath between the manipulator and the patient. For example, as generally illustrated in FIG. 3j-3l, introducer 384 and/or guide tube 386 may direct the catheter into the patient at a fixed angle or position while allowing the manipulator to be oriented at a different relative angle. In an embodiment, as generally illustrated in FIG. 3m, the support device 382 may include a hemostasis pad 388.

Figure 2A:
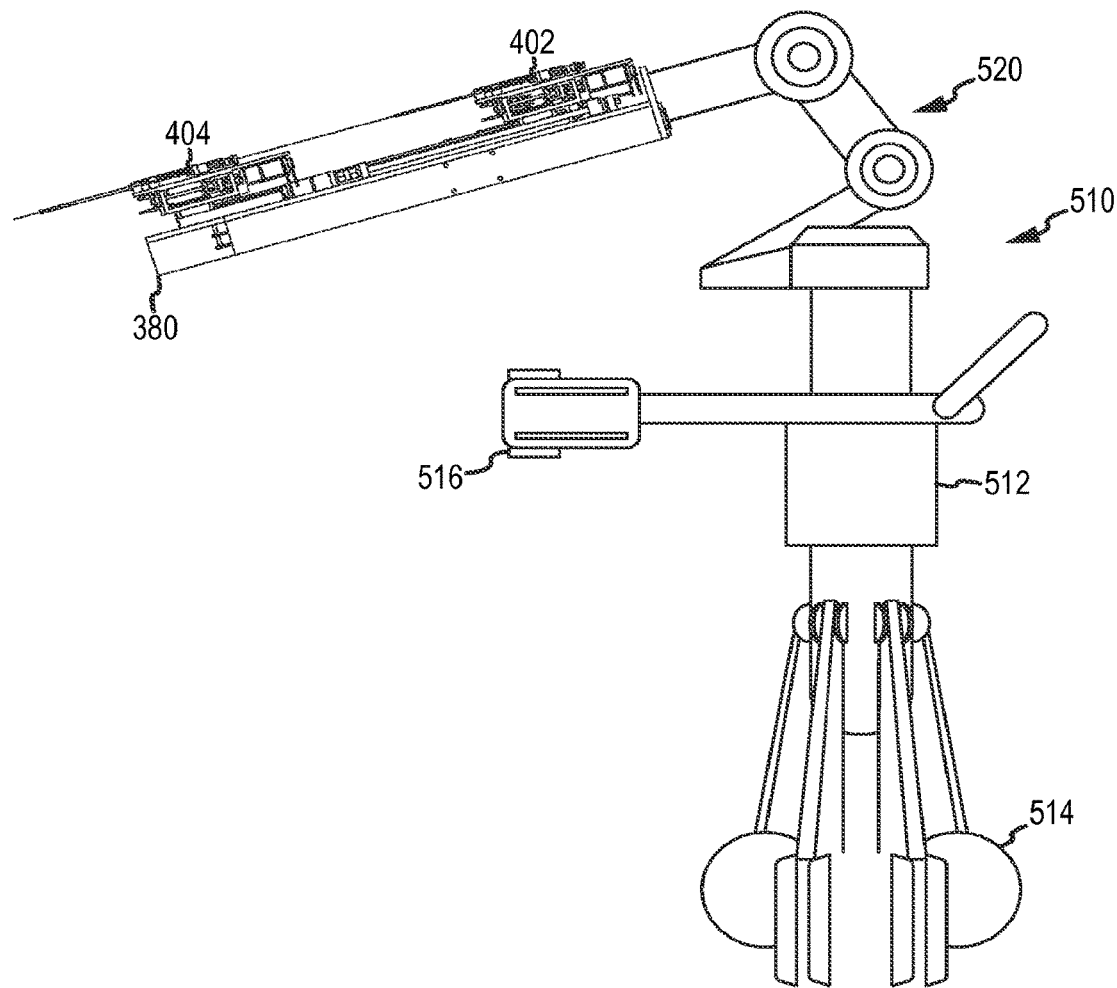
FIGS. 2a-2c are isometric and related diagrammatic views of a first embodiment of a robotic catheter manipulator support structure, with FIG. 2a illustrating a robotic catheter manipulator slightly angled from a generally horizontal position.
Figure 2B:
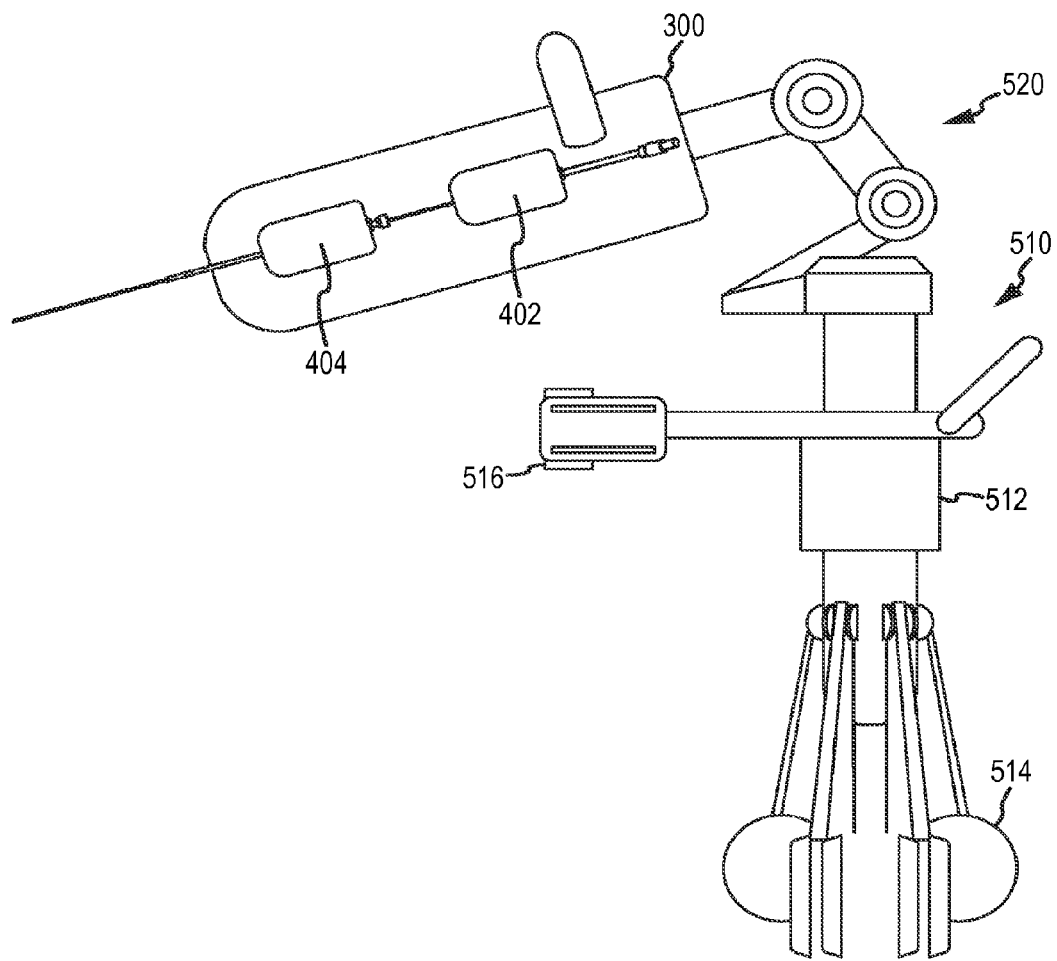
Figure 2C:
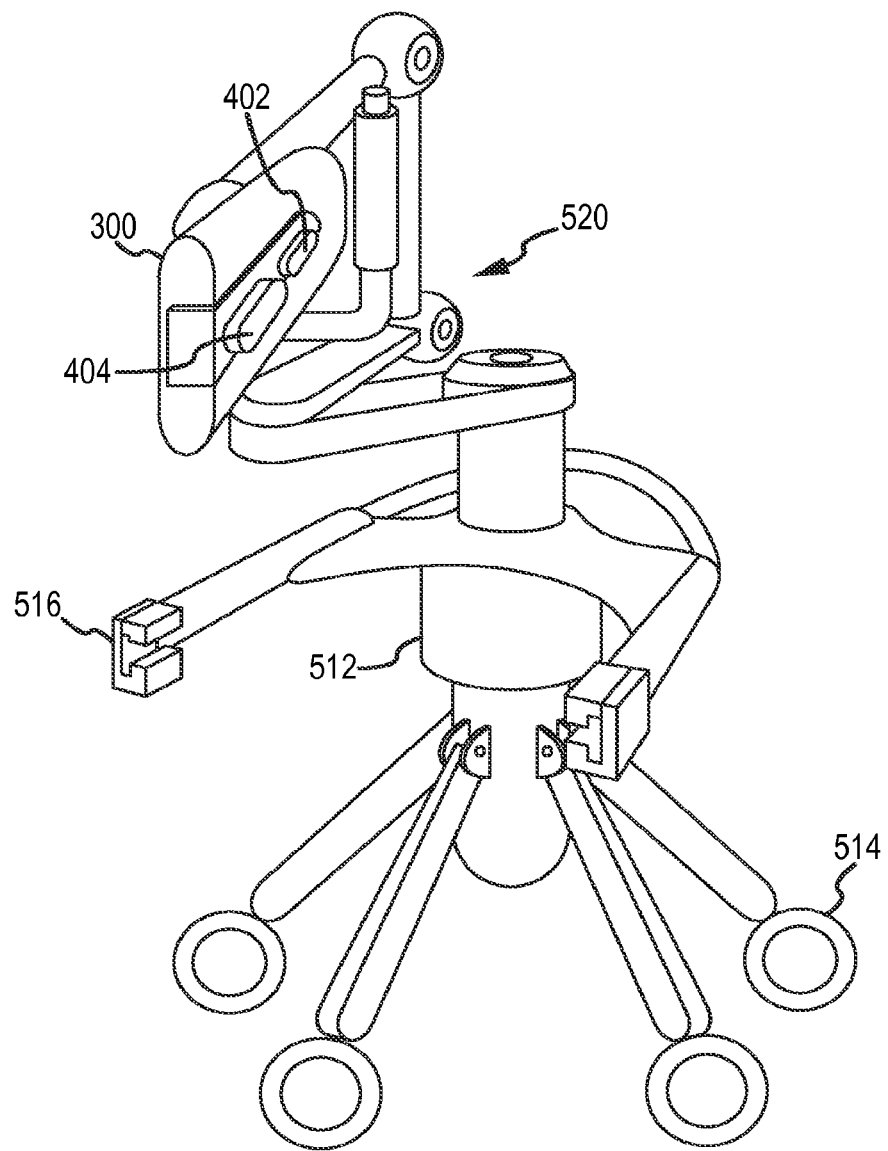
Figure 2D:
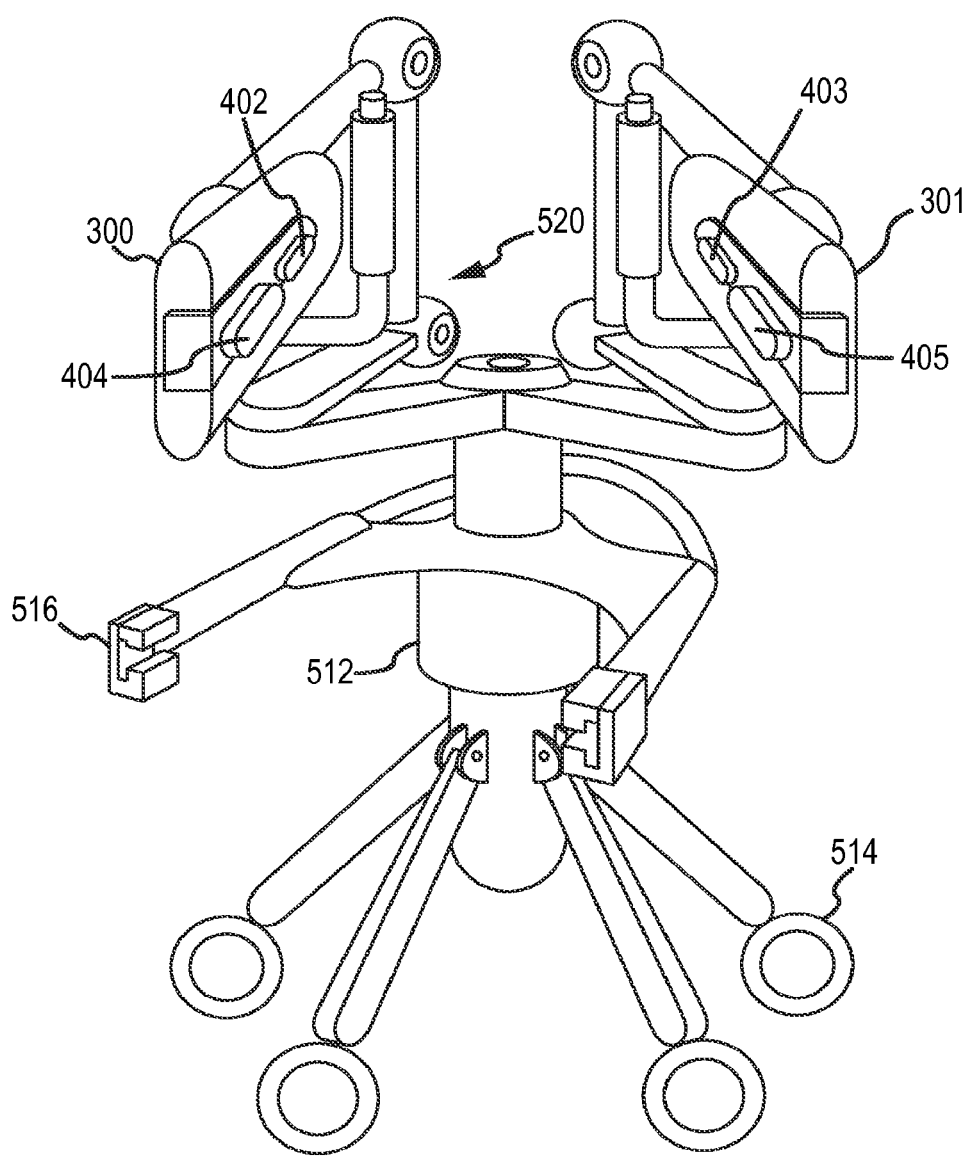
FIG. 2d is a second embodiment of a robotic catheter manipulator support structure employing two manipulator assemblies.
Figure 3Q:
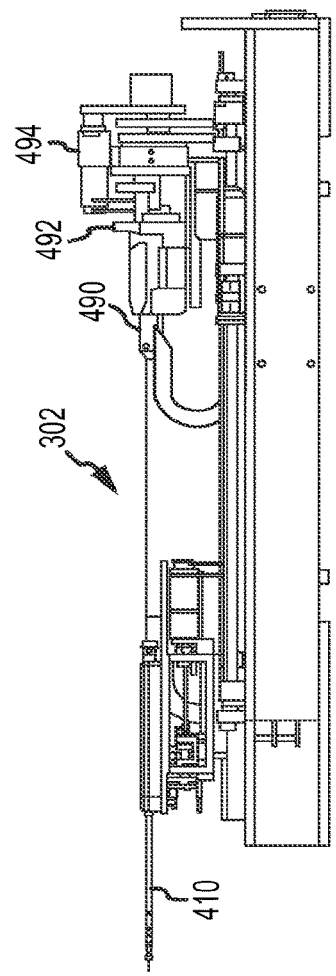

Referring to FIGS. 1-3q, particularly FIGS. 3n-3q, robotic catheter manipulator assembly 302 may be usable with a robotic catheter rotatable device cartridge 490. As shown in FIG. 3q, manipulator base 308 may be replaced with a robotic catheter rotatable drive head 492 and a robotic catheter rotatable drive mechanism 494.

Referring to FIGS. 1 and 5a-5e, catheter and sheath cartridges 402, 404 will be described in detail.

As briefly discussed above, robotic catheter system 10 may include one or more cartridges 400, with manipulator 302 including at least two cartridges 402, 404, each of which may be respectively designed to control the distal movement of either the catheter or the sheath. With respect to catheter cartridge 402, catheter 406 may be substantially connected or affixed to cartridge 402, so that advancement of cartridge 402 correspondingly advances catheter 406, and retraction of the cartridge retracts the catheter. As further shown in FIGS. 5a-5e and discussed above, in an embodiment, each cartridge 402, 404 may include slider blocks (e.g., 412, 414, 416, 418), each rigidly (and independently) connected or affixed to one of a plurality of catheter steering wires (e.g., 420, 422, 424, 426) in a manner that permits independent tensioning of each steering wire. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Sheath cartridge 404 may be designed in a similar manner as the catheter cartridge 402, but will typically be configured to provide for the passage of catheter 406. Assembly 302 may include a plurality (e.g., as many as ten or more) of independent driving mechanisms (e.g. motor driven ball screws 324).

For some embodiments, the catheter and sheath cartridge can be designed to be substantially similar, and in that context a reference to either may relate to both. For example, as shown in FIGS. 5a-5e, the design of the catheter/sheath cartridge may include upper and lower cartridge sections 428, 430, and independent slider blocks 412, 414, 416, 418. The system is not generally limited to specific material selection or formation techniques. However, in an embodiment, the upper and lower cartridge sections 428, 430 may be injection molded using a polycarbonate material. Each slider block 412, 414, 416, 418 may be connected to a separate catheter steering wire 420, 422, 424, 426, and may be formed of a Teflon-like material such as, for example, Delrin AF. When in contact with the cartridge housing portions 428, 430, such Teflon-like slider blocks may maintain a low static and dynamic coefficient of friction and may avoid the need for additional lubrication.

Figure 5A:
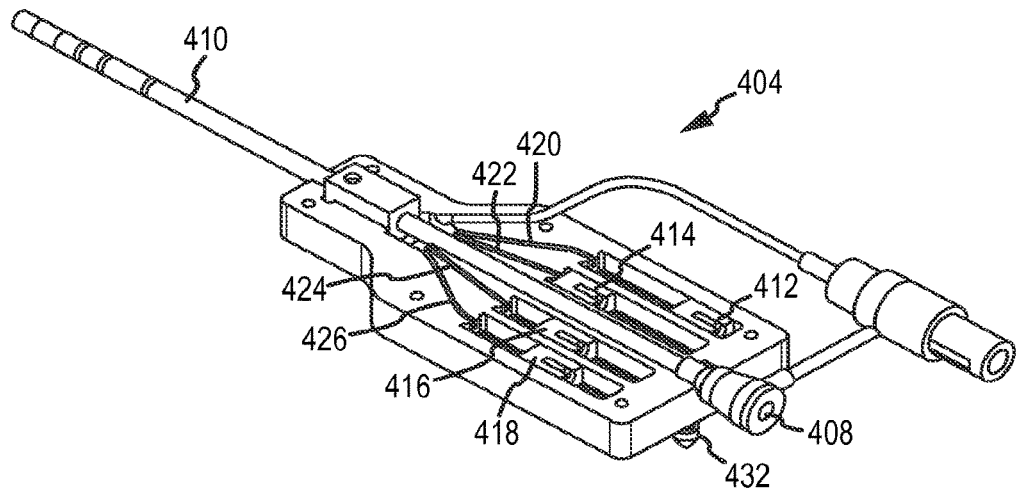
FIGS. 5a-5e are enlarged isometric views of a first embodiment of a robotic catheter device cartridge, with FIG. 3a illustrating an exemplary usage of the robotic catheter device cartridge.
Figure 5B:
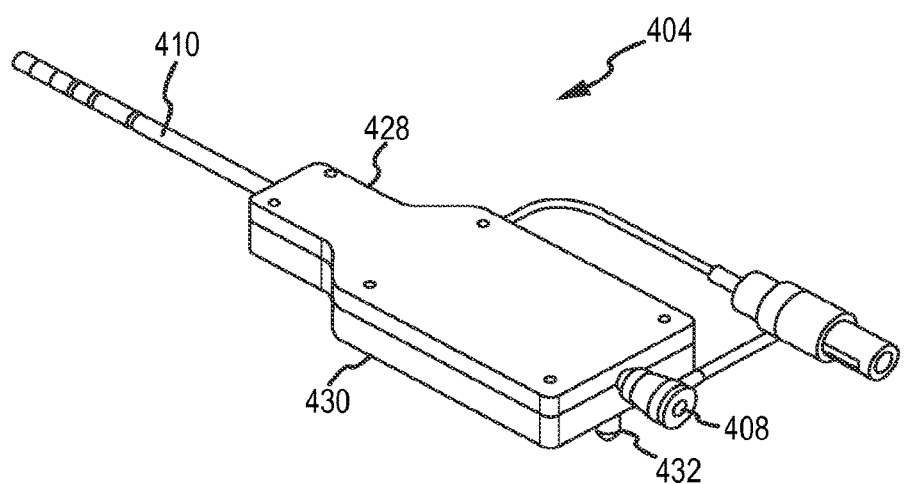
Figure 5C:
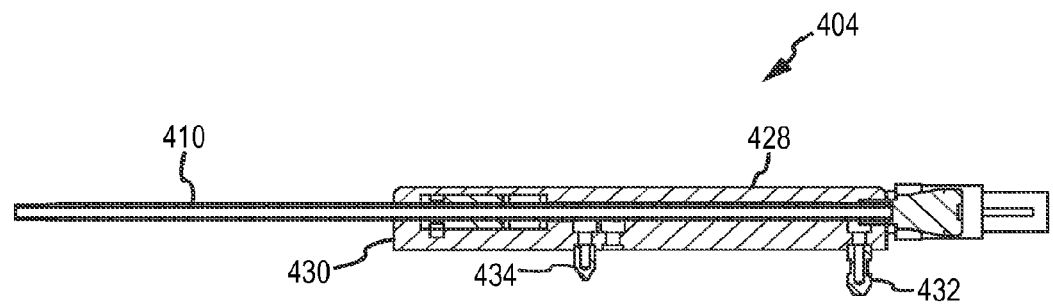
Figure 5D:
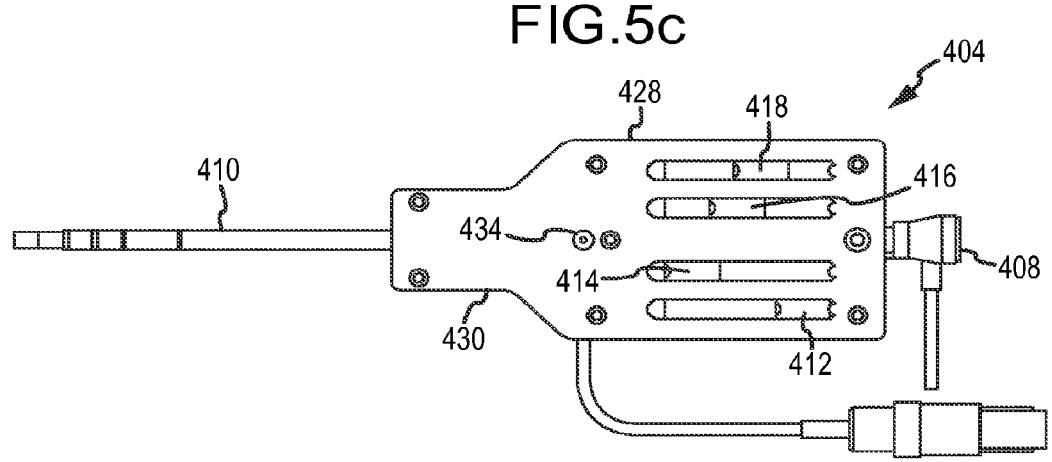
Figure 5E:
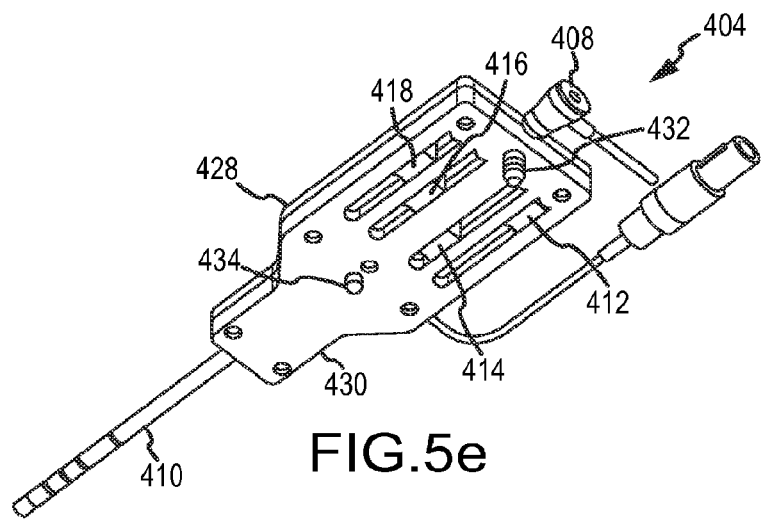
Figure 6A:
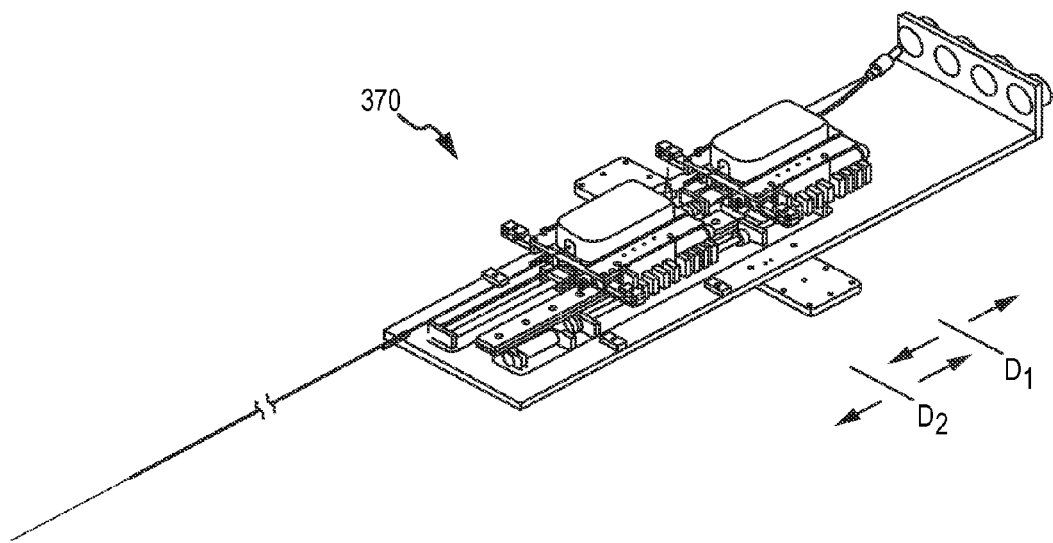
FIGS. 6a-6c are enlarged isometric views of second to fourth embodiments of a robotic catheter manipulator assembly.
Figure 6B:
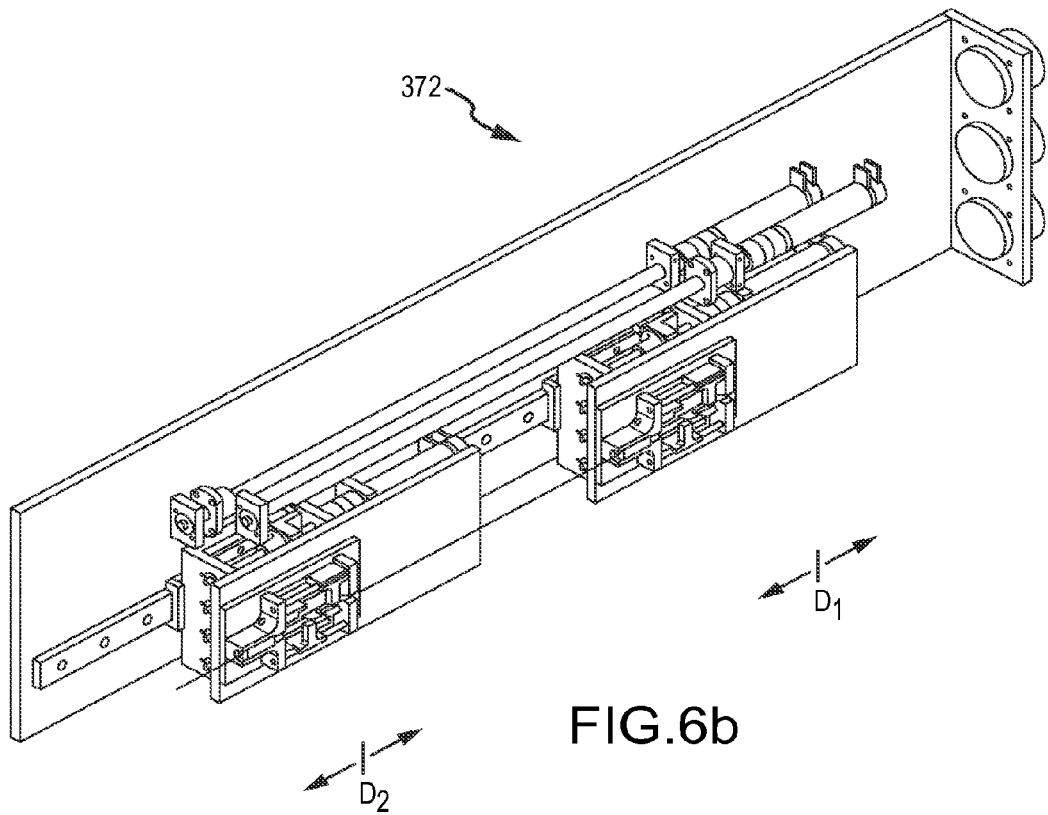
Figure 6C:
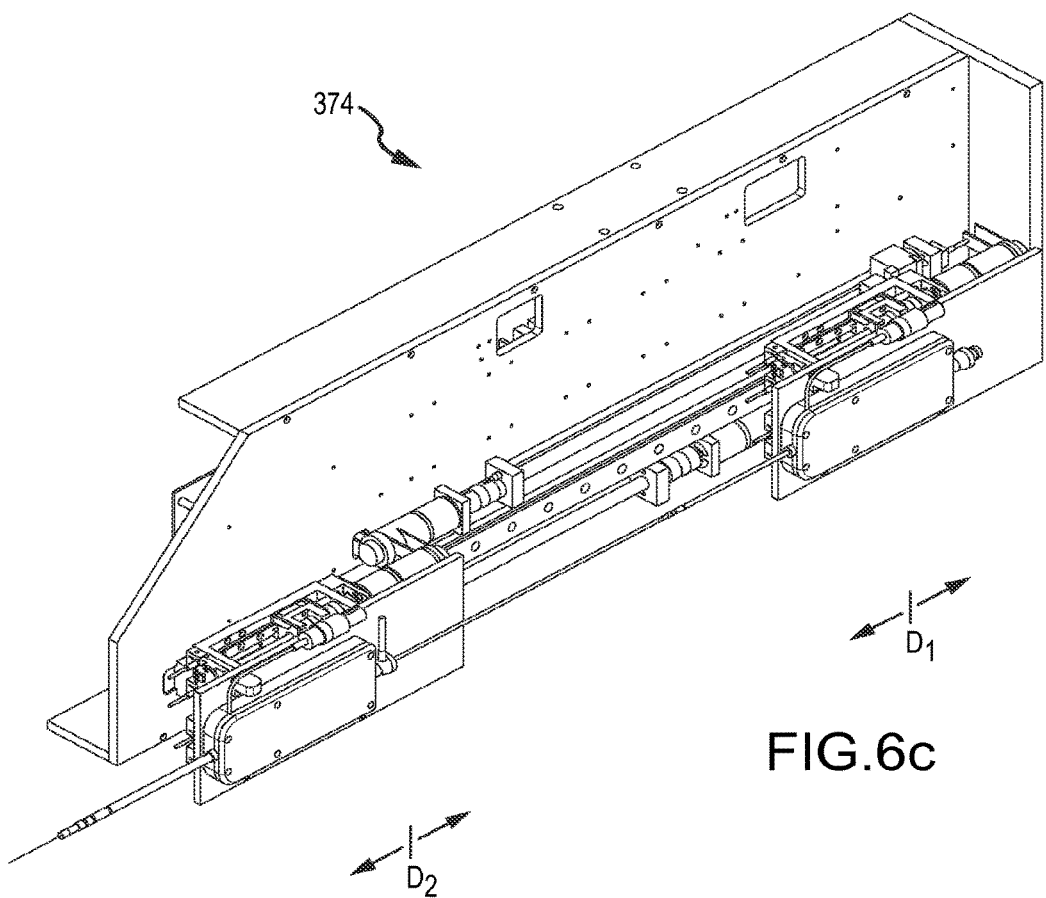

Referring to FIGS. 3a-5e and as discussed above, catheter and sheath cartridges 402, 404 may be configured to secure or lock down onto respective interconnecting catheter and sheath manipulation bases 308, 310. To couple cartridge 402 (and 404) with base 308 (and 310), one or more locking pins (e.g., 432 in FIGS. 5a, 5d and 5e) on the cartridge may engage one or more mating recesses 360 in the base (see FIG. 4a). In an embodiment, such recesses 360 may include an interference lock such as a spring detent or other locking means. In an embodiment, such other locking means may include a physical interference that may require affirmative/positive action by the user to release the cartridge. Such action may include or require actuation of a release lever 362. Additionally, as shown in FIGS. 5c, 5d and 5e, cartridge 402 (and 404) may include one or more locator pins 434 that are configured to passively fit into mating holes on the base (e.g., 364 in FIG. 4a).

In an embodiment, a user (e.g. an EP) may first manually position catheter 406 and sheath 410 (with catheter 406 inserted in sheath 410) within the vasculature of a patient. Once the devices are roughly positioned in relation to the heart, the user may then engage or connect (e.g., "snap-in") the catheter cartridge into place on interconnecting/interlocking bases 308, 310 of manipulator assembly 302, for example, by inserting the locking/locating pins 432, 434 of the cartridges into mating holes 360, 364 of respective base 308, 310. When the cartridge is interconnected with the base, each of the plurality of fingers 316, 318, 320 or 322 may fit into recesses formed between the distal edge of slider blocks 412, 414, 416, 418 and a lower portion of the cartridge housing. Such recesses are shown in, for example, FIGS. 5d and 5e.

Each finger may be designed to be actuated in a proximal direction to correspondingly push each respective slider block. The slider block can be configured to force the finger to self center on its geometry when contact is first made. Such a centering feature may be facilitated by the contact surface of the slider block. For example, as shown in FIGS. 5d and 5e, the slider block may include an engagement surface (e.g., shaped as a semi-cylindrical recess in the forward facing portion). This surface may be configured to mate or communicate with a matching round portion of a corresponding finger.

With sufficiently rigid coupling between each slider block and a corresponding steering wire, pushing a slider block in a proximal direction may cause an attached steering wire to tension and thus laterally deflect the distal end of the catheter and sheath 406, 410. Moreover, in such an embodiment, because there is no rigid connection between each finger and its associated slider block, the manipulator assembly 302 cannot pull the steering wire in a forward direction. That is, when each block is actuated, it is only possible to tension the steering wire. Furthermore, because the push-actuation of each slider block occurs near that block's bottom surface, a moment may be imposed on the block. Because such a moment may increase the likelihood of the block binding during travel, the length of the block may be optimized to reduce or minimize contact forces between the block and the cartridge housing.

The aforementioned electrical handshake between manipulation bases 308, 310 and catheter and sheath cartridges 402, 404 will be described briefly.

Robotic catheter system 10 may be useful for a variety of procedures and in connection with a variety of tools and/or catheters. Such tools and/or catheters may include, without limitation, spiral catheters, ablation catheters, mapping catheters, balloon catheters, needle/dilator tools, cutting tools, cauterizing tools, and/or gripping tools. The system may additionally include a means of identifying the nature and/or type of catheter/tool cartridge that is installed for use, and/or position or connection related information. The system may automatically access/obtain additional information about the cartridge, such as, without limitation, its creation date, serial number, sterilization date, prior uses, etc.

Further, some embodiments of the system may include an ability to "read" or detect the type or nature of the connected cartridge through the use of memory included with the disposable cartridge together with some data/signal transmission means. By way of example, each cartridge may contain a chip (e.g., an EEPROM chip) that can be electrically interfaced by the manipulator head. Such a chip could, for instance, be programmed during the manufacturing process and may electronically store various data, such as the make; model; serial number; creation date; and/or other special features associated with the cartridge or tool. Additionally the chip may contain other worthwhile information, such as an indication of previous use, catheter specific calibration or model data, and/or any other information that may relate to the safety or performance of the particular device.

In an embodiment, upon interconnecting the cartridge (e.g. 402, 404) with the manipulator head (e.g. 302), a detection means, such as an optical or magnetic sensor, may initially detect the presence of the cartridge. Once presence is detected, the manipulator may energize a chip and initiate data/signal retrieval. Such retrieved data/signal may then be used by the system to control or alter various features and/or displays based on the type of device and/or information provided. While one embodiment may use a chip (e.g., EEPROM), due to its design flexibility, another embodiment may include a wireless transmission device, such as an RFID, which may be employed to facilitate the data storage/transfer instead of, or in addition to a chip.

Referring to FIGS. 1, 2a-2d and 7a-14j generally, various embodiments of manipulator support structure 500 are disclosed.

Figure 7A:
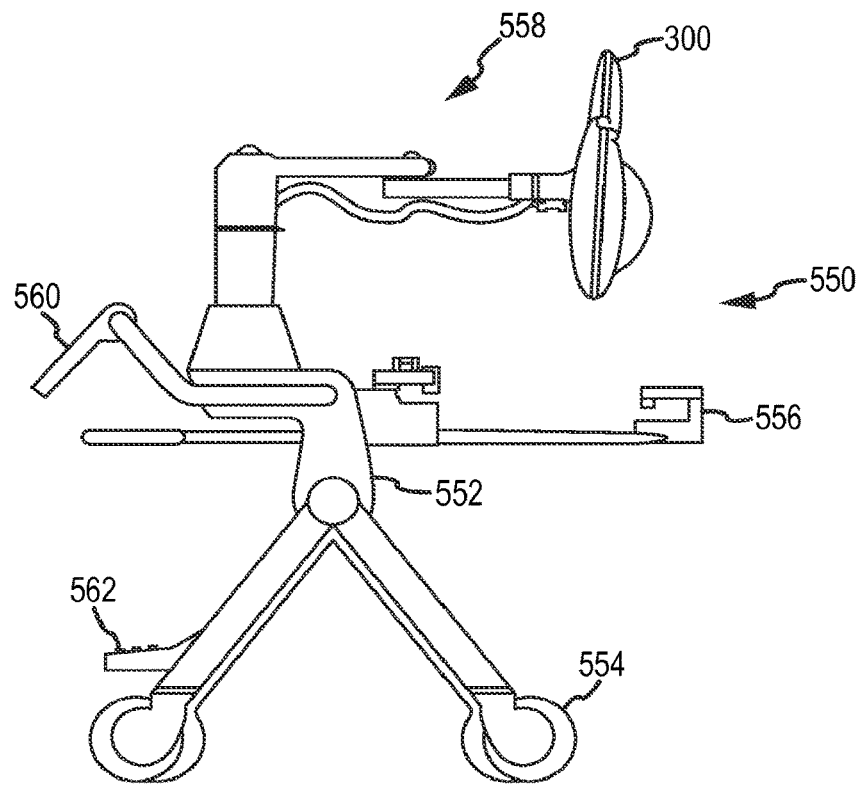
FIGS. 7a and 7b are diagrammatic views of a second embodiment of a robotic catheter manipulator support structure.
Figure 7B:
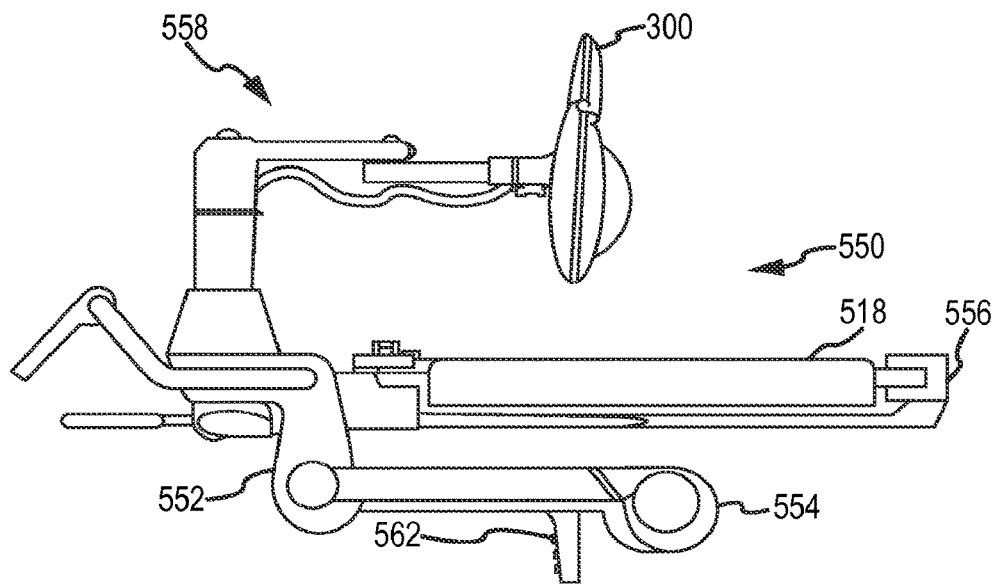

Specifically, referring to FIGS. 1 and 2a-2d, isometric diagrammatic views of a first embodiment of a robotic catheter manipulator support structure 510 (hereinafter "manipulator support structure") are illustrated. Manipulator support structure 510 may generally include a support frame 512 including retractable wheels 514 and attachment assembly 516 for attachment to operation bed 518. A plurality of support linkages 520 may be provided for accurately positioning one or more robotic catheter manipulator assemblies 300/302. As shown in FIGS. 7a and 7b for a second embodiment 550 of manipulator support structure, in use, manipulator support structure 510 may be wheeled to operation bed 518 and attached thereto by attachment assembly 516. Thereafter, wheels 514 may be retracted as shown in FIG. 7b. FIG. 2d illustrates an embodiment where multiple manipulator assemblies are provided on a common manipulator support structure 510. As generally illustrated in FIG. 2d, a second manipulator 301 may be identical to the first manipulator 300, though may include cartridges 403 and 405 that are designed to perform different tasks than the cartridges 402, 404 on the first manipulator 300.

In an embodiment, as generally illustrated in FIG. 2d, multiple manipulators 300, 301 may be used together during a single procedure. In such a procedure, each manipulator may control a catheter extending through a different anatomical lumen. For example, one catheter may extend into the left femoral vein, while another catheter may extend through the right femoral vein. Alternatively, or additionally, one or more catheters may extend through the right or left subclavian or internal jugular veins. In an embodiment, each manipulator 300, 301 may control the positioning of one or more distal tools, where the tools may be similar or different in nature. In one embodiment, two manipulators may control the positioning of two ablation electrodes. In another embodiment, one manipulator (e.g., manipulator 300) may control an ablation catheter, while a second manipulator (e.g., manipulator 301) controls a mapping electrode. In a another embodiment, the system may be configured to test the effectiveness of an isolation procedure by using one manipulator to stimulate tissue, while a second manipulator is configured to measure transmitted impulses (or lack thereof). It should be understood that any combination of ablation, mapping, stimulation, ultrasound, cautery, or surgical tips may be used in conjunction with any of the one or more manipulators.

Referring to FIGS. 7a and 7b, isometric diagrammatic views of the second embodiment of a manipulator support structure 550 are illustrated. Manipulator support structure 550 may generally include a support frame 552 including retractable wheels 554 and attachment assembly 556 for attachment to operation bed 518. A plurality of support linkages 558 may be provided for accurately positioning robotic catheter manipulator assembly 300. As shown in FIG. 7a, a handle 560 may be provided for assisting a user with extending attachment assembly 556 to an opposite side of bed 518. As shown in FIGS. 7a and 7b, in use, manipulator support structure 550 may be wheeled to operation bed 518 and attached thereto by attachment assembly 556. Thereafter, wheels 554 may be pivoted upwards upon release by a step-pedal system 562 to be positioned out of the path of operating personnel.

Referring to FIGS. 8a-8c, isometric and related diagrammatic views of a third embodiment of a manipulator support structure 600, and various components thereof are illustrated. Manipulator support structure 600 may generally include a portable unit 602 for transportation of manipulator support structure 600 and its related components. Structure 600 may include attachment assembly 604 for attachment to operation bed 518, and a plurality of support linkages 606 for accurately positioning robotic catheter manipulator assembly 300. Referring to FIGS. 8a and 8b, in use, manipulator support structure 600 may be wheeled to operation bed 518 and attached thereto by attachment assembly 604, and thereafter detached and placed in portable unit 602 for transportation.

Referring to FIGS. 9a and 9b, isometric and related diagrammatic views of a fourth embodiment of a manipulator support structure 650 are illustrated. Manipulator support structure 650 may generally include a track mounted unit 652 for movement of manipulator support structure 650 and its related components. Structure 650 may include attachment assembly 654 for attachment to ceiling or otherwise mounted track 656, and a plurality of support linkages 658 for accurately positioning robotic catheter manipulator assembly 300. Referring to FIGS. 9a and 9b, in use, manipulator support structure 650 may be positioned relative to operation bed 518 and locked in position during use, and moved out of the use position or otherwise re-configured to a stowed position by re-positioning of support linkages 658. As shown in FIG. 9b, manipulator support structure may be moved generally horizontally and vertically for positioning and removal from the area of operation bed 518.

Referring to FIGS. 10a-10c, isometric and related diagrammatic views of a fifth embodiment of a manipulator support structure 700 are illustrated. Manipulator support structure 700 may generally include a fixed unit 702 for movement of manipulator support structure 700 and its related components. Structure 700 may include attachment assembly 704 for attachment to the floor, and a plurality of support linkages 706 for accurately positioning robotic catheter manipulator assembly 300. In use, manipulator support structure 700 may be mounted in place relative to operation bed 518, or alternatively, bed 518 may be positioned adjacent structure 700. After use, structure 700 may be re-configured to a stowed position by re-positioning of support linkages 706.

Figure 11C:
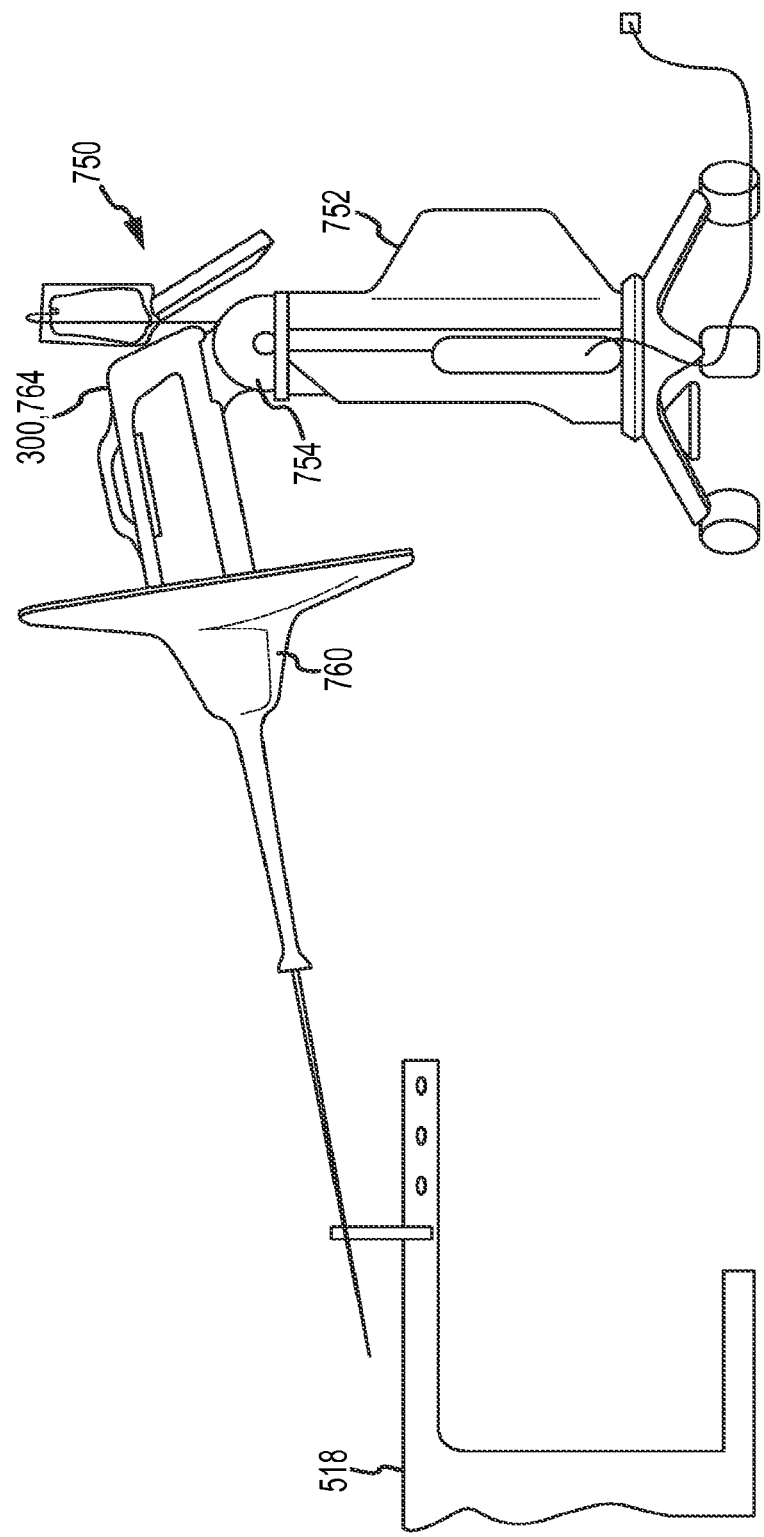
Figure 11D:
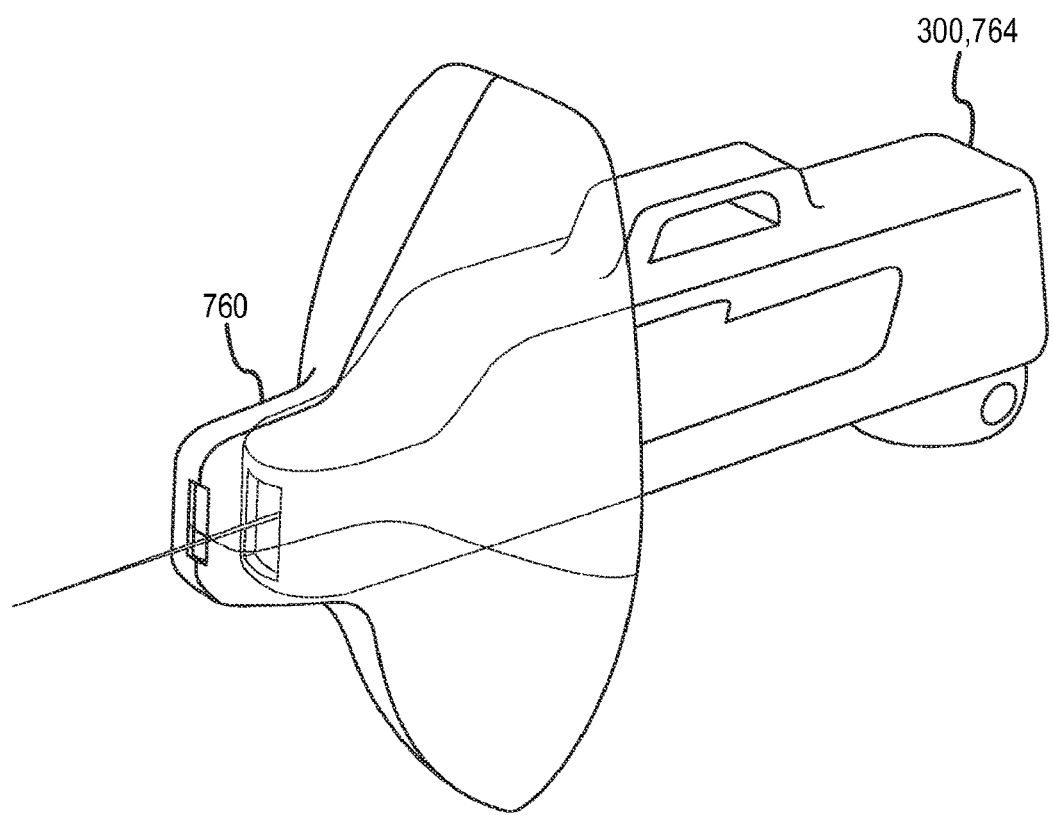
Figure 11E:
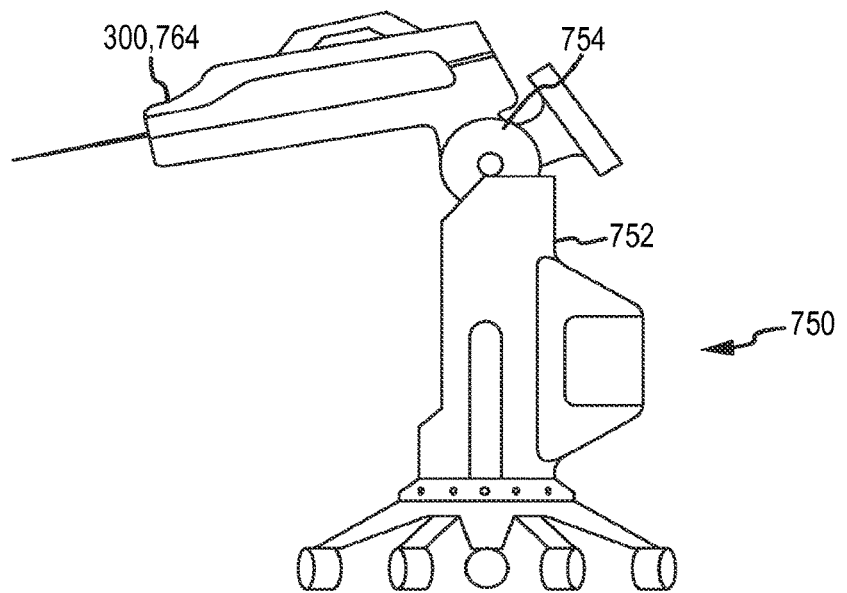

Referring to FIGS. 11a-11h, isometric and related diagrammatic views of a sixth embodiment of a manipulator support structure 750, and various components thereof are illustrated. Manipulator support structure 750 may generally include a portable unit 752 for movement of manipulator support structure 750 and its related components. Structure 750 may include a pivotable support 754 for accurately positioning robotic catheter manipulator assembly 300. Pivotable support 754 may be pivotable about generally vertical and horizontal axis 756, 758. As shown in FIGS. 11c and 11d, a disposable sterile shield 760 may be positionable on robotic catheter manipulator assembly 300. Sterile shield 760 may isolate the manipulator from a sterile field in an operating room/EP lab environment. The sterile interface may optionally include a sealing material or component, such as a pliable gasket-type material, to allow the manipulator fingers (e.g. 316, 318, 320 and 322) to interact with the cartridge (e.g. 402, 404) without operational interference, but while maintaining a necessary degree of sterility. Such a barrier or drape may permit the manipulator to be re-used without requiring additional sterilization.

Figure 11F:
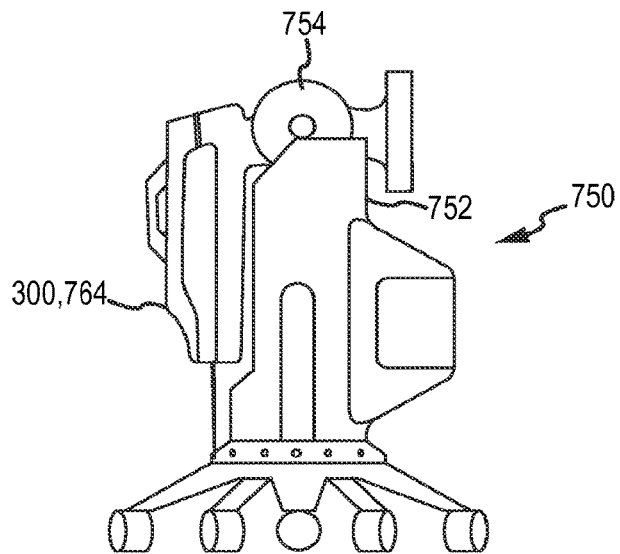
Figure 11G:
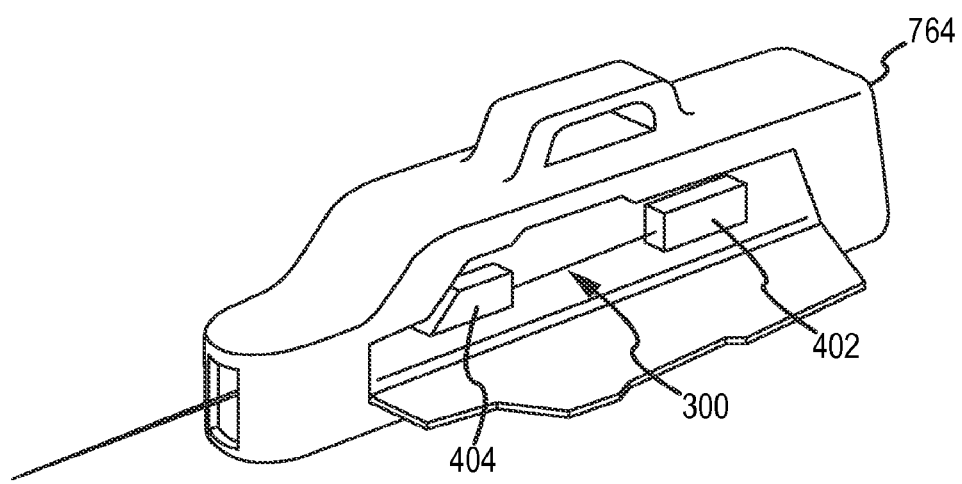
Figure 11H:
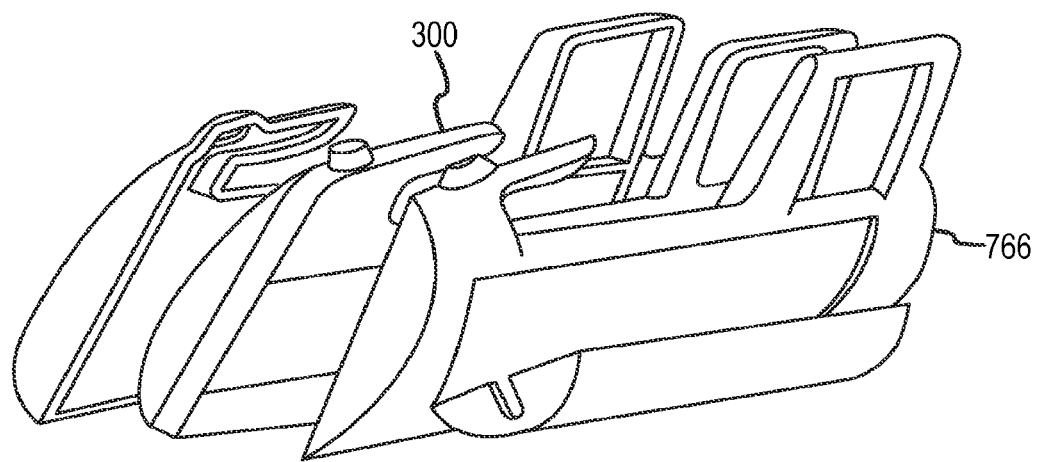

Referring to FIGS. 11a-11h, in use, manipulator support structure 750 may be placed next to operation bed 518, or alternatively, bed 518 may be positioned adjacent structure 750, with an appropriate sterile shield 760 disposed on robotic catheter manipulator assembly 300. After use, structure 750 may be collapsed as shown in FIG. 11f. As shown in FIG. 11g, cartridges 402, 404 may be attached or replaced as needed by access via a hinged cover of manipulator case 764, or alternatively, as shown in FIG. 11h, a sectioned case 766 may be provided for cartridge replacement or access to robotic catheter manipulator assembly 300.

Figure 12A:
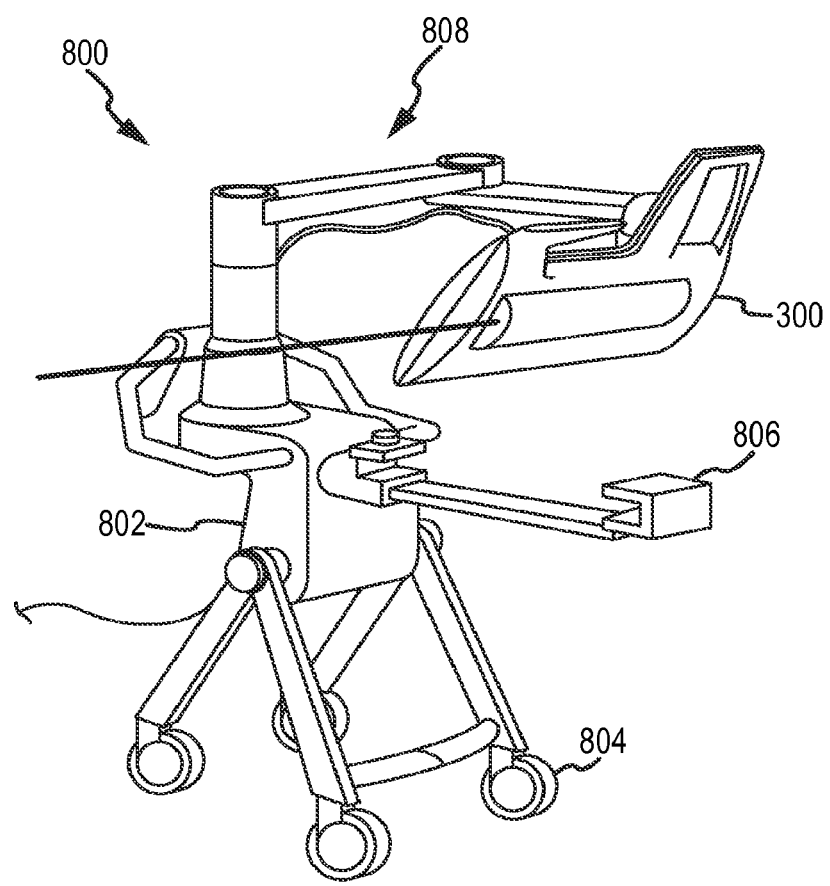
FIGS. 12a-12c are isometric and related diagrammatic views of a seventh embodiment of a robotic catheter manipulator support structure.
Figure 12B:
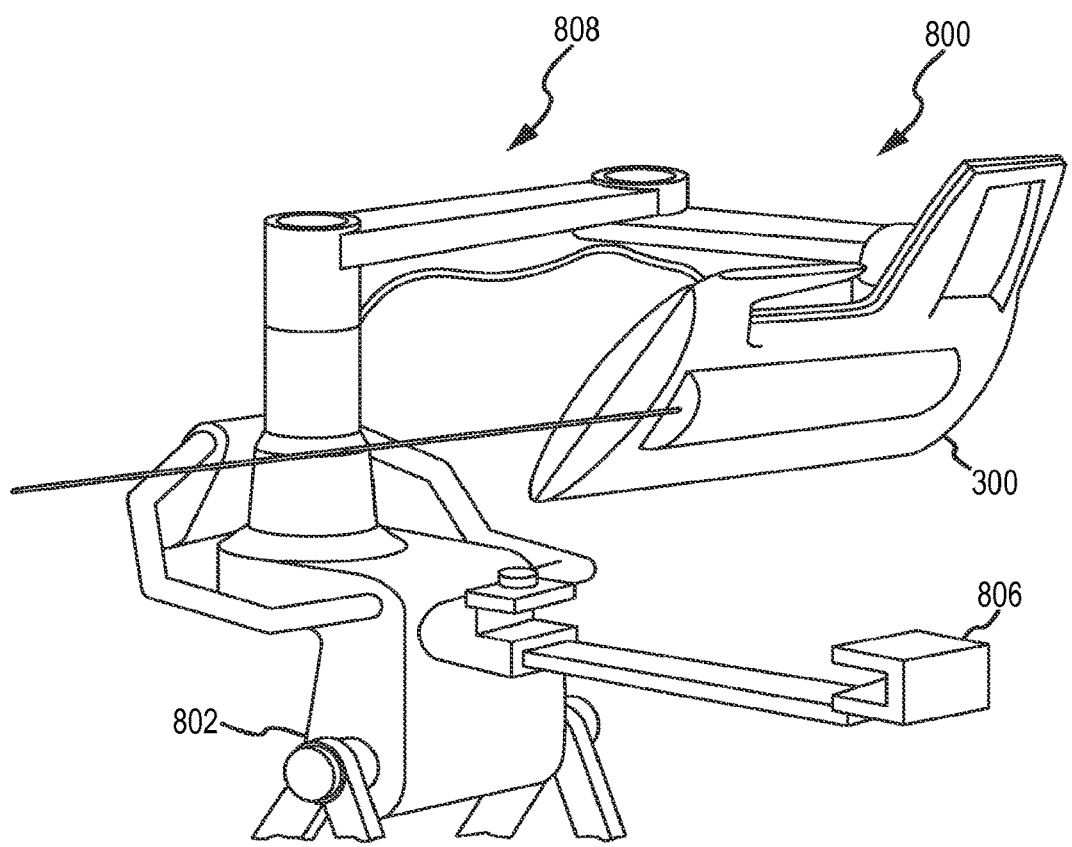
Figure 12C:
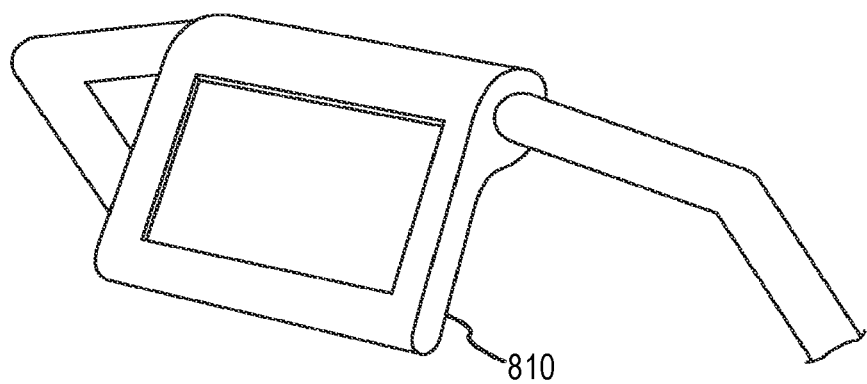

Referring to FIGS. 12a-12c, isometric and related diagrammatic views of a seventh embodiment of a manipulator support structure 800, and related components are illustrated. Manipulator support structure 800 may be similar in design to support structure 550 of FIGS. 7a and 7b. Manipulator support structure 800 may generally include a support frame 802 including wheels 804 and attachment assembly 806 for attachment to operation bed 518. A plurality of support linkages 808 may be provided for accurately positioning robotic catheter manipulator assembly 300. As shown in FIG. 12c, a touch-screen interface 810 may be provided for controlling operation of robotic catheter manipulator assembly 300. As shown in FIGS. 12a and 12b, and FIGS. 7a and 7b for support structure 550, in use, manipulator support structure 800 may be wheeled to operation bed 518 and attached thereto by attachment assembly 806.

Figure 13D:
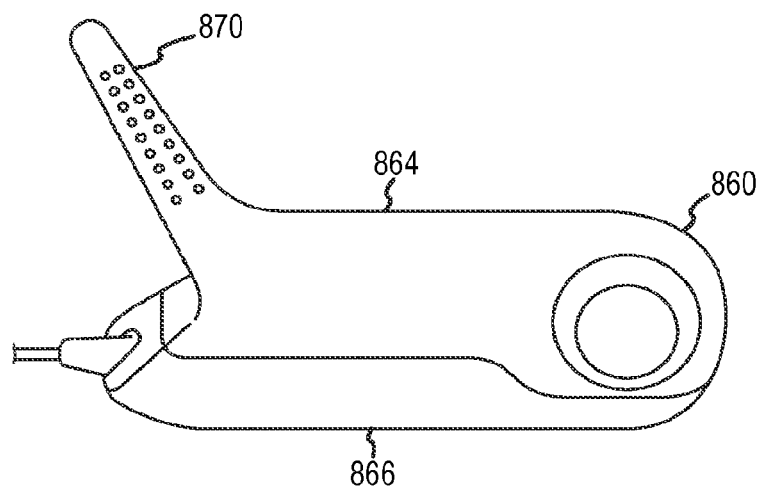
FIGS. 13a-13o are isometric and related diagrammatic views of a eighth embodiment of a robotic catheter manipulator support structure.
Figure 13E:
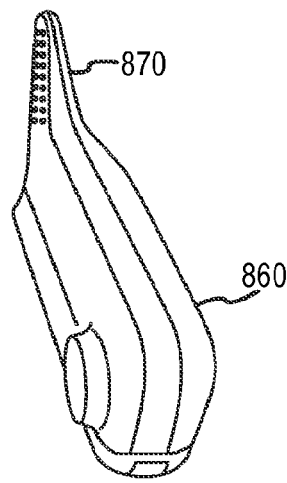
Figure 13F:
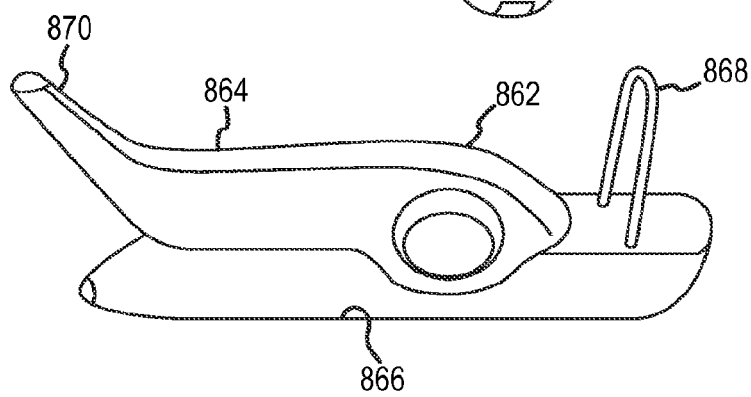
Figure 13G:
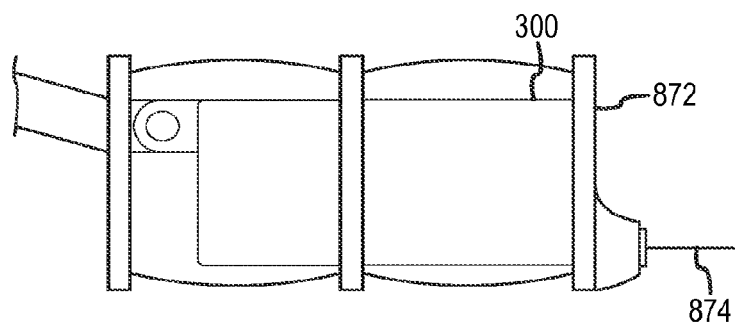
Figure 13H:
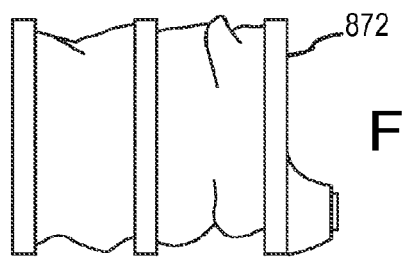
Figure 13I:
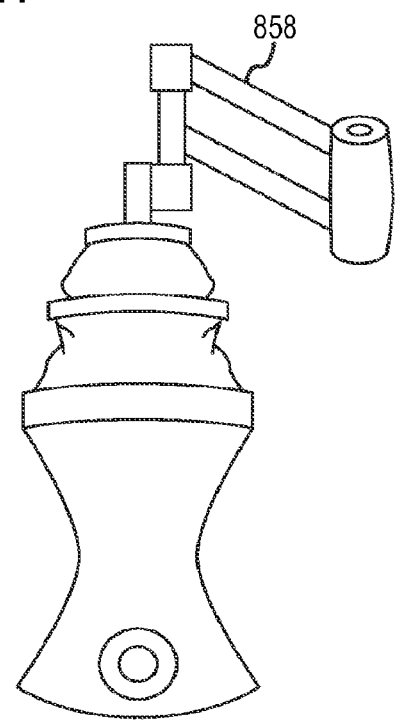
Figure 13J:
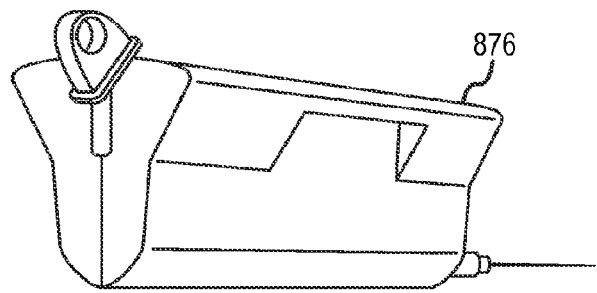
Figure 13K:
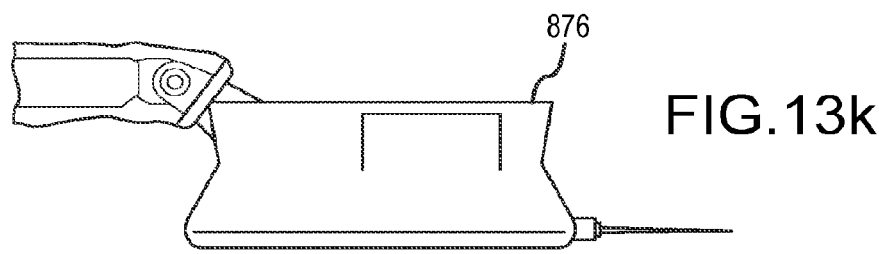
Figure 13N:
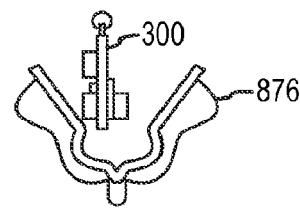
Figure 13L:
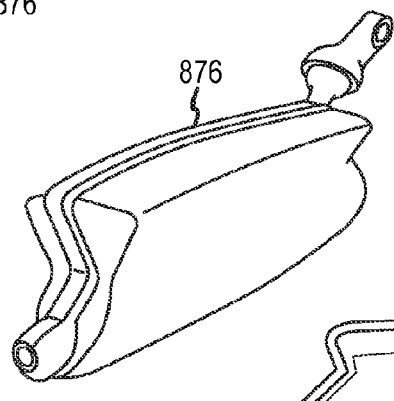
Figure 13M:
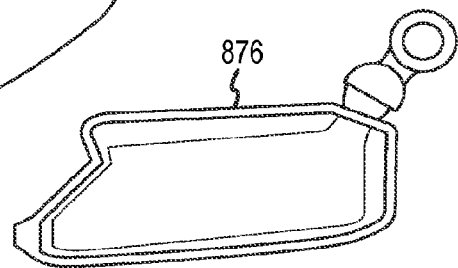
Figure 13O:
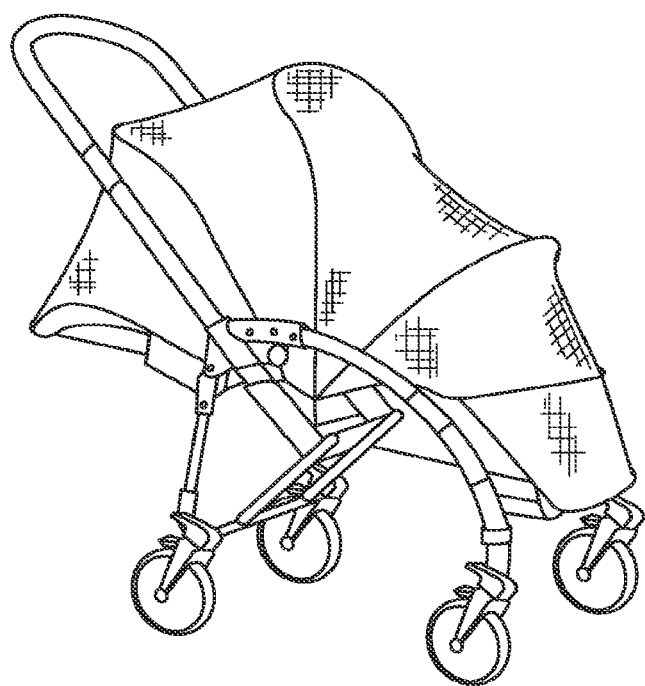

Referring to FIGS. 13a-13o, isometric and related diagrammatic views of an eighth embodiment of a manipulator support structure 850, and related components are illustrated. Manipulator support structure 850 may be similar in design to support structure 550 of FIGS. 7a and 7b. Manipulator support structure 850 may generally include a support frame 852 including wheels 854 and attachment assembly 856 for attachment to operation bed 518. A plurality of support linkages 858 may be provided for accurately positioning robotic catheter manipulator assembly 300. As shown in FIG. 13a, and FIGS. 7a and 7b for support structure 550, in use, manipulator support structure 850 may be wheeled to operation bed 518 and attached thereto by the attachment assembly 856. Referring to FIGS. 13d and 13e, a disposable cover 860 may be provided for robotic catheter manipulator assembly 300, with the cover being used with any of the embodiments of manipulator support structures disclosed herein. As shown in FIGS. 13d-13f, disposable covers 860 and 862 may include a two part top and bottom cover 864, 866, with a saline bag attachment loop 868 and integrated handle 870. As shown in FIGS. 13g and 13h, cover 872 may be collapsible for permitting use of robotic catheter manipulator assembly 300 by exposing catheter/sheath 874. As shown in FIGS. 13j-13n, a cover 876 may be opened and removed to permit unrestrained operation of manipulator assembly 300. As shown in FIG. 13o, another transportation system for the aforementioned manipulator support structures and related components is illustrated.

Figure 14A:
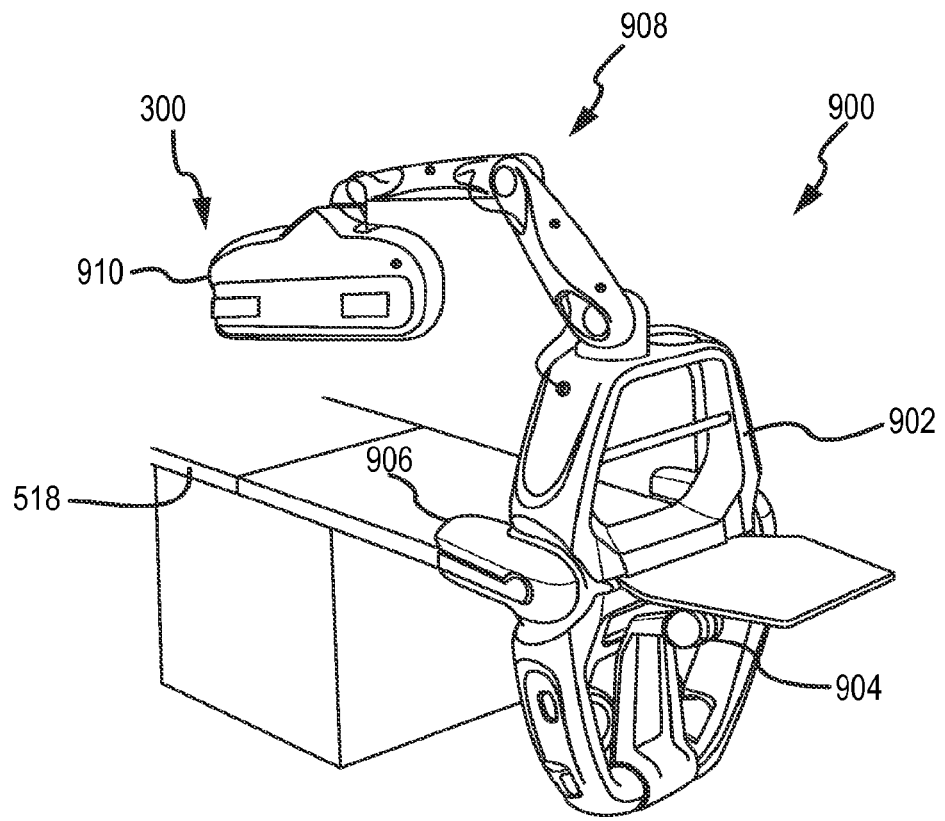
FIGS. 14a-14j are isometric and related diagrammatic views of a ninth embodiment of a robotic catheter manipulator support structure, and various components thereof.
Figure 14B:
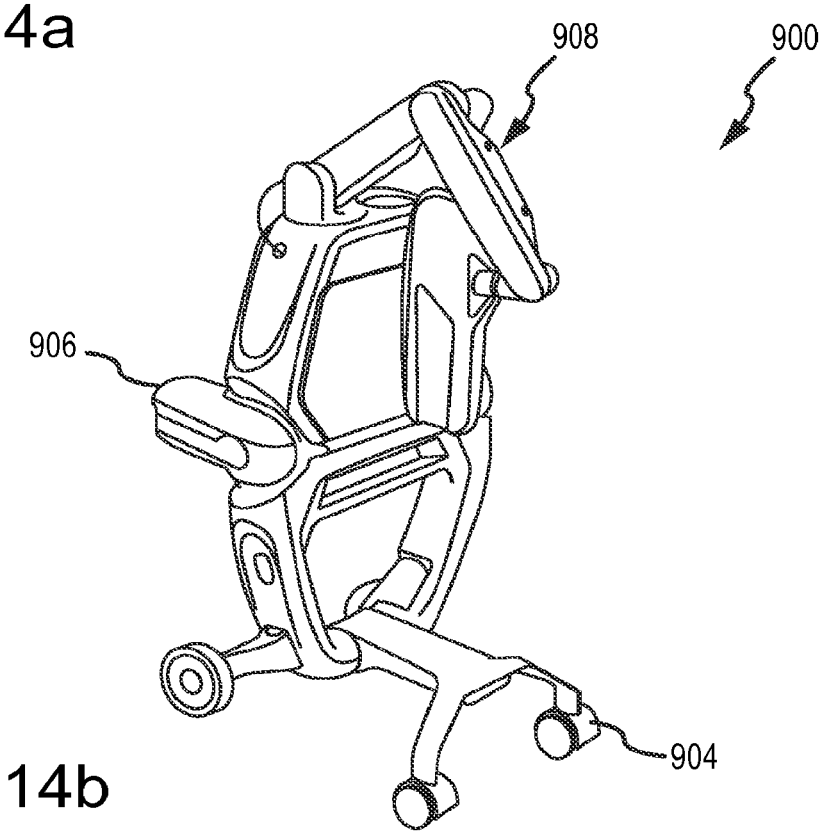

Referring to FIGS. 1 and 14a-14j, isometric diagrammatic views of a ninth embodiment of a manipulator support structure 900 and various components thereof are illustrated. Manipulator support structure 900 may generally include a support frame 902 including retractable wheels 904 and releasable attachment assembly 906 for attachment to operation bed 518. A plurality of support linkages 908 may be provided for accurately positioning robotic catheter manipulator assembly 300. As shown in FIGS. 14a and 14b, manipulator support structure 900 is illustrated as respectively disposed in the use and stowed/transport configurations. As shown in FIGS. 14a and 14b, in use, manipulator support structure 900 may be wheeled to operation bed 518 and attached thereto by attachment assembly 906. Thereafter, wheels 904 may be pivoted upwards upon release by a step-pedal (not shown) to be positioned out of the path of operating personnel.

Figure 14C:
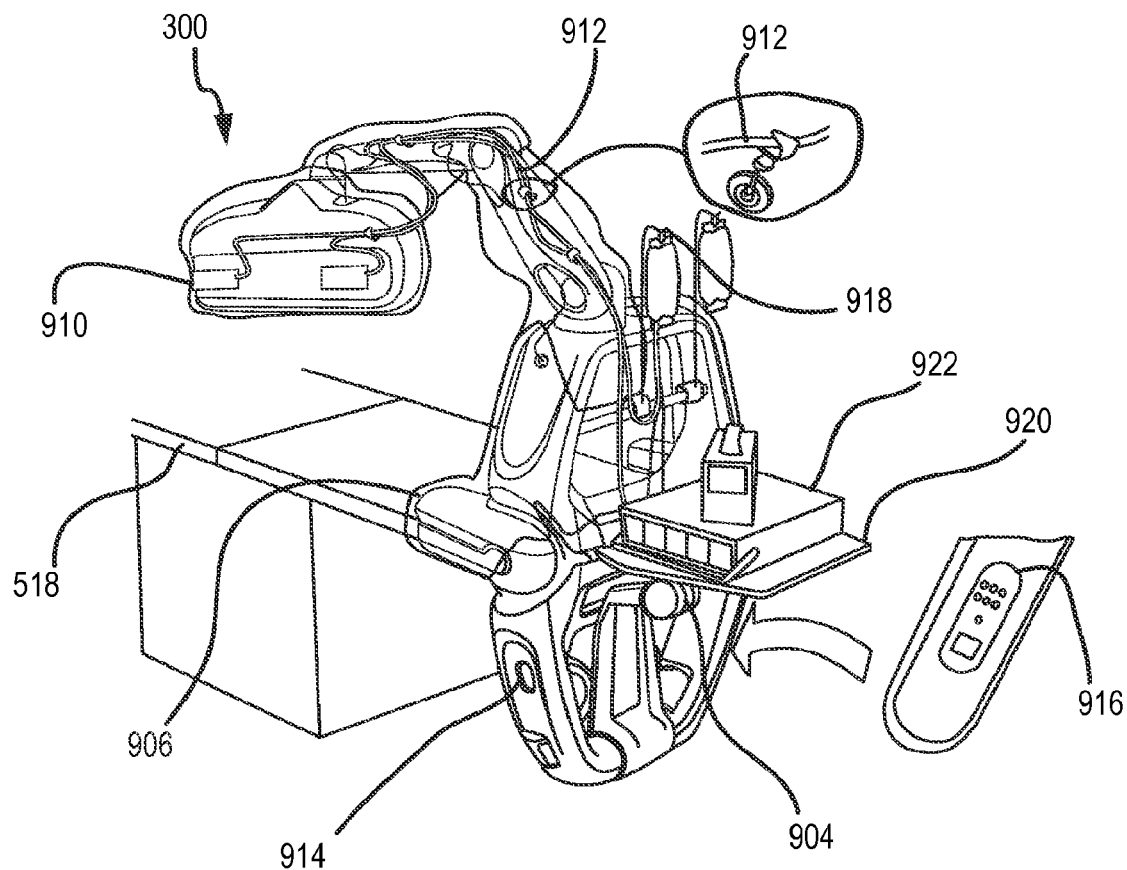

Referring to FIGS. 14a-14c, manipulator support structure 900 may include a sterile cover 910 disposed over manipulator assembly 300. Other components may include irrigation tubes 912, a USB/power connector 914, and a control module 916 including a power port, network port and an EnSite™ system connection. Saline bags may be removably hung at hangers 918, and a foldable shelf 920 may be provided for equipment, such as, a saline pump and/or ablation generator 922.

Figure 14D:
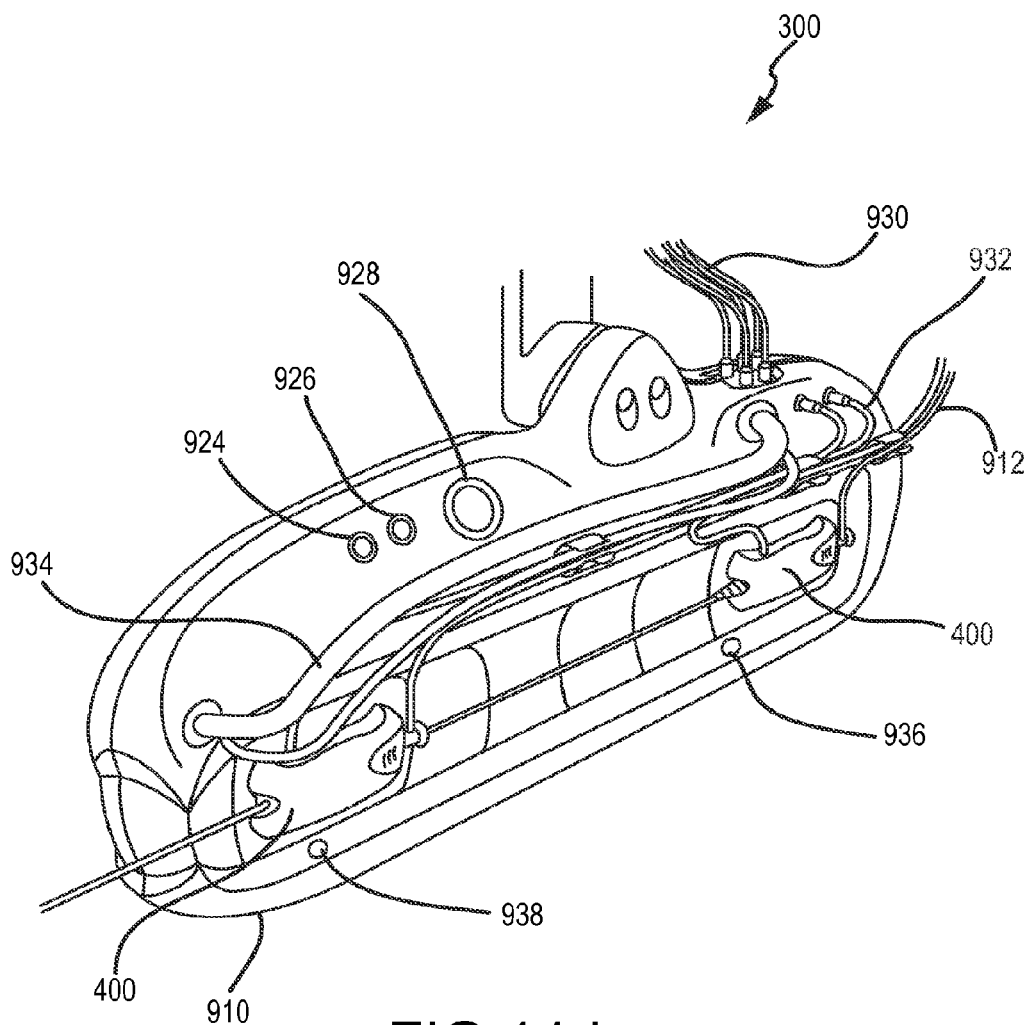
Figure 14E:
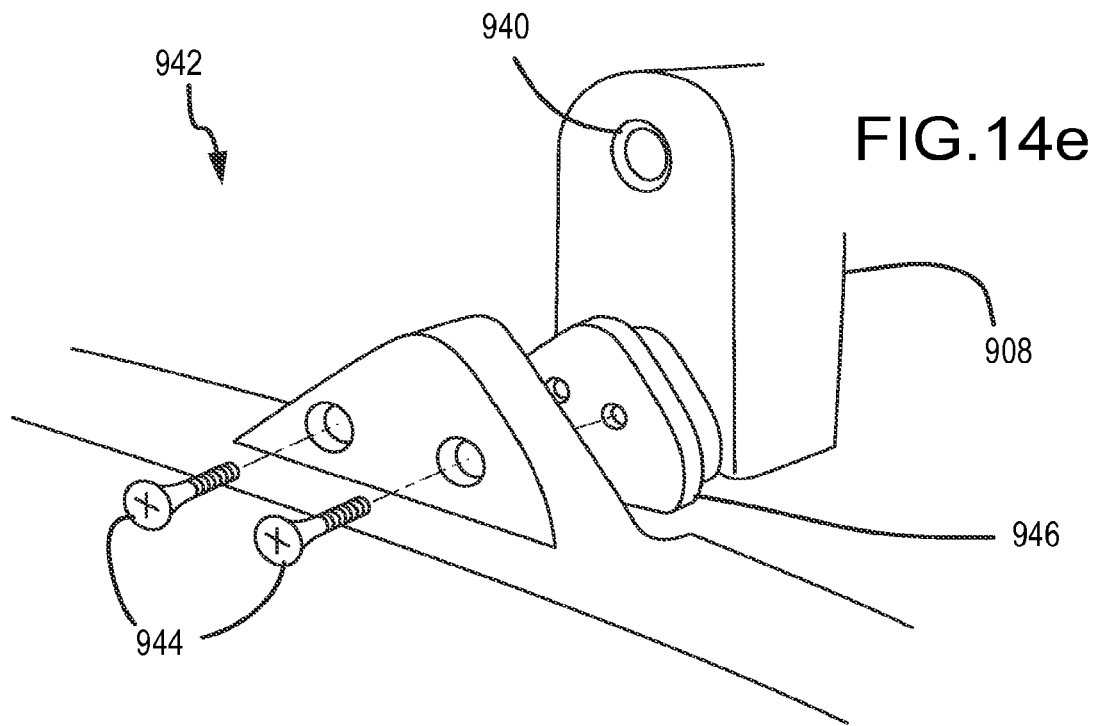
Figure 14F:
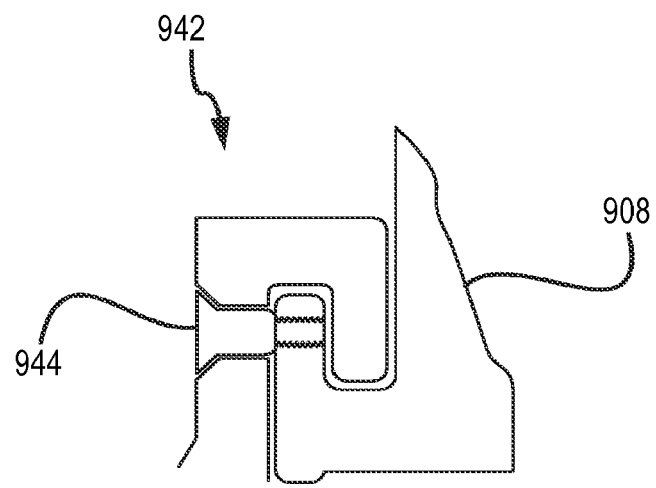

Referring to FIG. 14d, an enlarged view of manipulator assembly 300 of FIG. 1 is illustrated. As shown in FIG. 14d, manipulator assembly 300 including sterile cover 910 may further include power on/off switches 924, 926, and an emergency power switch 928. The manipulator and cartridge electrical/control connections may be provided at 930, 932. A handle 934 may be used to maneuver manipulator assembly 300 as needed. Appropriate LEDs 936, 938 may be provided for indicating proper connection of the catheter and sheath cartridges. As shown in FIGS. 14d-14f, manipulator assembly 300 may be pivotally connected to support linkages 908 at pivot point 940 by a two point rigid connection 942 including fasteners 944 and washer/aligner 946.

Figure 14G:
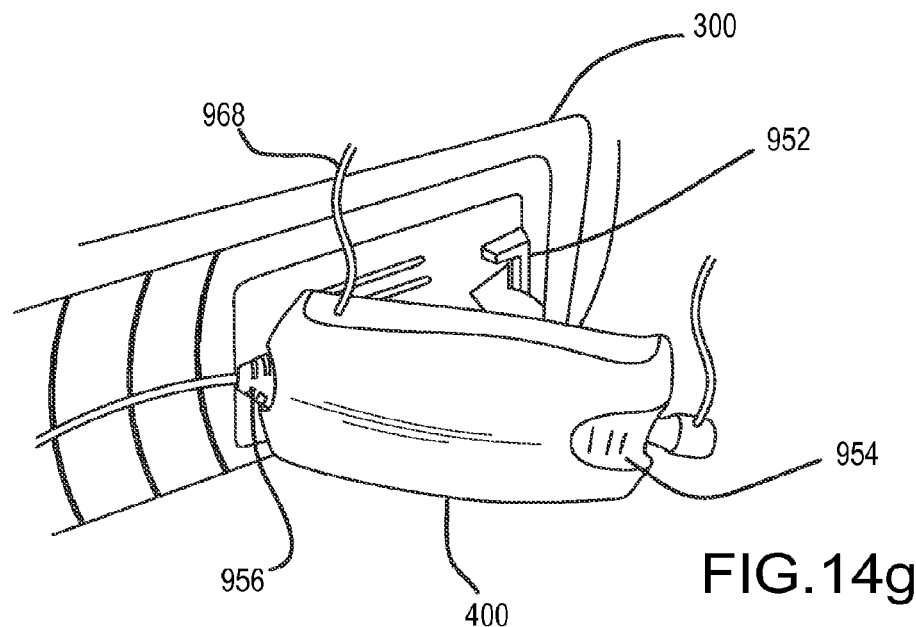
Figure 14H:
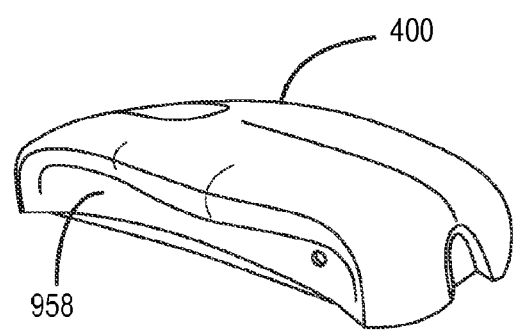
Figure 14I:
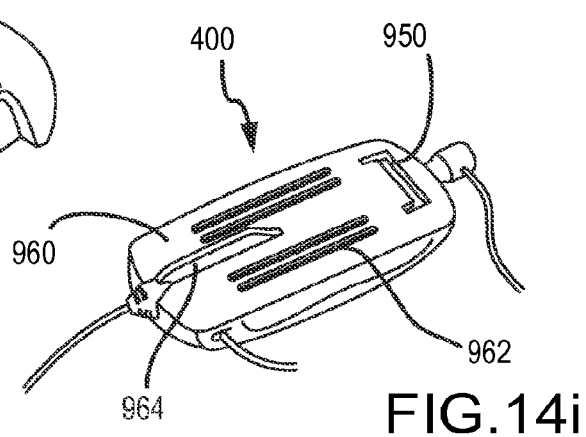
Figure 14J:
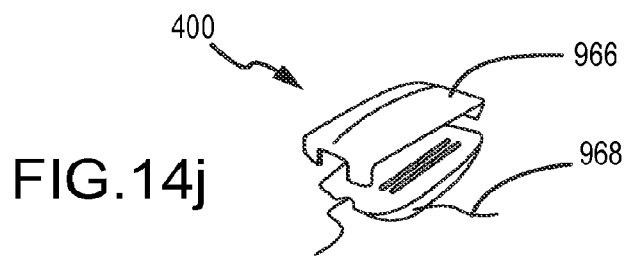

Referring to FIGS. 14a-14c and 14g-14j, for the ninth embodiment of manipulator support structure 900, cartridges 400 may include a cut-out 950 sized for a resistance snap-fit onto detent 952 of a manipulation base. A release button 954 may be provided for release of the cartridges from manipulator assembly 300. As shown in FIG. 14g, cartridges 400 may include a flexible connection for the catheter/sheath at strain relief connection 956, and electrical connection 968. As shown in FIG. 14h, an ergonomic grip area 958 may be provided for facilitating attachment, detachment and grasp of the cartridges. Referring to FIG. 14i, each cartridge may include a guide keel 960 including control pin slots 962 and control detent 964 engageable with respective detents and slots in the manipulation base (see FIG. 14g). Further, as shown in FIG. 14j, a sterile cap 966 may be provided for storage and transport of the cartridges, and removal of the cap for use. Those skilled in the art would readily appreciate in view of this disclosure that the cartridge designs of FIGS. 14g-14j may be utilized in combination with any of the other manipulator assemblies and sub-components disclosed herein, or in the above-identified commonly owned and copending applications.

Based on the discussion above, the aforementioned articulated support structures may hold manipulator assembly 300 in a position to better facilitate treatment or therapy (e.g., adjacent the femoral vein/artery to promote catheterization). Such support structures discussed in reference to FIGS. 2a-14j may, without limitation, include joints that may include a gas or hydraulic assist on each joint, and may further include a braking mechanism to decelerate or lock any moving component in place. The gas-hydraulic assist mechanisms may be provided on all joints to aid in vertical or other motion of the manipulator assembly. Additionally, electronic or electro-mechanical braking may be provided on all joints and at all degrees of freedom. The brake(s) may be configured to default to a locked state so that power is needed to enable any motion. A normally-locked configuration may be provided so that momentary power loss will not cause any unlocking or joint movement. The system may also be designed with sufficient stability to prevent movement, even under minor impacts.

Referring to FIGS. 1, 15a-19d, an embodiment of robotic catheter system 10 can include a user input device 1000. In an embodiment, the user input device 1000 may be a two or three dimensional input device that can be used to spatially manipulate a displayed catheter or a displayed target. Such an interface may be akin to, for example, a traditional computer mouse, a flight joystick, a three dimensional joystick, a 3D mouse, such as those commercially available from 3Dconnexion, a Falcon joystick from Novint Technologies Inc., a touch-screen monitor, or a spatially detected stylus. In an alternative embodiment, the interface device may allow a user to provide input to the system in a manner mimicking traditional catheter handle controls.

Figure 15A:
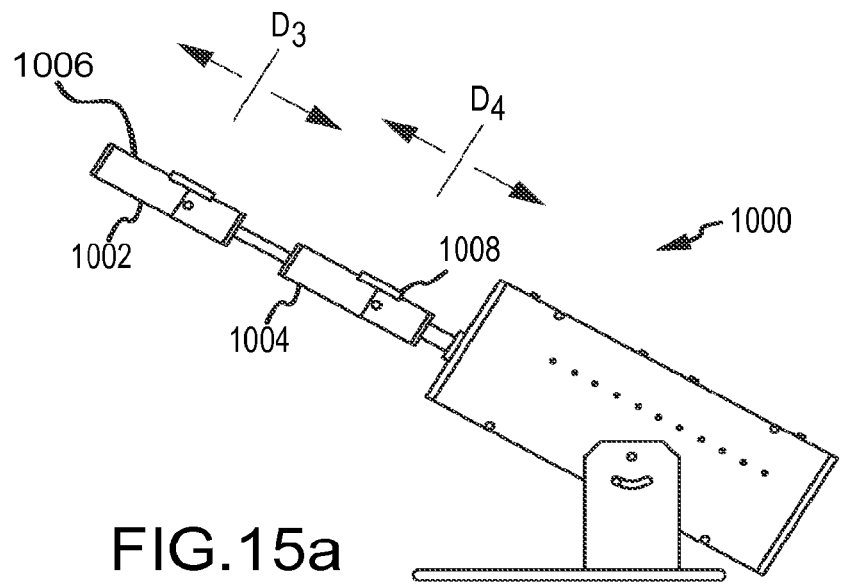
FIGS. 15a and 15b are exemplary joysticks usable with the robotic catheter system of FIG. 1.
Figure 15B:
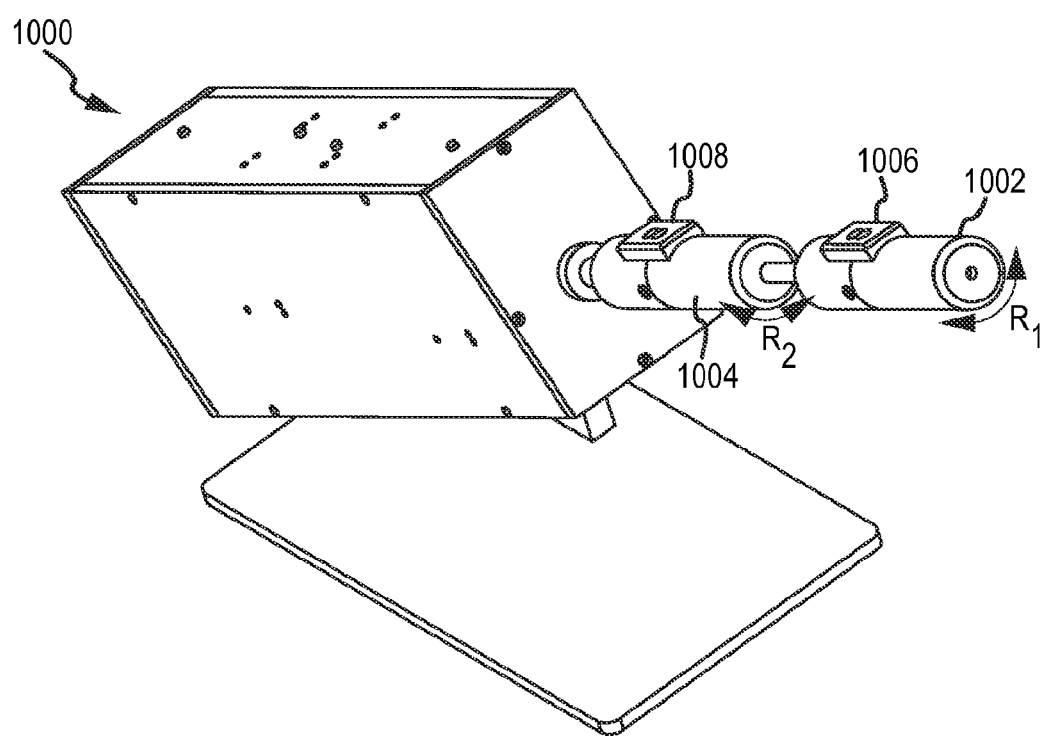

As generally shown in FIGS. 15a and 15b, an embodiment of the user input device 1000 may provide instrumented sheath and catheter handles 1002, 1004 (or vice-versa), respectively, that are able to longitudinally translate (e.g., in directions $D_3$ and $D_4$), independently rotate (in directions $R_1$ and $R_2$), and/or include one or more movable thumb tabs (e.g., elements 1006, 1008). To record the user's input, each degree of movement may be instrumented, for example, with a potentiometer or motor/encoder.

Mimicking traditional, manual catheter control, an embodiment of robotic catheter system 10 may be configured such that longitudinally translating the input handle may cause a respective longitudinal translation of the catheter/sheath distal tip. However, unlike the traditional, manual catheter, the automated catheter system would generally effectuate this translation by advancing or retracting the cartridge. Further, robotic catheter system 10 can be configured so that the rotation of either handle causes a virtual rotation of the catheter/sheath tip, and movement of a thumb tab causes a deflection in the current deflection plane.

In an embodiment of user interface device 1000, any or all motion controls of the device can be associated with/employ a spring centering feature that returns each control element to a set or "home" location after the element is released. Such a centering feature can allow for highly precise movement corrections of the distal tip by registering various input movements as incremental movement from the "home" location rather than by registering movement entirely in absolute terms.

In an embodiment, instead of thumb tab-type controls, user interface device 1000 may additionally include or substitute displacement dial controls. Furthermore, to suit the desires of the user, an embodiment of such a user interface device may permit the handles to be fully interchangeable so that various combinations of controls (e.g., dial and thumb tab handles) can be used for catheter/sheath input. In another embodiment, user interface device 1000 may further include safety buttons (e.g. "dead-man switches") that must be pressed for any joystick movement to be registered by the system. This design would prevent inadvertent motion from affecting the position of the actual catheter tip. In yet another embodiment, user interface device 1000 may further include a virtual reality surgical system, wherein the physician could be positioned within a cardiac environment (see FIG. 1), and physically position the catheter where desired or needed.

Figure 16A:
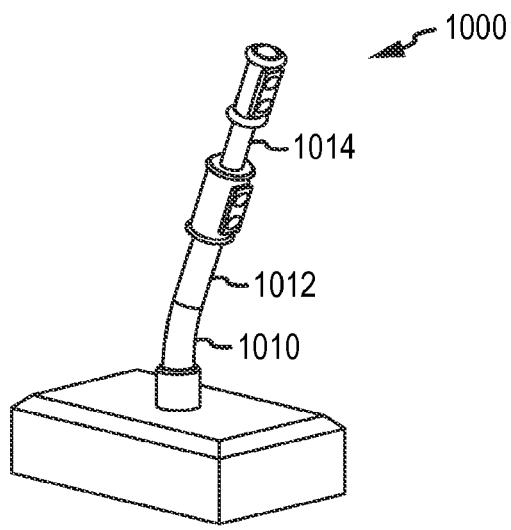
FIGS. 16a-16e are views of an exemplary construction of the joysticks of FIGS. 14a and 14b.
Figure 16B:
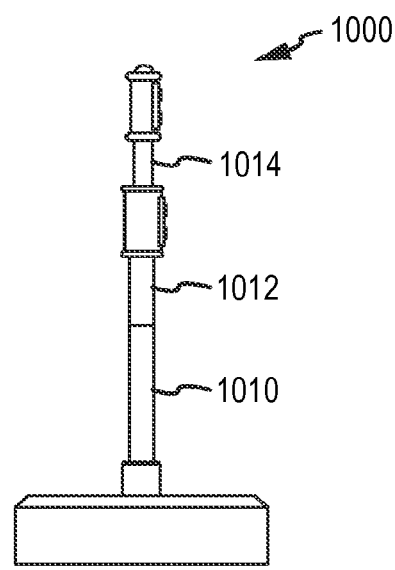
Figure 16C:
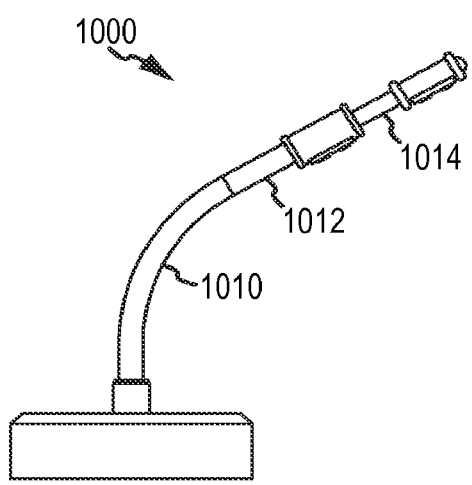
Figure 16D:
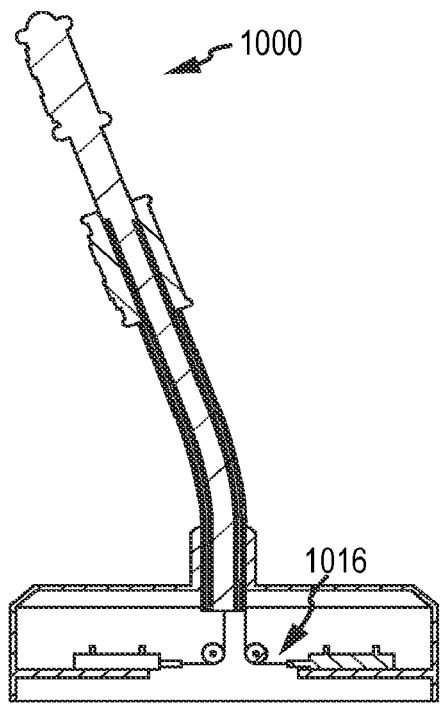
Figure 16E:
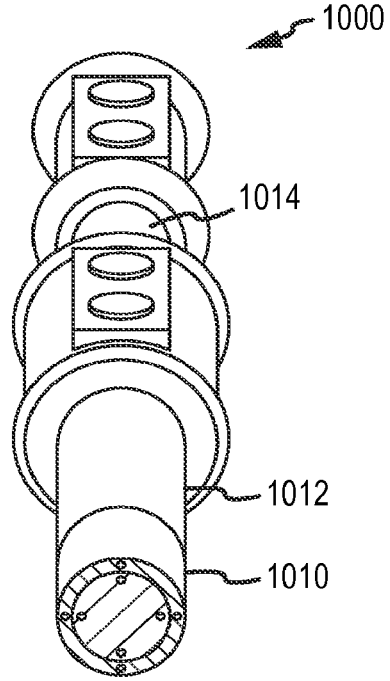

As generally shown in FIGS. 16a-16e, the physical construction of another embodiment of the user interface device 1000 may be similar to that of an actual catheter, though on a different scale. As shown in FIGS. 16d and 16e, by way of example, the various sections may be constructed with pull wires, wire ducts, and variable stiffness sections 1010, 1012, 1014 associated with a conventional catheter. In an embodiment, all motions of this device may be configured with a centering feature (e.g., a spring centering mechanism 1016), wherein the device inherently returns to an initial position when released. This configuration may be useful or suitable for an incremental input control scheme.

In other embodiments, the device may be constructed without a centering mechanism, where the absolute position of the device might instead be used to control the absolute position of the actual sheath and catheter. With such an absolute approach, the input device's physical limitations may be designed to mimic an actual catheter's and sheath's physical limitations (e.g., movement restrictions based on bend radius, catheter retracted into sheath, etc.).

To record user input, each degree of movement can generally be instrumented with either a potentiometer or motor/encoder. If a motor/encoder is used, the system may also provide haptic feedback upon certain events—such as a "feel" if the catheter were to contact a virtual wall. An embodiment of this invention may also include an ablation activation button on the distal end of the device.

Figure 17A:
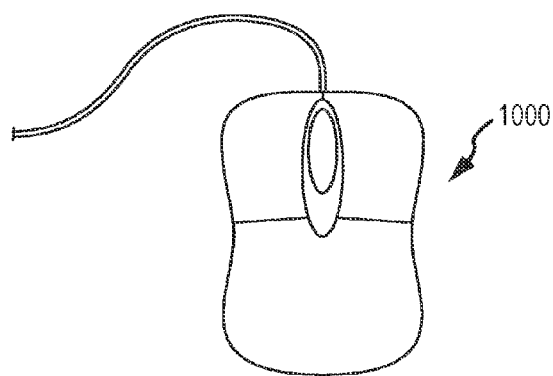
FIG. 17a is an exemplary two dimensional input device usable with a robotic catheter system.
Figure 17B:
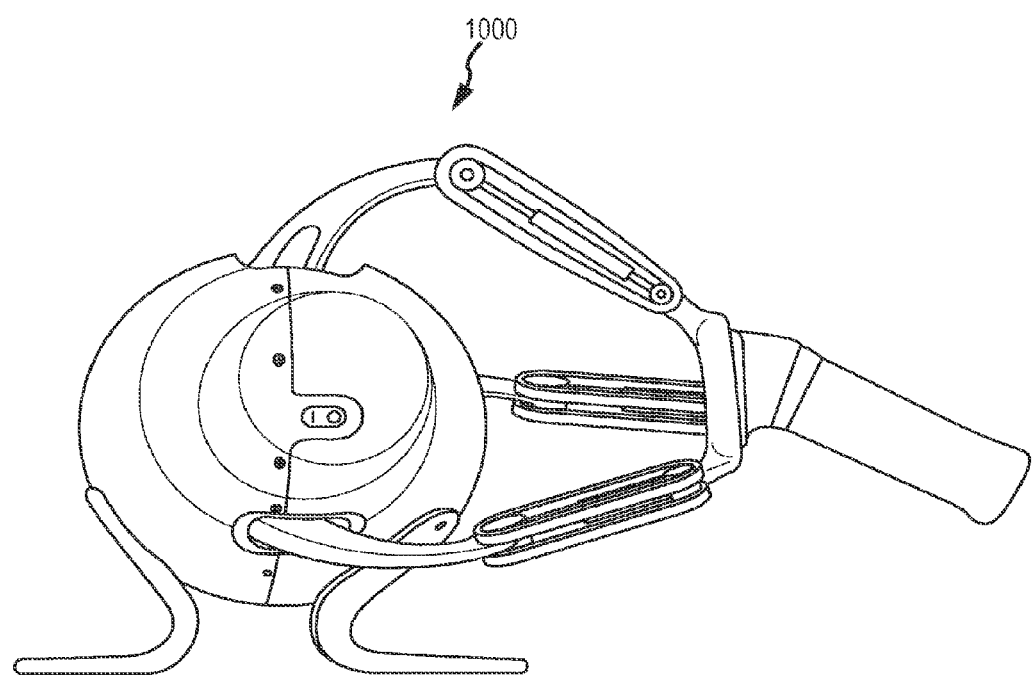
FIG. 17b is an exemplary three dimensional input device usable with a robotic catheter system.

As generally illustrated in FIGS. 17a, 17b, in an embodiment, the user input device 1000 may include a 2D or 3D input device, such as a mouse or 3D joystick. In another embodiment, the user input device 1000 may include a spatially detected glove or stylus as generally illustrated in FIGS. 18a-18b.

Figure 18A:
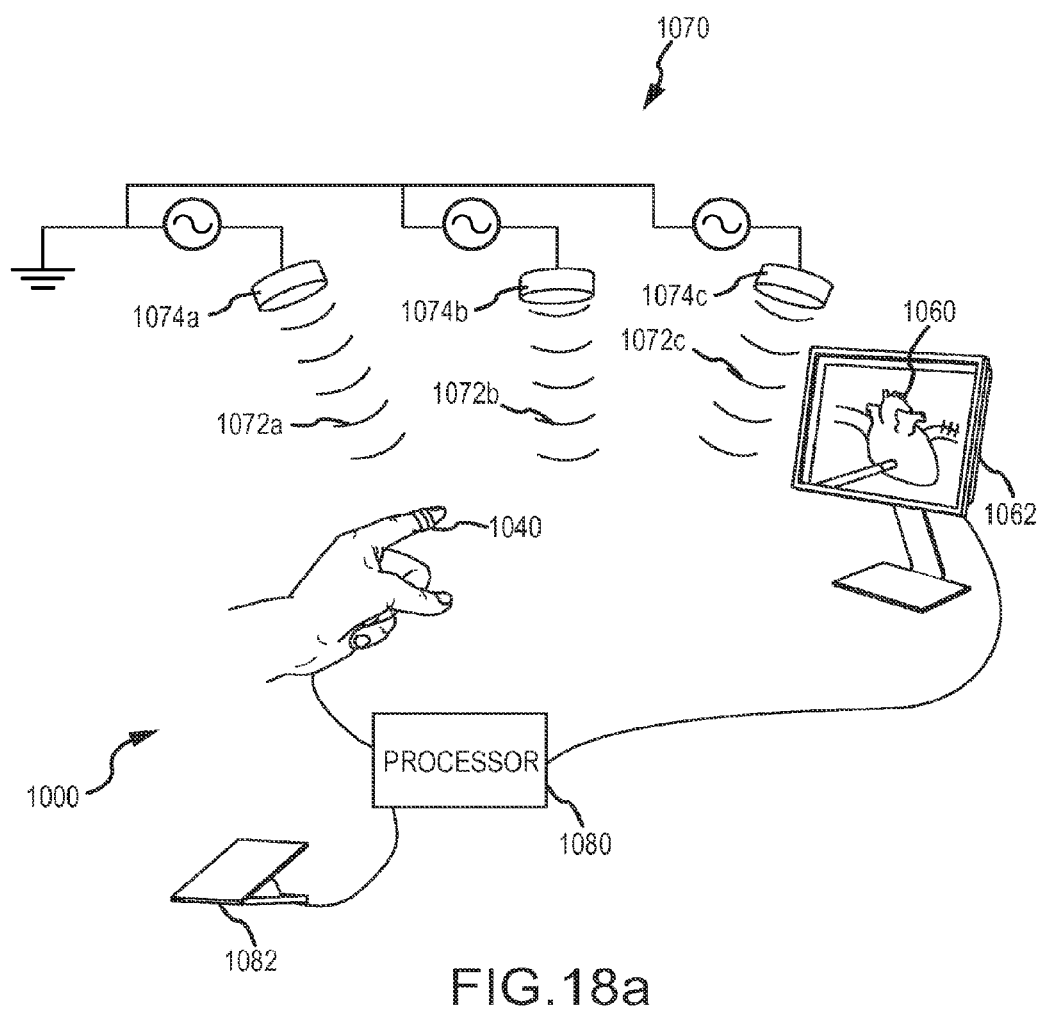
FIGS. 18a-18b are exemplary illustrations of a three dimensional input device usable with a robotic catheter system that employ non-contact position sensing.
Figure 18B:
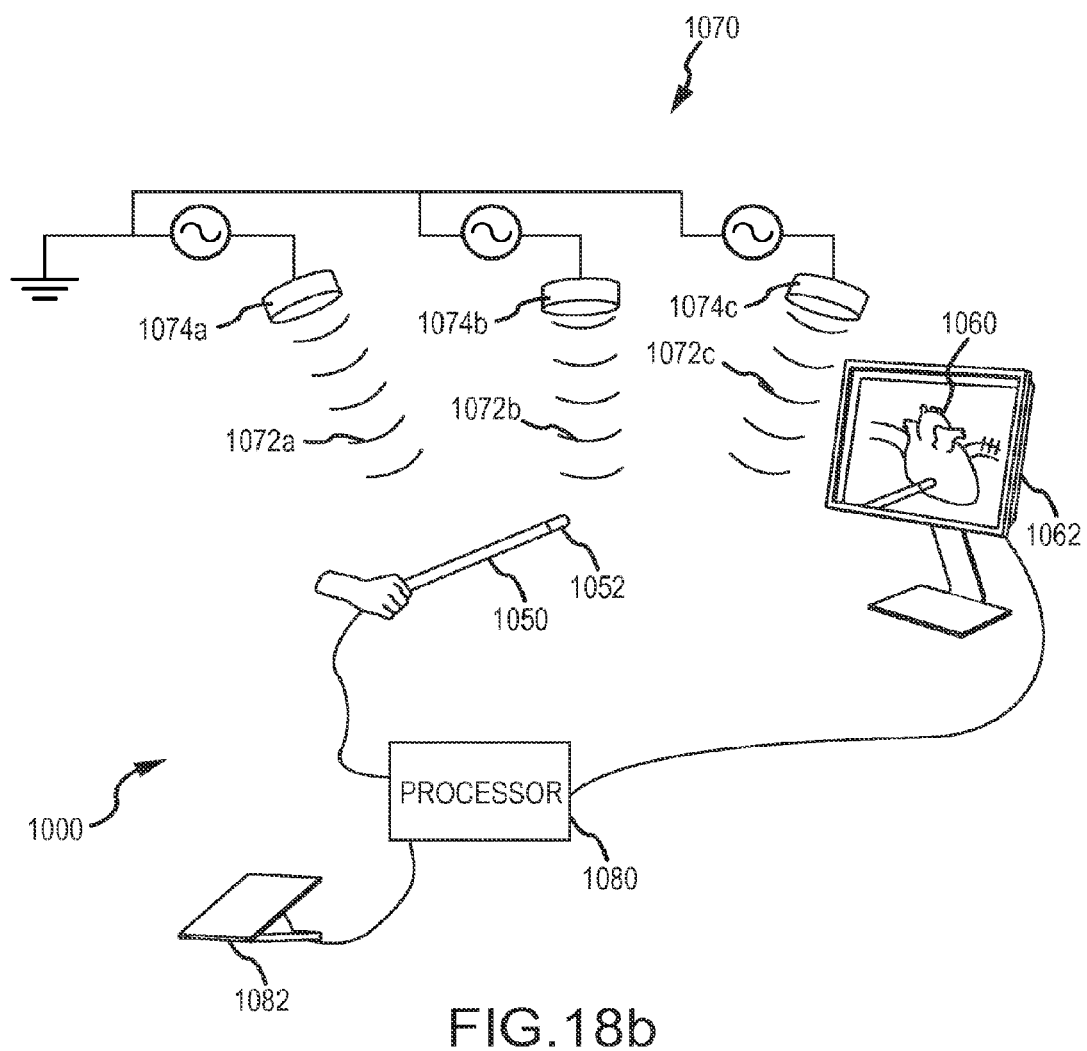

In an embodiment where the user input device 1000 includes a spatially detected glove, such as generally illustrated in FIG. 18a, the user's/wearer's index finger may be instrumented with various sensors 1040 (e.g., position and orientation sensors, and/or accelerometers). In this embodiment, the user may have the ability to manipulate the actual catheter tip by moving his/her instrumented finger. In another embodiment, as generally illustrated in FIG. 18b, a stylus 1050 may be substituted for the user's index finger, where the stylus 1050 is similarly instrumented with sensors 1052 configured to measure, for example, position, orientation, and/or acceleration.

In an embodiment, the user may be presented with a three dimensional visualization of the catheter and/or heart anatomy, such as through holographic imagery. Using the spatially detectable stylus or glove, the user may manipulate or interact with a visualization of the catheter, for instance, by moving the actual device within the holographic image. In such an embodiment, the real-time catheter position may be configured to track the three dimensional position of the user's index finger or stylus. Alternatively, as illustrated in FIGS. 18a-18b, the spatial positioning of the glove 1040 or stylus 1050 may be detected in three dimensional space and registered to a representation of a catheter or a target located within a model of the patient's anatomy 1060. The catheter representation within the model 1060 may be configured to be displayed to the user on a two-dimensional monitor 1062. By moving the instrumented finger or stylus, the user may control the movement of the catheter representation, which is in turn configured to control the movement of the actual catheter. Further, if desired, an incremental movement control scheme may be implemented by incorporating an activation switch, such as, for example, a foot pedal 1082. The actuation switch may indicate to the system that successive movements should be recorded or registered within the system for the purpose of control.

The glove or stylus input device may be locatable in 3-D space through the use of a positioning system employing a magnetic field, an electrostatic field, or through the use of an optical positioning system. These systems may include, for example, the EnSite NavX system from St. Jude Medical, the gMPS system from Mediguide, the CARTO system from Biosense Webster, the Aurora system from Northern Digital, or the RMT system from Boston Scientific.

In an embodiment, the positioning system may be implemented within a liquid tank (e.g., water tank), where field generators (such as those associated with the St. Jude Medical NavX™ control system) are externally attached. For such embodiments, an instrumented glove or stylus may extend into the tank while, for example, user's finger (e.g., index finger), or stylus may be instrumented with electrodes configured to measure parameters of the electric field. In an embodiment, the construction and/or placement of the sensors (e.g., NavX-type electrodes) may be similar to sensors on the distal portion of the catheter.

In another embodiment, the positioning system may be implemented using a magnetic positioning system. As generally illustrated in FIGS. 18a-18b, a magnetic positioning system 1070 may operate, for example, by emitting several magnetic fields 1072a-1074c from an array of field generators 1074a-1074c. Sensor coils (e.g., sensors 1040 or 1052) located on the glove or stylus may then sense the magnetic field strength emanating from each sensor coil. By selectively energizing each field generator at a different time or frequency, a processor 1080 may be able to resolve the sensor's position and orientation relative to each field generator or to a fixed reference sensor. Detected changes in the position and orientation of the glove or stylus sensor may then be registered and scaled by the system as a movement of a displayed catheter.

A user interface device in the form of a touch screen monitor will now be discussed with reference to FIGS. 19a-19d

An embodiment of user interface device may include a multi-touch display interface 1100 and related hardware and software that would allow a user to physically interact with the robotic catheter system without the need for a keyboard, mouse, or other input device. Such a display may be configured to recognize multiple finger or hand contacts with or along the screen, and would allow a user to directly interface with the objects, anatomy, or devices displayed on the screen.

Figure 19A:
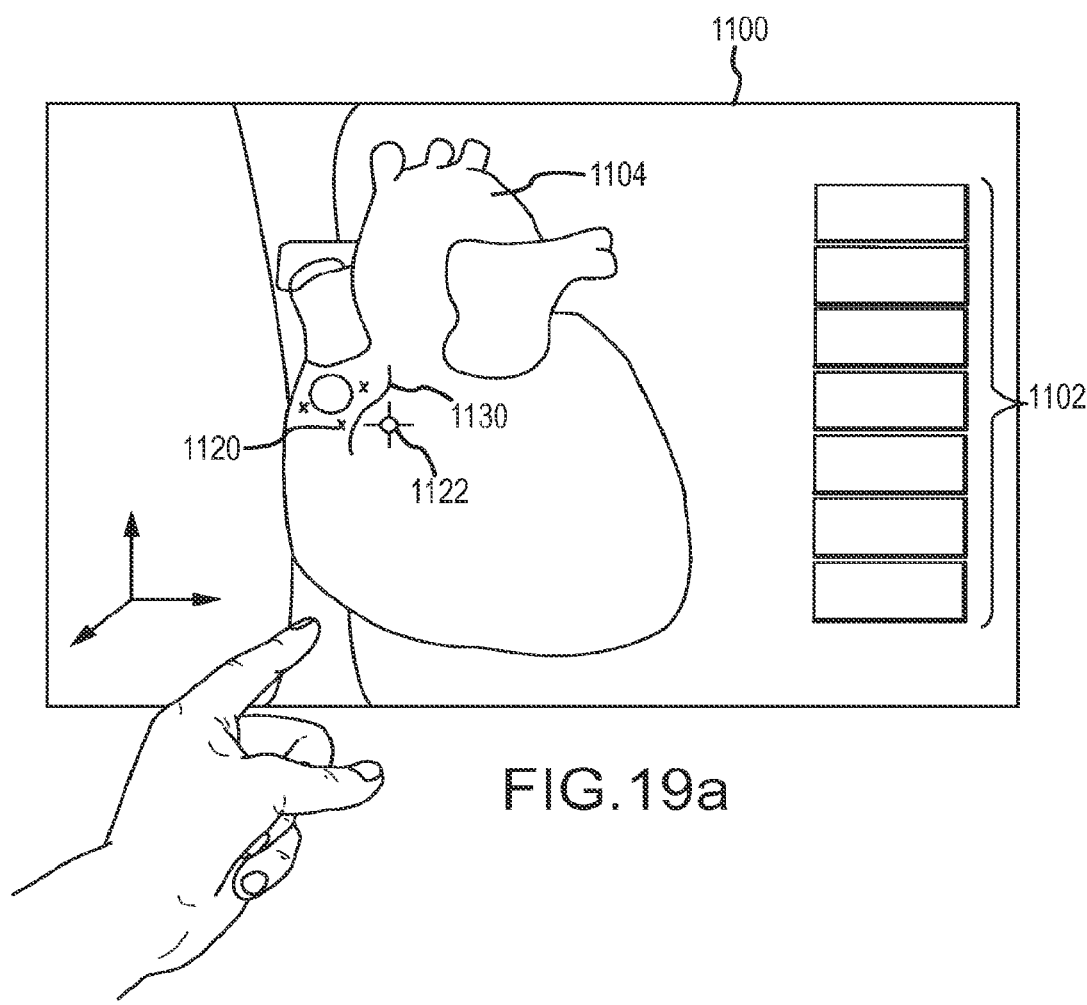
FIGS. 19a-19c are exemplary embodiments of a touch-sensitive input device usable with a robotic catheter system.
Figure 19B:
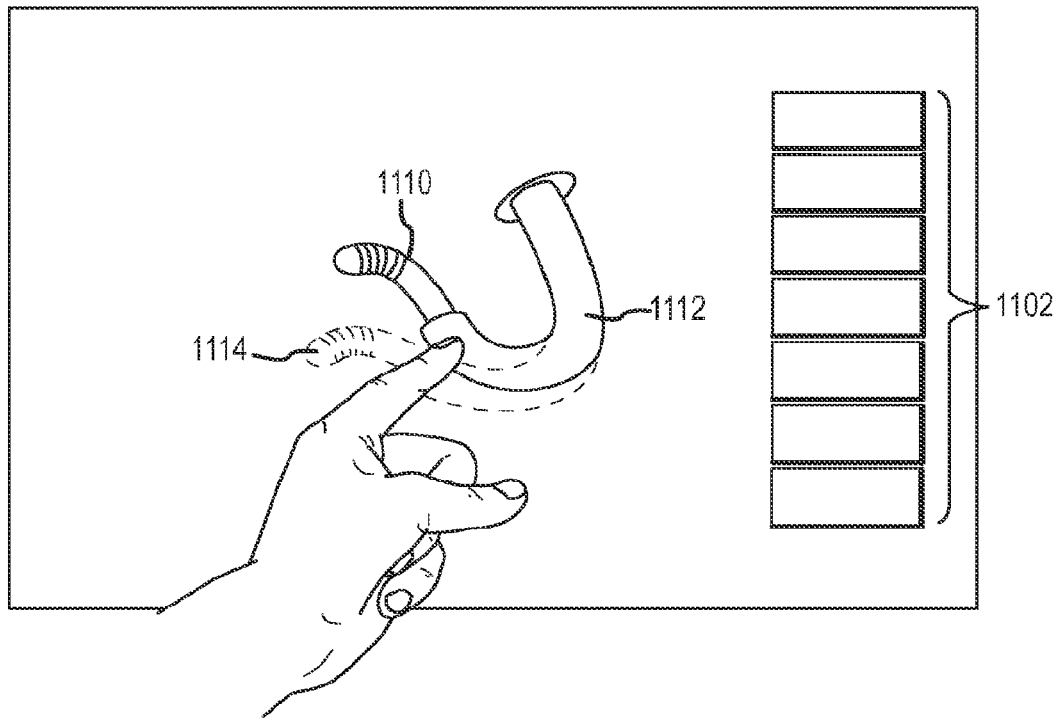

As shown in FIG. 19a-19b, an embodiment of the multi-touch interface 1100 may include multiple on-screen menu buttons 1102 that allow a user to toggle between various active functions within the image. Such functions may include, for example, the ability to pan, rotate, or zoom 3D objects and models within the display, select and/or direct movement of the catheter or sheath, place lesion markers, way points, virtual sensors, or automated movement targets and lines within the anatomic model.

In an exemplary approach, when in rotate mode, a user may rotate a 3D cardiac geometry 1104 by touching the screen with a finger and dragging across the screen to spin the 3D model about an axis orthogonal to both the surface normal of the screen and the direction of the dragging motion. When in pan mode, a dragging motion across the screen may physically move the model across the screen. Additionally, the zoom may be controlled, for example, through a pinching (zoom out) or expanding motion (zoom in) of multiple fingers, or through the use of an on-screen slider As shown in FIG. 19b, in an embodiment, the multi-touch interface 1100 may be used to control the movement of a displayed catheter 1110 or sheath 1112 by first pressing on the image of the catheter or sheath to select it, followed by dragging the selected device in the direction of intended travel. Alternatively, the catheter 1110 or sheath 1112 may be selected by using a pinching motion as if the user is virtually grabbing the image. In an embodiment, while the user is dragging a virtual representation of the catheter or sheath, a ghost image 1114 of the current position of the device may be displayed as a reference. The ghost image 1114 may be based on real-time feedback of the actual catheter position as provided by a catheter positioning system such as Ensite NavX. Once the user is satisfied with the movement, the user may release the selected catheter or sheath by removing his/her finger from the screen. The system may then be configured to move the actual catheter in accordance with the user intended motion, and may update the ghost image 1114 to reflect the actual movement. In another embodiment, the user may move a control point on the catheter or sheath and the actual catheter may be configured to track this point in real-time.

Figure 19C:
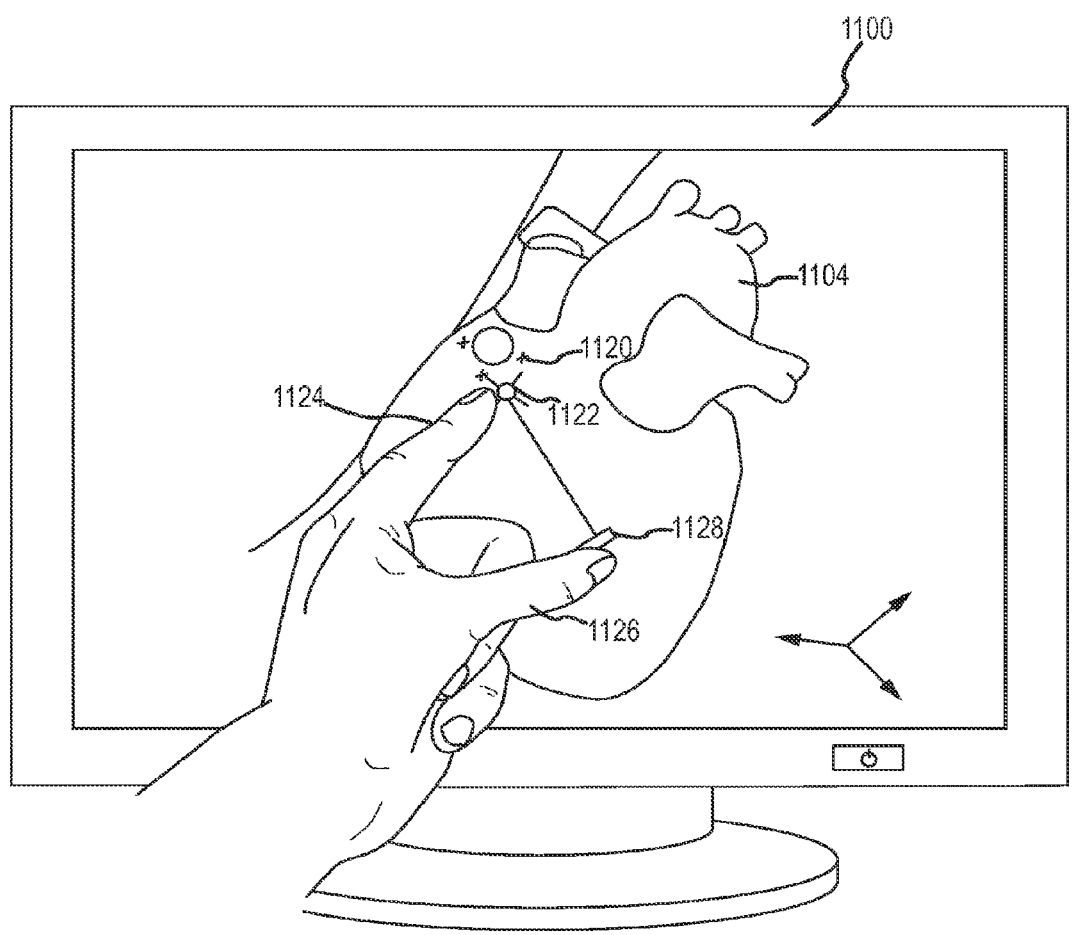

In an embodiment, as generally illustrated in FIG. 19a, 19c, the user may use the multi-touch interface 1100 to select target points 1120 within the image. These target points may be used to identify lesion points for intended or completed therapy delivery, way-points for semi-automated step-wise catheter movement, destination points for fully automated movement, or as relative markers or virtual electrophysiology sensors that may have no impact on relative movement. In an embodiment, a target point may 1120 be initially set by taping on screen in a position where a target point is desired. Once a point has been set, it may be subsequently selected by re-tapping on the point. When a point is "selected," it may change appearance, such as selected point 1122. If the user desires to move target point, the user may for example, select it by tapping it, and then drag the point to a new location. Additionally, after selecting a point, the software may call up a list of menu options that may allow the user to configure or view one or more parameters of the point. Such parameters may include, for example, the nature of the point (e.g. marker, lesion point, waypoint, sensor) the distance of the point above the surface, or specific data recorded or computed at the point.

Once a user taps the screen in the desired location of the target point, the software may be configured to place the target point 1120 directly on the surface of the model 1104 as displayed. In such a configuration, the system may know the relative depth of each pixel or primitive on the display. By touching on a displayed element, the system may map the target point directly to the anatomical surface. The software may further allow the user to specify a fixed or minimum distance from the displayed anatomical surface where the point should be located. For example, if the user specifies a distance of 10 mm prior to selecting a point, the software may locate the target point 10 mm off of the selected surface in a direction normal to the screen/viewing plane. Alternatively, the software may generate a virtual surface located 10 mm interior to the surface of the anatomical model and then map the point to the virtual surface. (i.e. 10 mm normal to the anatomical model surface). In another embodiment, as shown in FIG. 19c, the user may select a point 1122 with one finger 1124, and use a second finger 1126 to control a variable slider 1128 to specify a distance above the surface. The slider 1128 may likewise be located on the side of the screen and/or may appear only after a point has been selected. The display may also be configured to display a secondary projection of the catheter and model to aid the user in positioning the target point in three dimensional space (e.g. using a right anterior oblique (RAO) projection as the primary display, and a left anterior oblique (LAO) projection as the secondary display).

Referring back to FIG. 19b, in an embodiment, as the user is dragging a display of the catheter 1110 (or sheath 1112), the user may use a second finger to modulate a slider (such as a slider generally illustrated in FIG. 19c) to control the catheter's distance from the anatomical surface in real time. Using this technique, the user could achieve a motion where, for example, the catheter begins in contact with the tissue, gradually lifts off from the tissue while traversing a distance, and gradually lands back on the tissue. Alternatively, for either free catheter motion, or for positioning a target point, the user may use a physical slider or wheel, apart from the display, to modulate the distance from the surface. Using the touch screen, the user may also control the extension of the catheter from the sheath by placing one finger on the catheter 1112 and a second finger on the sheath 1114 and expanding or squeezing his/her fingers together.

In addition to setting individual target points, as illustrated in FIG. 19a, the user may also be able to specify a line or path 1130 along the surface of the model 1104 by touching and dragging a finger across the screen. Such generated line 1130 may be similar to a splined series of waypoints. Furthermore, in an embodiment, the user may select a point along the line and "lift" that point away from the surface by, for example, using a slider or numerical input. Points adjacent to the selected point may additionally be lifted off as if they were tied to the selected point.

Figure 19D:
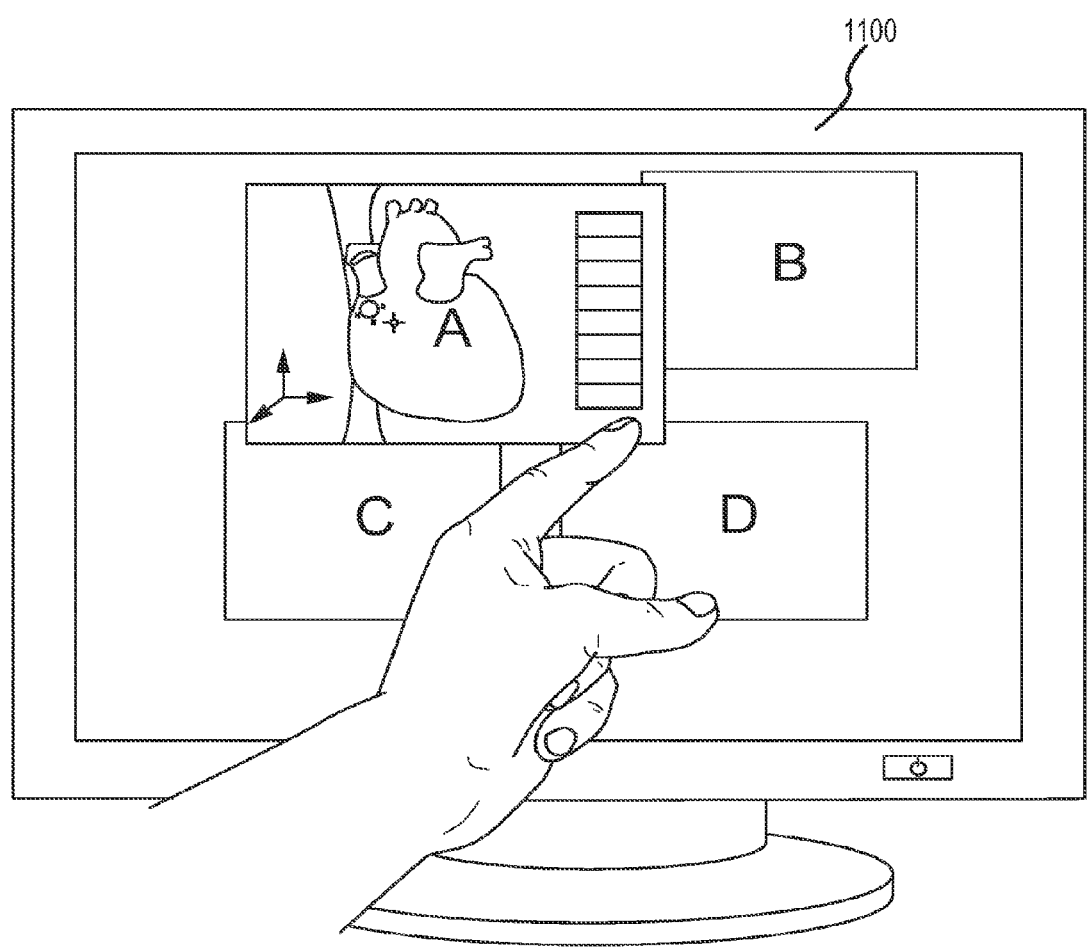
FIG. 19d is an embodiment of a touch-sensitive input device used to manage multiple displays.

In an embodiment, as shown in FIG. 19d, the multi-touch interface 1100 may be used to manage multiple displays (such as displays A-D) in an integrated electrophysiology environment. Using the interface for display management purposes may include the ability to resize, move, minimize, or maximize windows that display, for example, EnSite NavX models, digital fluoroscopic displays, patient vital information, patient hospital records, real time electrocardiograph traces, CT imagery, MRI imagery, and/or any other displays desired by the user. In an embodiment, a user may move or expand a window using on-screen buttons to, for example, freeze the touch screen input for the respective displays, followed by touching and dragging the window to move it, or using a multi-finger expanding motion to, for example, expand the window.

In another embodiment, the user input may be obtained through a spatial operating environment that is configured to monitor hand or body gestures without any required direct contact with a screen or device. The interface may operate together with either a two dimensional display or a three dimensional holographic image, and may allow the user to selectively manipulate, for example, the catheter or sheath, the cardiac model, various markers or waypoints within the model, or the positioning of other informational windows or displays. Such a gestural interface may include, for example the "G-Speak" Spatial Operating Environment, developed by Oblong Industries, Inc.

Haptic feedback based on actual sensed forces on a distal catheter tip will now be discussed.

An embodiment of user interface device 1000 that incorporates movement of a physical input device may include touch-type feedback, often referred to as "haptic feedback" This type of feedback may involve forces generated by a motor connected to user interface device 1000 that the user can feel while holding the device. These forces may be based on actual or computed forces being applied to a physical catheter tip. In an embodiment, the unit may sense forces using a force and/or impedance sensor in the tip of the catheter and generate a corresponding force on an input handle. In other embodiments, the forces can be based on a computed geometric model of the cardiac anatomy, such as that associated with the St. Jude Medical, Inc. EnSite™ system.

In an embodiment, haptic feedback may be conveyed to a user by employing an input device instrumented with motors/encoders on each degree of freedom. Though the motors may operate in a passive mode for a majority of the procedure, if feedback is required by the system, the motors may be energized to produce a torque on the input controls capable of retarding the user's movement in particular degrees of freedom. While in a passive mode, the motor typically will not produce a significant retarding force, however the attached encoder may record the input for use in visualization and control routines.

Prior to a haptic response being conveyed, the system may first calculate the appropriateness and magnitude of such a force. In an embodiment, such a force may attempt to replicate a contact between an actual catheter tip and a portion of the cardiac anatomy. In an embodiment, such contact may be either directly sensed through one or more force sensors on the distal tip of the catheter/sheath, or may be calculated based on a virtual catheter/sheath position within a rendered geometric computer model.

In an embodiment where haptic forces are based on actual catheter contact, the catheter's distal tip may be instrumented with a force sensor configured to provide an indication when physical contact is detected. Such a force sensor may include, without limitation, load cells, shape memory alloy based force sensors, piezoelectric force sensors, strain gauges, or optical-based or acoustic-based force sensors. One example of a contact sensor that may be used is described in detail in U.S. patent application Ser. No. 11/941,093 entitled "Optic-Based Contact Sensing Assembly and System," which is incorporated by reference in its entirety. In other embodiments, a contact or proximity sensor may be used, such as those associated with detected electrical impedance. One example of a proximity sensor that may be used is described in detail in U.S. patent application Ser. No. 12/465,337, entitled "System and Method for Assessing the Proximity of an Electrode to Tissue in a Body," which is incorporated by reference in its entirety.

In an embodiment employing actual contact sensing, the sensor may generate a signal representative of the actual physical or electrical contact. Based on the magnitude and direction of the sensed force, as well as the current position of the input device, the system may produce a corresponding torque or force on the input device that may resist further movement through the obstructing anatomy. The system can be configured so that the user would feel this reaction force as if the input device was impacting a "virtual wall."

Based on the system calibration, the resistive force the user feels at the input joystick could be more or less "spongy." That is, the system could be tuned so that a tip impact with the cardiac wall is either felt like a rigid impact with an immovable object, or perhaps as a contact with a soft sponge.

Haptic feedback based on virtual catheter tip proximity to virtual cardiac anatomy will now be discussed.

As discussed above, in an embodiment, haptic feedback forces may be conveyed to a user based on contact forces computed from the proximity between a virtual catheter model and a computer-generated representation of the cardiac anatomy. In an embodiment, the positioning of the virtual catheter model may be obtained through an impedance-based position detection system (e.g., such as associated with St. Jude Medical's NavX™ system), or through a magnetic-based position detection system (e.g., such as associated with Mediguide's gMPS positioning system). Further such a computer-generated representation of the cardiac anatomy may be derived from prior CT or MRI data, or a model (such as that created or maintained by St. Jude Medical's EnSite™ system).

With such embodiments/configurations, a user may have a previously obtained geometric model of the cardiac anatomy. This model may be visible to an electrophysiologist user through a visualization system (such as St. Jude Medical's EnSite™ system). This model may be assembled using, for example, previously captured CT or MRI images, and/or "skinned" geometry obtained by sensing actual position data of a mapping catheter (e.g., with St Jude Medical's NavX™ system or the gMPS system). Once the model is assembled, a catheter locating system (e.g., St. Jude Medical's NavX™ System or the gMPS system) could then place the working catheter inside the computed geometric model. In an embodiment, as the catheter is moved within the geometry, a haptic system could be used to compare the positioning of the catheter to that of the generated geometry. If the catheter is perceived to be in contact with the generated geometry, a resistive force could then be generated in connection with the associated input device—e.g., using attached motors.

In an embodiment, the geometric model may be registered to a repeating physiological signal such as, for example, the cardiac rhythm or respiration rhythm. As this signal is sensed in the actual procedure, the model geometry may dynamically change. This may then enable computed haptic feedback to provide a more accurate representation of the contact actually occurring within the patient.

A displayed orientation vector within the visualization software to show direction of planar, thumb switch deflection will now be discussed.

With some traditional, non-robotic catheter procedures, a thumb switch on the catheter handle causes catheter deflection by tensioning a corresponding steering wire. Such a switch typically allows the distal tip of a catheter to laterally deflect in one of two opposing directions in a single plane. If deflection is desired in more than one plane, a user commonly must physically rotate the catheter about its longitudinal axis to cause the deflection plane to rotate.

In an embodiment of robotic catheter system 10 incorporating instrumented traditional catheter handle input controls, as described above, an indicator may be provided within a computer visualization to give the user an idea of which direction the distal tip will deflect if the deflection thumb switch is actuated. In an embodiment, such a representation (e.g., deflection plane vector) may include an arrow superimposed near the tip of the virtual representation of a physical catheter. Such an arrow may indicate the direction the catheter would move if the thumb switch were pulled toward the user. Similarly, pushing a control (e.g., thumb switch) may cause the catheter to deflect in the opposite, arrow tail direction. The user may then cause a rotation of this vector by rotating an input handle, which may then be sensed by the attached motor/encoder or potentiometer. Similarly, a deflection vector could be associated with sheath visualization.

The general mechanics of the catheter and sheath movement will now be described with reference to FIGS. 20-22

Figure 20:
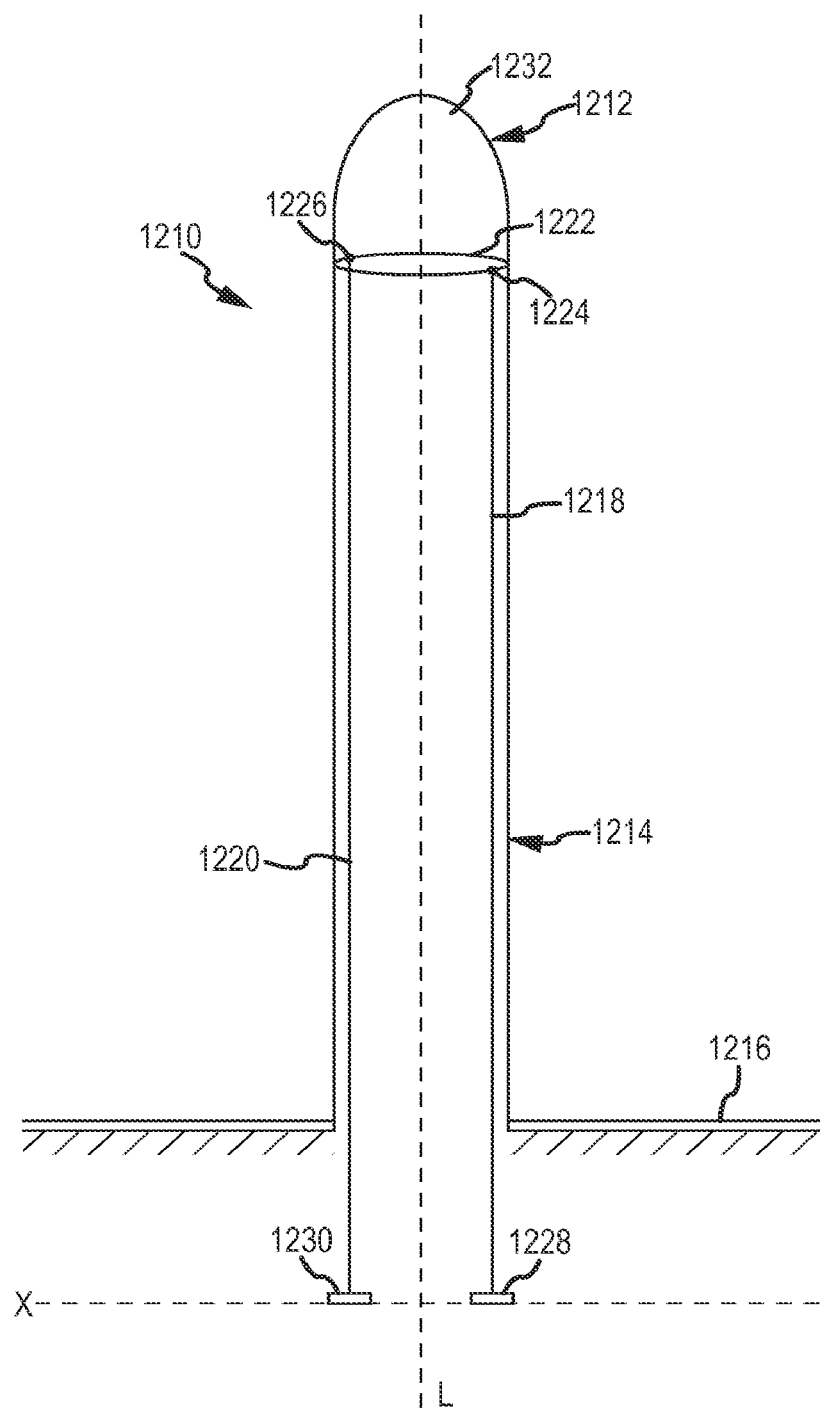
FIG. 20 is a general representation of a catheter according to an embodiment of the invention, shown in an undeflected state.

As generally illustrated in FIG. 20, the catheter 1210 may include at least two steering wires 1218, 1220, each longitudinally situated within and along a substantial length of the catheter 1210. In an embodiment, the steering wires 1218, 1220 may be comprised of a material having a high elastic modulus—such as, for example, steel or aluminum. The catheter 1210 may further include a pull ring 1222, which may take the form of a rigid ring firmly connected or affixed within a portion of the distal portion 1212 of the catheter 1210. Each steering wire may be rigidly connected to pull ring 1222, for example, via a rigid connection or coupling 1224, 1226. In an embodiment, such a rigid connection or coupling may comprise a weld, braze, or other known means of attachment.

As generally depicted in the illustrated embodiment, proximal portions of the steering wires 1218, 1220 may be respectively connected to control members 1228, 1230. Control members 1228, 1230 may be, for example, slider blocks such as those mentioned above, and may be used to interface or operatively connect control devices, such as the fingers of the manipulator assembly, to the steering wires 1218, 1220. For illustrative purposes, as generally shown in FIG. 20, when catheter 1210 is configured in an undeflected state on longitudinal axis L, control members 1228, 1230 may both be situated at a one or more initial or common reference levels or datum (e.g., common datum X shown in FIG. 20). However, for some embodiments, no initial relationship of control members 1228, 1230 is necessary, and the positioning of each may, for instance, simply be a consequence of initial assembly.

Figure 21:
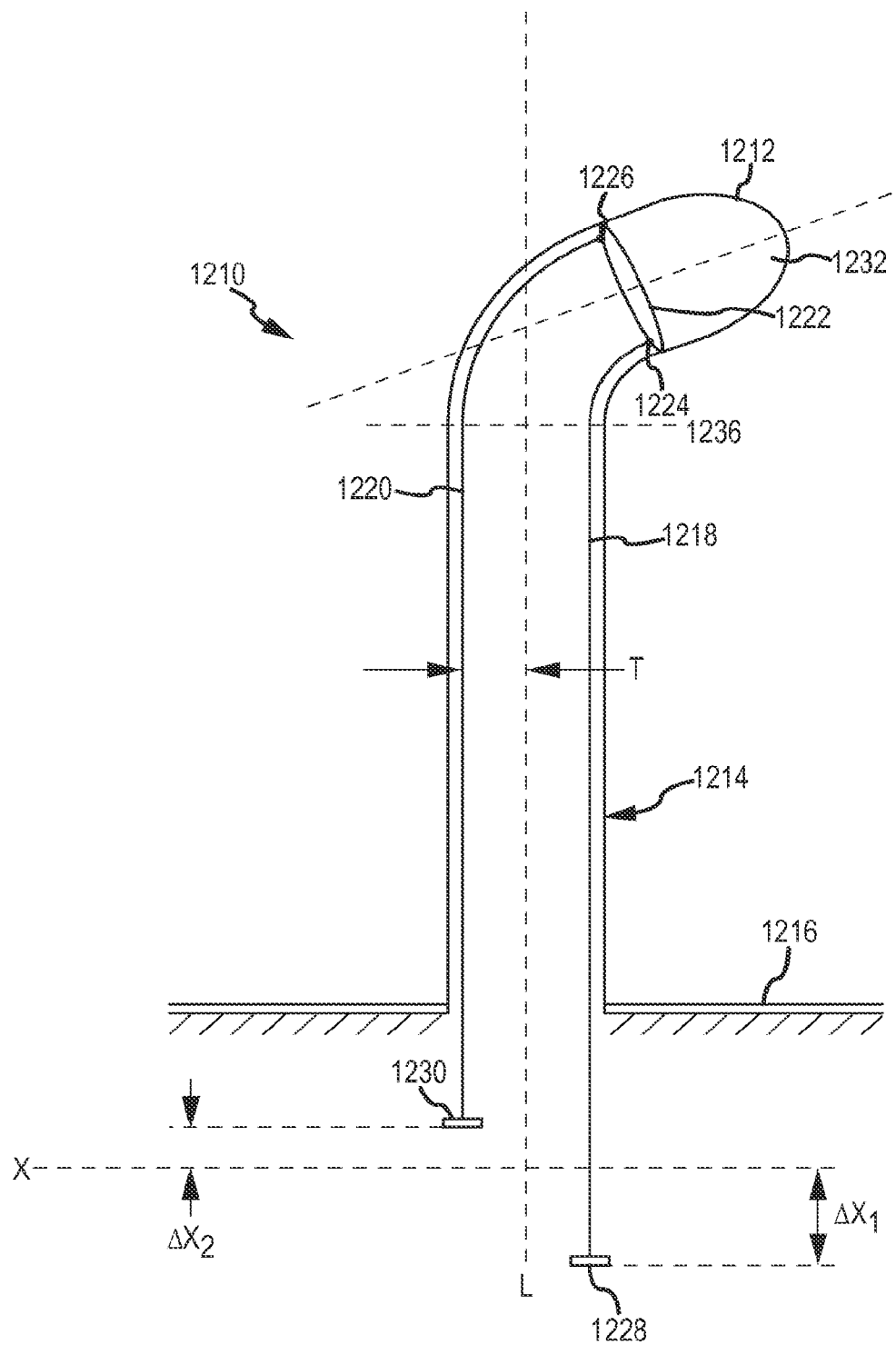
FIG. 21 is a general representation of a catheter of the type illustrated in FIG. 20, shown in a deflected state.

As generally shown in FIG. 21, the distal portion 1212 of catheter 1210 may be deflected or displaced away from longitudinal axis L by selective actuation or tensioning of one or more steering wires. For example, as generally illustrated in FIG. 21, control member 1228 may be translated in a proximal direction a distance $\Delta X_1$, which causes a tension response in steering wire 1218. The actuation of steering wire 1218 causes a corresponding deflection of the bendable section (i.e. the portion of catheter 1210 between fulcrum point 1236 and pull ring 1222) in a direction toward steering wire 1218. In the illustrated embodiment, the fulcrum 1236 generally defines the point along the length of the catheter at which the catheter 1210 transitions from a stiffer, proximal portion, to a more bendable, distal portion. In an embodiment, such increased bendability may be caused by using a material of a lesser durometer in the distal portion than in the proximal portion of the catheter. Alternatively, the fulcrum point 1236 may define a transition point of the catheter where the internal structure of the catheter is modified in a manner known in the art to promote distal bending.

As further illustrated in FIG. 21, while control member 1228 is actively deflected a distance $\Delta X_1$ in a first proximal direction, control member 1230 reactively moves or retracts a distance $\Delta X_2$ in a second, substantially opposing distal direction. The reactive motion of control member 1230 and steering wire 1220 may depend on the difference in arc lengths between the two steering wires within the bendable section of the catheter. Assuming the distal portion bends with a constant radius of curvature, the arc lengths of the steering wires would then be a function of a transverse distance—e.g., distance T between steering wire 1218 and the central longitudinal axis L—and the bending radius of curvature of the distal portion 1212. While, theoretically, displacements $\Delta X_1$ and $\Delta X_2$ can bear a linear relationship to each other, non-uniform axial compression of catheter 10 can cause the relationship between $\Delta X_1$ and $\Delta X_2$ to be non-linear.

To cause catheter 1210 to move or retract back to an undeflected state along longitudinal axis L, a user could, for example, actively translate control member 1230 in a proximal direction. Such a motion could cause the distal portion 1212 to rotate and deflect toward steering wire 1220, while control member 1228 would be reactively translated in a distal direction. In an embodiment, due to memory effects of catheter 1210, such as caused by plastic deformation, upon restoring catheter 1210 to an undeflected state along longitudinal axis L, control members 1228, 1230 may not necessarily return to their original positions (e.g., on datum X).

It is noted that while FIGS. 20-21 illustrate the operation of a catheter having two steering wires oriented in a planar configuration, other embodiments may include three or more steering wires that may cause three dimensional motion of the distal portion of the catheter. FIG. 22 generally shows an axial cross-section of a catheter embodiment, taken at the fulcrum point, that includes four steering wires 1240a, 1240b, 1240c, 1240d. While this illustration displays all steering wires spaced approximately 90 degrees apart, various other configurations may be provided.

Figure 22:
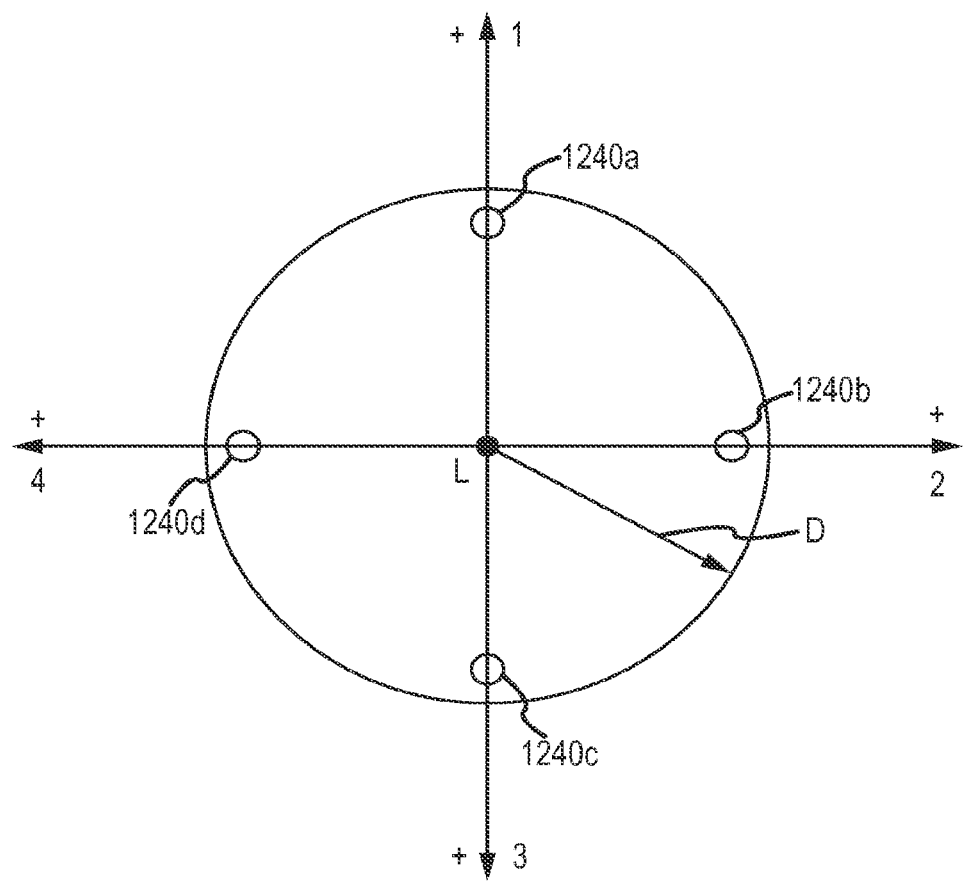
FIG. 22 is a graph of catheter deflection as a function of steering wire tension.

As generally illustrated in FIG. 22, the respective tensioning of adjacent steering wires may cause a deflection of the distal portion 1212 of catheter 1210 in a unique direction, e.g., direction D. Through selective actuation of pairs of steering wires, the distal portion of the catheter can be made to traverse circles of varying radii about longitudinal axis L (as viewed transverse to the page). The embodiment illustrated in FIG. 22 is similar to the two-steering wire embodiments shown in FIGS. 20-21, since, when any wire or wires are actively tensioned, the opposing wires is permitted to reactively move a distance in an opposing distal direction. For example, as shown in FIG. 22, to cause a distal motion in direction D, steering wires 2 and 3 (1240b, 1240c) may be positively tensioned, while steering wires 1 and 4 (1240a, 1240d) would move reactively.

Figure 23A:
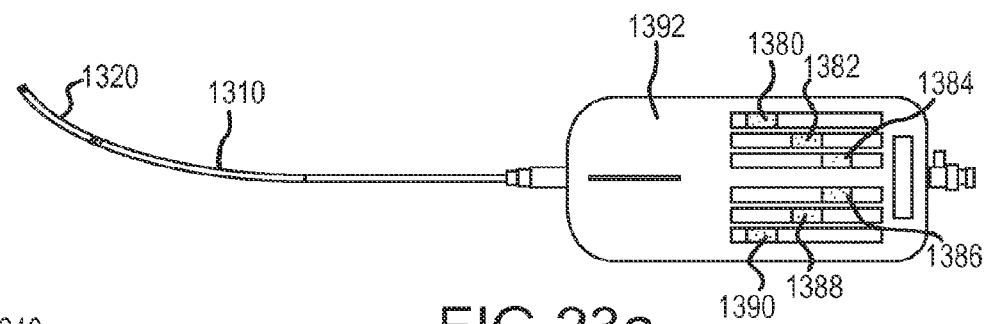
FIGS. 23a-23d are illustrations of a robotic catheter device cartridge employing multiple deflection zones.
Figure 23B:
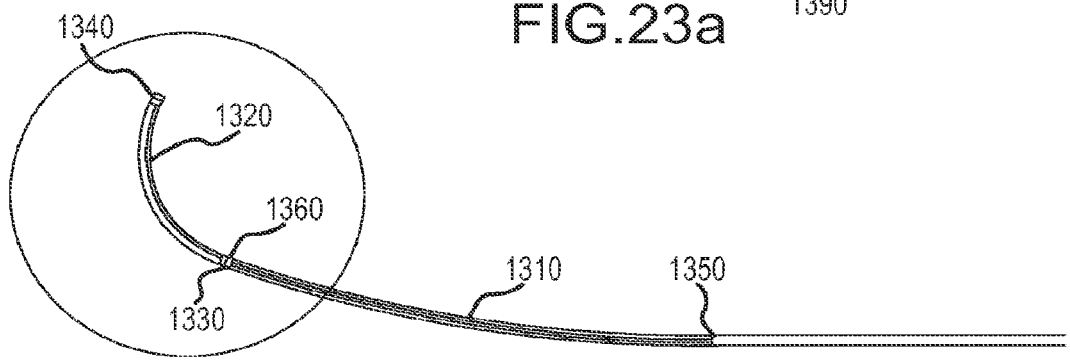
Figure 23C:
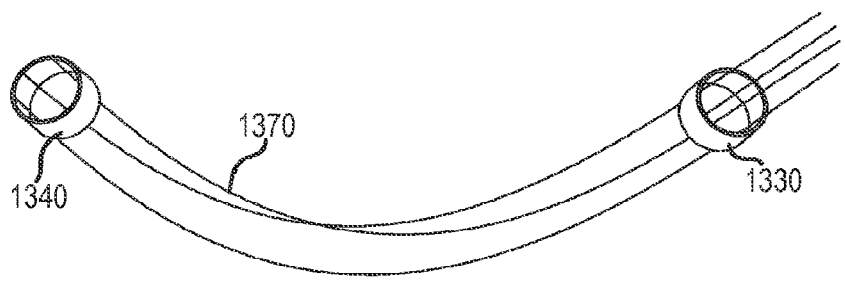

In an embodiment, as illustrated in FIGS. 23a-23c, the catheter may include multiple bendable sections (e.g., sections 1310, 1320), each having a separate pull ring (e.g., pull rings 1330, 1340), fulcrum point (e.g., fulcrum points 1350, 1360), and associated steering wires coupled with each pull ring. The inclusion of multiple bendable sections may allow a user to achieve compound bending postures with only a single device. In an embodiment, the catheter may include a first bendable section 1310 and second bendable section 1320 that are capable of independently directed bending motions. In other embodiments, the catheter may include three or more bendable sections.

In the embodiment illustrated by FIGS. 23b-23c, each bendable sections has a proximal fulcrum point 1350, 1360, a pull ring 1330, 1340 located distal to the fulcrum point, and a set of steering wires attached to the pull ring. The steering wires for both sections extend from the proximal end of the catheter, through the body of the catheter, and are affixed to the respective pull rings, as shown in FIG. 23c. In an embodiment, the fulcrum point for the second bendable section may be located at the pull ring for the first bendable section, as shown in FIG. 23c. In another embodiment, the fulcrum point may be located distal to the first pull ring.

Figure 23D:
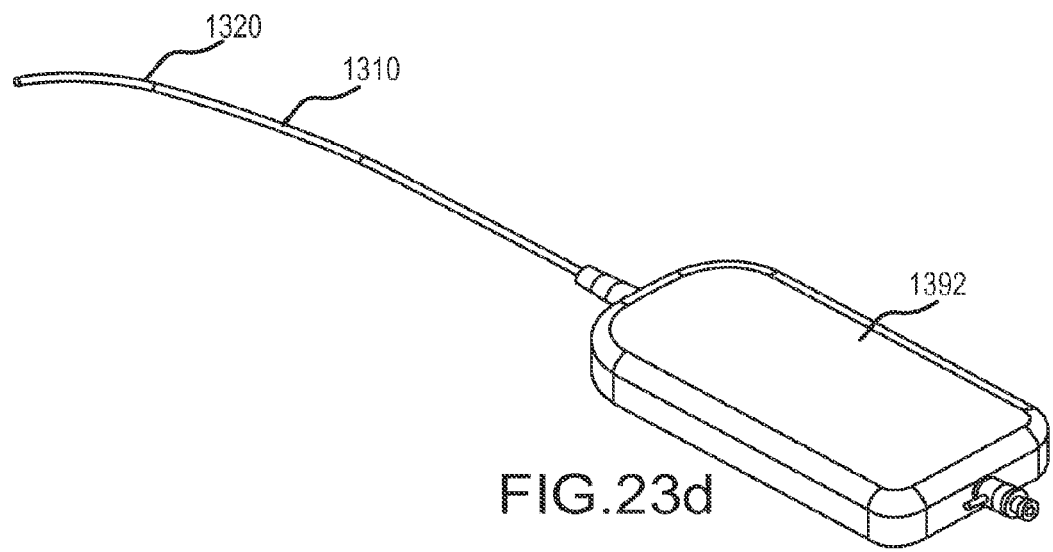
Figure 23E:
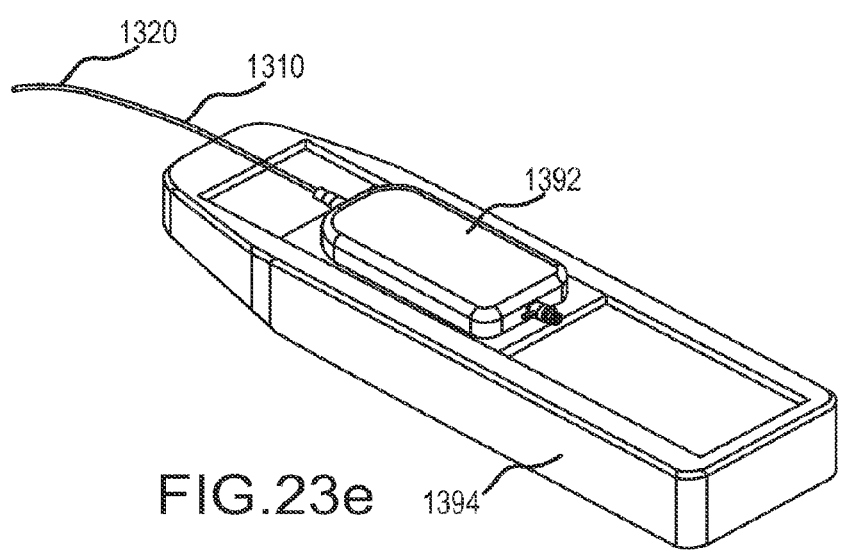
FIG. 23e is an isometric view of an embodiment of a robotic catheter device cartridge having multiple deflection zones coupled with an embodiment of a robotic catheter manipulator.

Similar to the cartridges described above with respect to FIGS. 5a-e, as shown in FIG. 23a each of the six steering wires may be coupled with a respective slider block (e.g., slider blocks 1380, 1382, 1384, 1386, 1388, 1390) within a proximal cartridge 1392. The cartridge 1392 may, in turn, be configured to interface with a robotic manipulator 1394, as shown, for example, in FIGS. 23a, 23d, 23e. While FIGS. 23a, 23d, 23e depict the multi-deflection zone catheter operating in a single cartridge system, it should be understood that the catheter may also be used in conjunction with a sheath cartridge as described above.

Active tensioning of "passive" steering wires will now be briefly discussed with reference to FIGS. 5a-5e (as discussed above) and 24-25.

Figure 24:
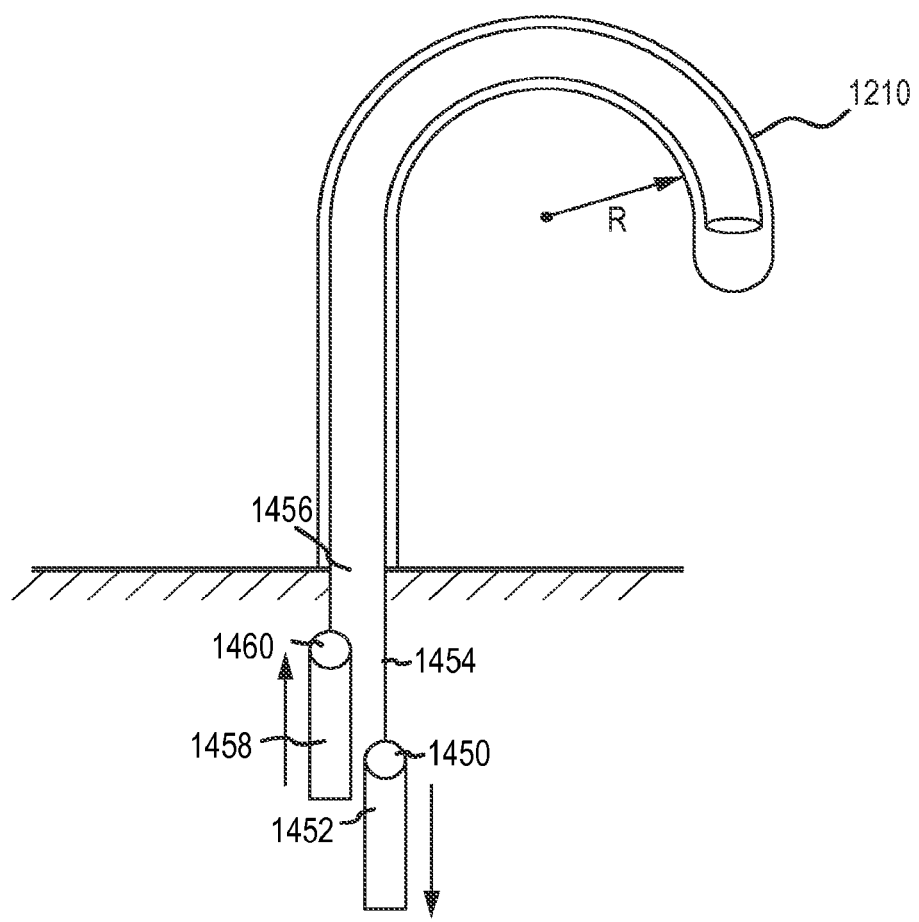
FIG. 24 is an exemplary view of steering wire movement for a two-wire catheter.

As described above, an embodiment of robotic catheter system 1210 may provide for tensioning of the steering wires (e.g., by moving fingers/slider blocks in a proximal direction). As generally shown in FIG. 24, active manipulator finger 1450 pushes slider block 1452 in a proximal direction. This motion causes the attached steering wire 1454 to tension, resulting in a distal deflection of the catheter tip. To allow the displacement, steering wire 1456 must move in a distal direction due, in part, to the radius of curvature R of the catheter bend. This causes the attached slider block 1458 to be pulled in a distal direction. In an embodiment, the manipulator fingers are not allowed to freely move due to their mechanical mounting (e.g., on a high-precision drive mechanism). To then allow the passive slider block 1458 to move distally, manipulator finger 1460 may be compelled to move in a distal direction.

Figure 25A:
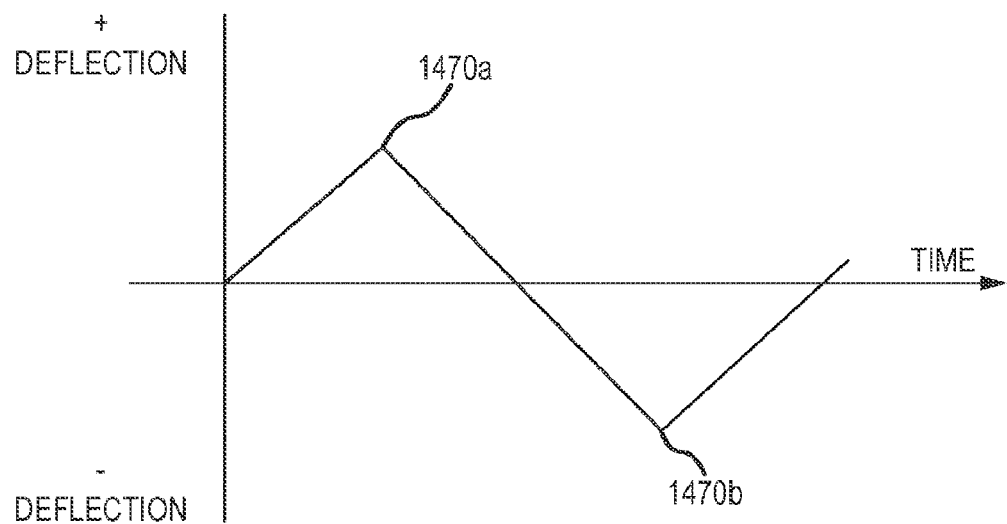
FIG. 25a is a graph that generally illustrates a dynamically responsive catheter motion.
Figure 25B:
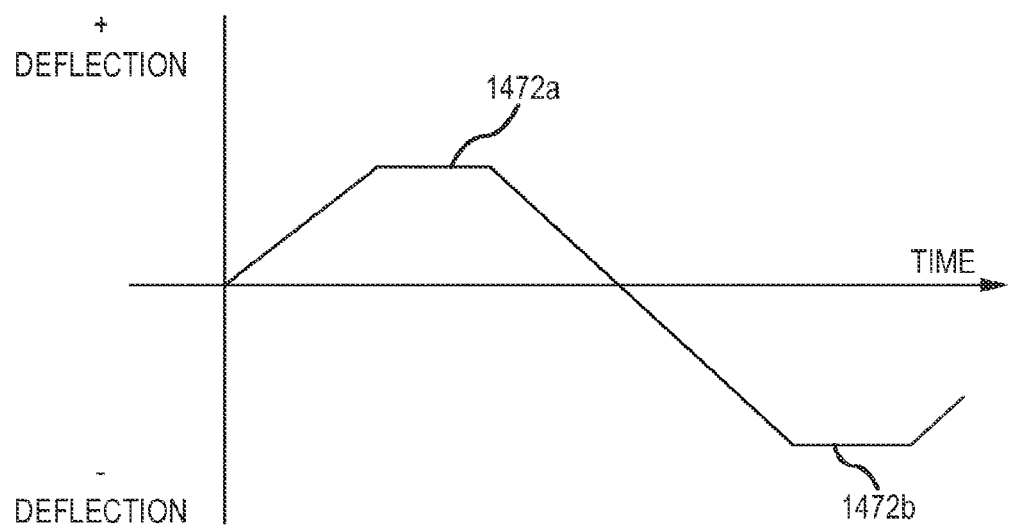
FIG. 25b is a graph that generally illustrates a catheter motion with transition latencies.

In an embodiment, to help prevent fingers 1460 from impeding passive steering wires 1456, each finger may be retracted to a "home" position when it is not controllably tensioning a steering wire. Such a return-to-home configuration can, at least in part, help ensure that each finger 1460 will not obstruct the distal motion of passive slider blocks 1458. It may be desirable, however, for such a configuration to include features to address issues associated with reduced system response time and potential step-wise distal tip motion, attributable to the time needed to move fingers 1460 back into contact with slider-blocks 1458 when the passive slider blocks must be tensioned to cause a desired movement. FIG. 25a includes a graph that generally illustrates a desirable, dynamically responsive catheter motion. This graph demonstrates a motion with sharp transitions 1470a, 1470b between active and reactive steering wires. In contrast, FIG. 25b illustrates a catheter motion that exhibits somewhat undesirable unresponsive states 1472a, 1472b, which may be occasioned by a need to re-tension reactive steering wires during a transition period.

It may be desirable, for example during a medical procedure, for the distal portion of a catheter to be capable of prompt dynamic, back and forth movements, such as those illustrated in FIG. 25a. To help facilitate such movement, it can be beneficial to maintain a minimal tension on all steering wires, even when such a steering wire may be reactively translating in a distal direction. Such a base or minimal tension can help ensure that no undesirable measure of slack is created in any steering wire that could potentially cause an unresponsive state (even if only momentarily) during a transition from a motion in one direction to motion in another direction. In an embodiment, passive slider blocks 1458 may be allowed to freely retract yet avoid contact latencies by incorporating a force sensor in mechanical communication each manipulator finger 1460. In such an embodiment, each passive finger 1460 may be controllably positioned such that a minimal contact force between finger 1460 and the passive steering wire slider block 1458 is always maintained. This ensures that all passive steering wires 1456 are maintained in a "ready" state yet are not significantly impeded. Such "active tensioning" may involve a closed loop algorithm that constantly monitors the force exerted on each finger 1460 through the use of, for example, strain gauges. The "active tensioning" control routine then may translate corresponding passive fingers 1460, by actuating a connected drive mechanism, to maintain contact force between finger 1460 and slider block 1458 within a bounded range (e.g., 50-100 grams of force).

Figure 26:
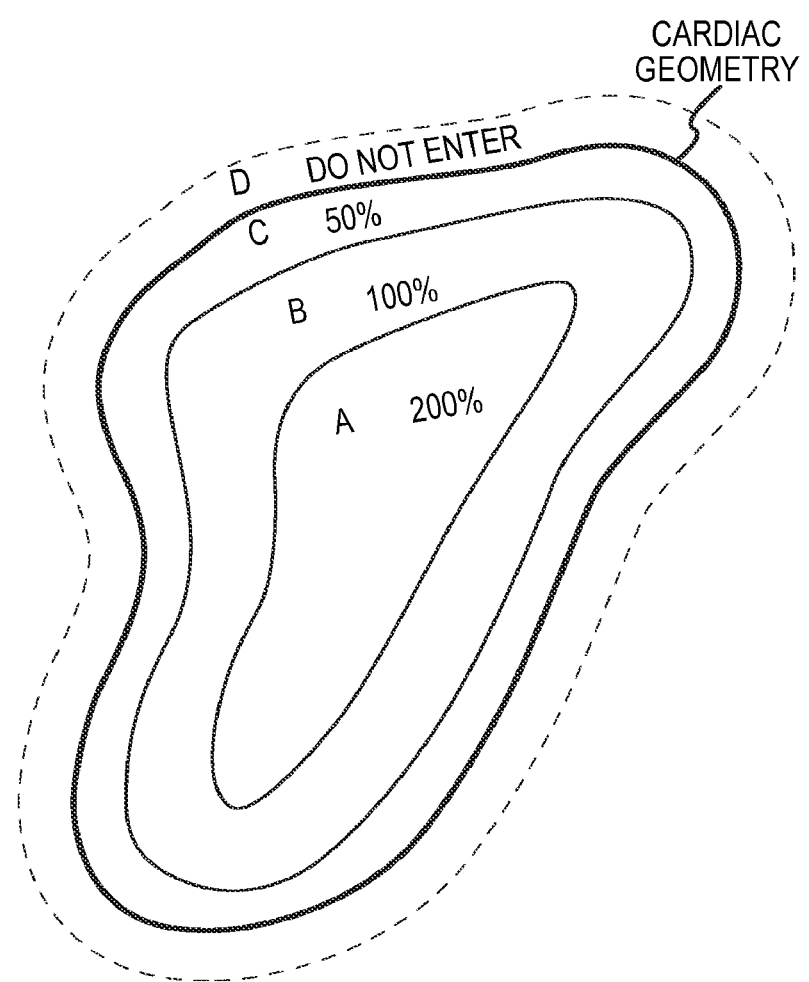
FIG. 26 is an exemplary view of speed-zones for optimizing movement of a catheter tip.

Pre-defined catheter "speed zones" will now be briefly discussed with reference to FIG. 26.

To aid users in navigating a catheter safely, yet quickly, around a cardiac chamber, robotic catheter system 10 may employ pre-defined "speed zones" to optimize the movement of the catheter tip. In an embodiment of the robotic catheter system, the user may have the ability to configure the maximum allowable catheter speed, or alternatively configures the scaling factor that relates the user input to the catheter motion, as a function of the orthogonal distance between the catheter and the nearest cardiac tissue. As described in relation to FIG. 26, zone A may be defined as the most central, and safest area in the cardiac chamber. In zone A, the catheter tip may be sped up so that the catheter tip can traverse this area at a faster than normal rate, e.g., 200% of the input motion. As the user moves the catheter closer to the cardiac wall, he/she may desire enhanced precision rather than speed. Therefore, zones B and C may purposefully and gradually reduce the scaling factor between input motion and tip movement. Finally, the user may have the ability to define a region exterior to the geometry, e.g., zone D, into which the catheter is prevented from entering. Alternatively, this "exterior zone" may be modeled to provide a force that would "push" the catheter back into the acceptable area.

If desired, the system may include a corresponding haptic response in the input joystick. For zones A, B, and C, such a haptic response may involve changing the dampening force on the handle (e.g., as the tip moves closer to the wall, the user might feel as if the tip is caught in an increasingly dense sludge). Once the tip starts to cross the barrier between zone C and zone D, this feeling may be accompanied by a force that prevents inadvertent continued motion.

User guided robotic control will now be discussed with reference to FIGS. 27-43.

Figure 27:
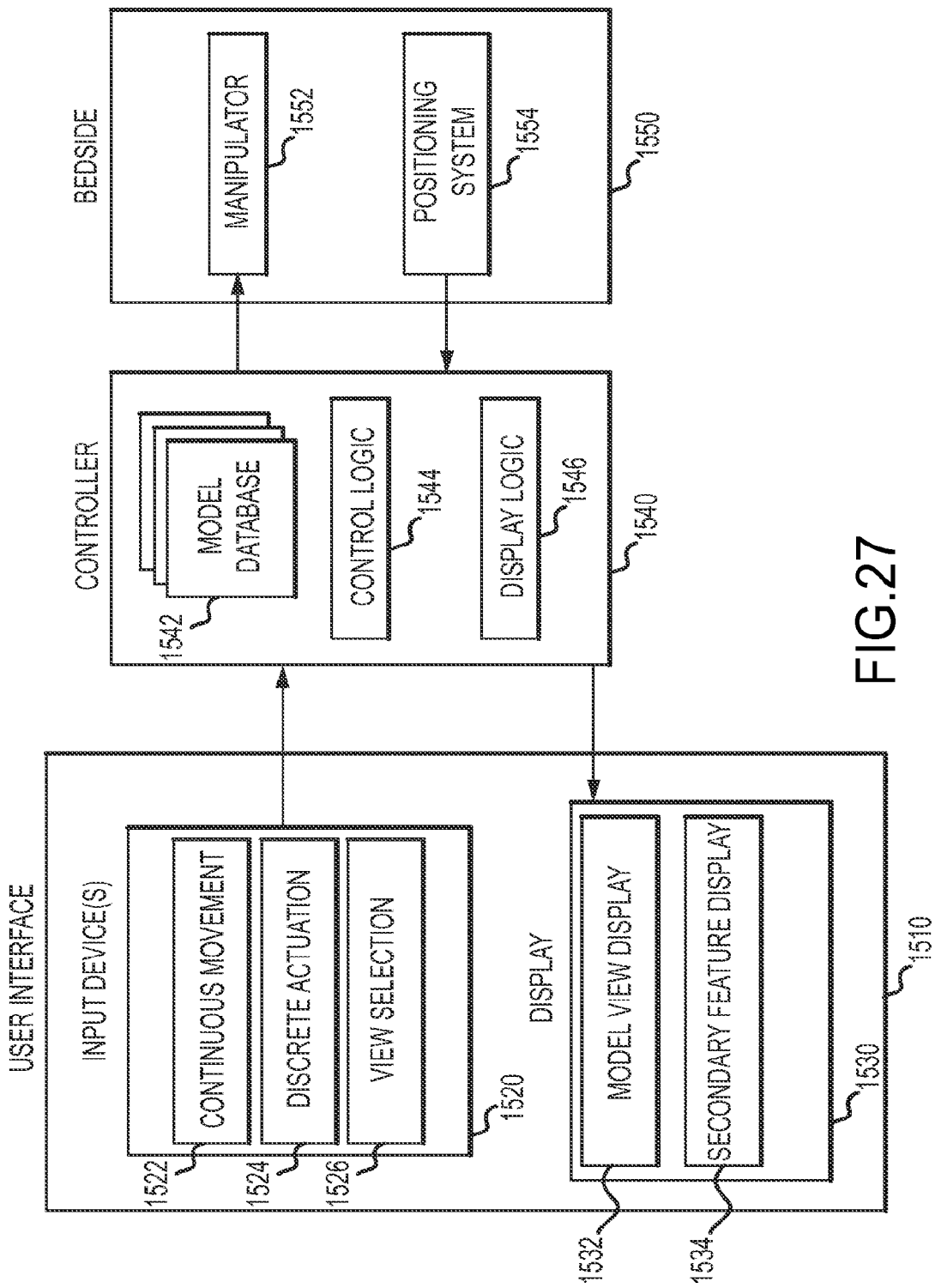
FIG. 27 is a diagram of an embodiment of a robotic catheter system.

As schematically represented in FIG. 27, and described above, the robotic catheter system 10 generally includes three primary components: a user interface 1510, a robotic controller 1540, and a bedside system 1550. The user interface 1510 generally includes one or more input devices 1520 and one or more displays 1530. The controller 1540 generally includes an anatomical model 1542, control logic 1544, and display logic 1546. The bedside system 1550 generally includes one or more manipulator assemblies 1532, and a positioning system 1554.

In an embodiment of the user interface 1510, the one or more input devices 1520 may be configured to receive input from a physician corresponding to both a continuous movement 1522 of the input device 1520 and a discrete actuation 1524 of the input device 1520. The user interface may further provide the physician with a means of selecting a particular viewing perspective 1526 of a three dimensional anatomical model 1542. As used herein, a continuous movement input is one that can be represented on a continuous spectrum, such as the movement of a joystick, mouse, or slider. While it is understood that current digital computing operates in discrete increments, the term "continuous movement" as herein used, is intended to only distinguish from a discrete actuation, such as a button press, which must be represented as a finite state. The input device 1520 is configured to provide the various forms of user input from the physician to the controller 1540 for processing.

The user interface 1510 may further include one or more visual displays 1510 that are capable of displaying one or more views 1532 of an anatomical model 1542. The display 1534 may further be configured to display one or more secondary features 1534 either together with, or apart from the displayed view of the model 1532. In an embodiment, secondary features may include markers, targets, sliders, menu buttons, patient vital data, or other useful visual information that may not be strictly representative of the anatomical model 1542. In an embodiment, the displayed view of the anatomical model may be selected 1526 by the user via the input device 1520.

As will be described in greater detail below, the controller 1540 may be configured to maintain a three dimensional anatomical model 1542 of the cardiac geometry, and execute both control logic 1544 and display logic 1546. In an embodiment, the control logic 1544 is configured to relate intended user actions into a controlled physical movement of the catheter and sheath. Such control logic may include the use of, for example, control algorithms, forward and/or inverse kinematic computations, and real-time feedback from the catheter, manipulator, or positioning system. In an embodiment, the display logic 1546 is configured to use three dimensional view rotation, translation, and/or projection techniques to present the user with a displayed representation 1532 of the anatomical model 1542 corresponding to the provided view selection input 1526. The display logic 1546 may further be configured to relate a user input 1522 made with respect to a presently displayed view 1532 into the coordinate system of the anatomical model.

The bedside system 1530 generally includes one or more manipulator assemblies 1532 configured to manipulate a catheter and sheath, and a positioning system 1534 configured to detect the real-time positioning of the catheter and sheath devices within the patient.

In an embodiment of the general control scheme, the controller 1540 may be configured to receive inputs from an input device 1520 configured to resemble a traditional catheter handle, as discussed above with reference to FIGS. 15a-15b. In such a scheme, the controller 1540 may be configured to actuate the manipulator 1552 in a manner that translates the traditional inputs into a resulting motion of the catheter distal tip as if the handle and tip were physically connected. In this configuration, the control logic 1544 may be designed to mimic the feel and operation of a non-robotic catheterization.

In another embodiment of the general control scheme, the controller 1540 may be configured to register user inputs as they are made with respect to a displayed third-person view of the catheter and anatomic model 1542. The physician may therefore be able to use the input device 1520 to move the virtual catheter across the display 1530 in much the same manner as in a traditional computer experience, where a user can use a mouse to drag an object across a display screen. Said another way, a leftward motion of the input device 1520 would result in a leftward movement of the displayed catheter within the currently displayed view 1532 of the anatomical model 1542. The controller 1540 would then be configured to resolve the intended Cartesian distal catheter movements into deflection and translation manipulator actuation commands through control logic 1544 that may cause the actual catheter tip to follow the intended movements.

In another embodiment of the general control scheme, the controller 1520 may be configured to register user inputs as they are made with respect to a displayed third-person view of the catheter and anatomic model 1542 solely for the purpose of controlling directional bending of the catheter. In such an embodiment, translation of the catheter may be separately controlled through the use of a slider, wheel, unused device axis, or other similar device. The controller 1540 would therefore be configured to resolve the intended display-plane distal catheter movements into deflection-only manipulator actuation commands through control logic 1544, which would cause the actual catheter tip to follow the intended movements within the display plane, but would allow movement orthogonal to the display plane to be controlled by the mechanics of the catheter.

In another embodiment of the general control scheme, the controller 1520 may be configured to register user inputs as if the user was navigating the catheter from a first person point of view. In such an embodiment, the display 1530 would represent the anatomic model 1542 as if the viewing camera was positioned on the tip of the catheter. The physician would therefore be able to use the input device 1520 to steer the catheter in much the same way a driver steers a car while looking out of the front windshield.

Figure 28A:
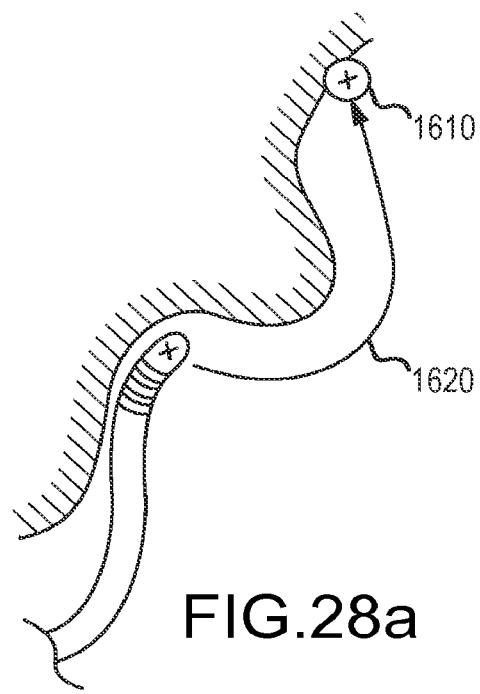
FIG. 28a-28b are illustrations of embodiments of specifying an intended robotic catheter movement path.
Figure 28B:
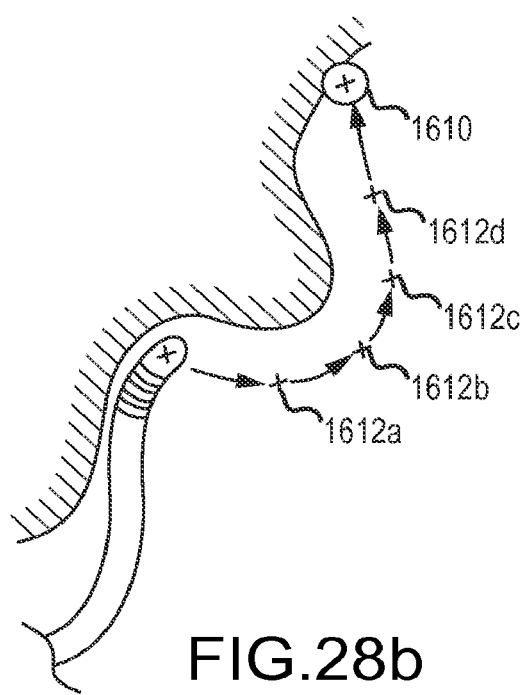

In yet a further embodiment of the general control scheme, as generally illustrated in FIGS. 28a-28b, the controller may be configured to accept target locations 1610 or a series of way points (e.g., waypoints 1612a-1612d), for automated movement. In such a scheme, a user may, for example, select a target point 1610 within the model that he or she intends the catheter to move to. The controller may then construct a path 1620 between its current location and the target. In an embodiment, prior to movement, the controller may employ various optimization and/or path planning routines to construct an optimal path, traversing potential obstructions within the model. In another embodiment, the controller may cause the catheter to move in a direction toward the target location, while employing real-time proximity feedback from the actual catheter to avoid contact with obstructing tissue. Using either method, the controller may determine the necessary steering wire movement required to cause the catheter to progress toward the target while avoiding contact with the tissue. In an embodiment, as shown in FIG. 28a, the physician my use a target destination as an end-point destinations where a particular therapy may be administered. In an embodiment, as shown in FIG. 28b, the physician may use interim way points (such as waypoints 1612a-1612d) or incremental target locations to construct a specific course for the catheter.

Referring back to FIG. 27, the ability to control the ultimate motion of the catheter (via the manipulator actuation) is complicated because each of the input device 1520, the display 1530, the anatomical model 1542, the manipulator 1552, the distal motion of the catheter resulting from manipulator actuation 1552, and the positioning system 1554, may reside in different domains, having different coordinate systems. As used herein, a "coordinate system" or "coordinate frame" is intended to refer a collection of variables representing controllable or perceivable qualities of an object or device. These variables may primarily include position and/or orientation, though should not necessarily defined in Cartesian space. Additionally, other temporal or environmental variables that are not strictly related to position or orientation may be included in a given coordinate system (e.g., time, breathing phase/magnitude, ECG phase/magnitude). It should also be noted that while a given unit may represent a physical distance, it may be represented in various forms, such as for example, inches, millimeters, volts, ohms, impedance, encoder counts, or other such quantities.

Figure 29A:
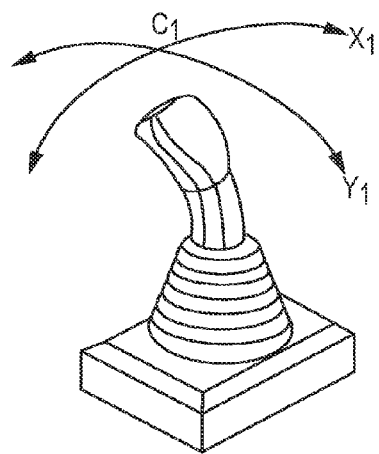
FIGS. 29a-29e illustrate exemplary coordinate systems used in a robotic catheter system.

FIGS. 29a-29e illustrate the various coordinate systems described above. As illustrated in FIG. 29a, an input device, shown as a generic joystick, may operate in a first coordinate system $C_1$. As illustrated, the input coordinate system C, may include two continuous positional degrees of freedom, $\{x_1, y_1\}$. Depending on the nature of the input device, $C_1$ may further include additional degrees of freedom meant to reflect additional motion, orientation, and/or discrete event triggers.

Figure 29B:
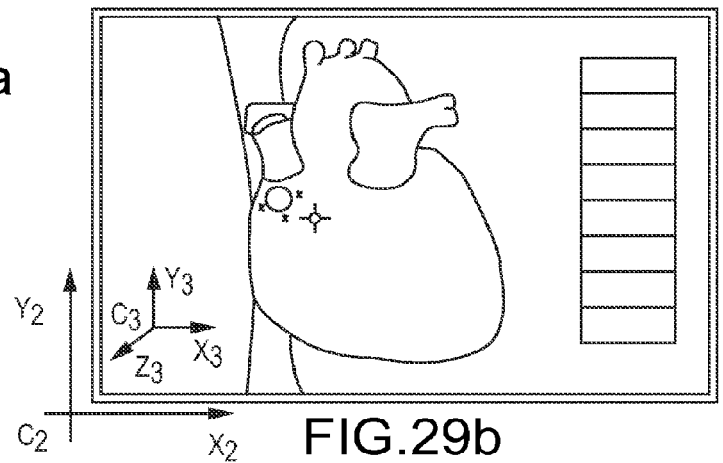
Figure 29C:
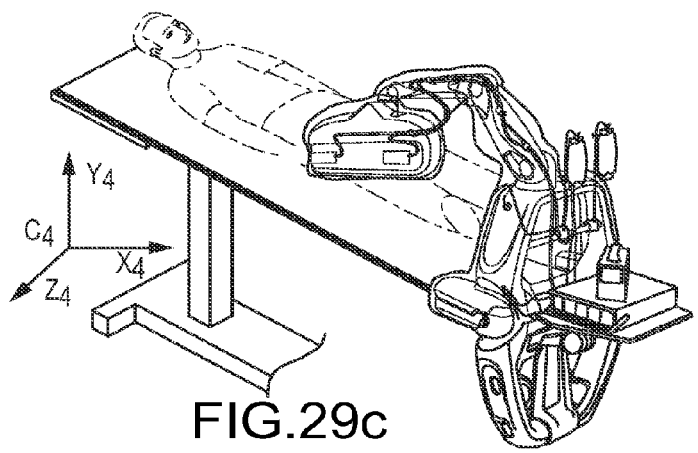
Figure 29D:
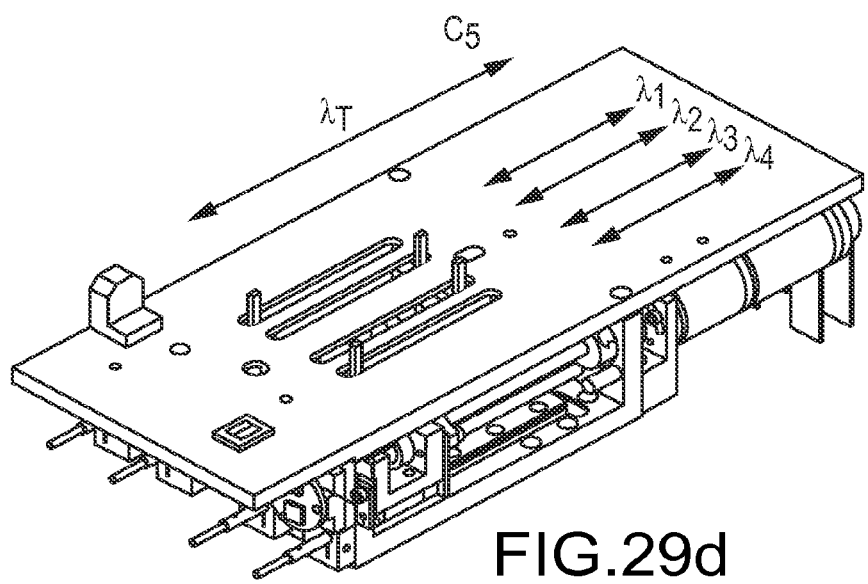

As illustrated in FIG. 29b, the display may have a second coordinate system $C_2$ that may be capable of displaying an image in two dimensional Cartesian space, $\{x_2, y_2\}$. The computerized anatomical model representing the patient's physical anatomy may be registered in the controller as a collection points in a third coordinate system $C_3$, where each point may be defined in a three dimensional Cartesian space $\{x_3, y_3, z_3\}$. As generally illustrated in FIG. 29c, the actual catheter and patient anatomy may exist in a fifth coordinate frame $C_4$, that may have six degrees of freedom $\{x_4, y_4, z_4, \theta_4, \phi_4, \psi_4\}$ established by the positioning system, where $\{x_4, y_4, z_4\}$ are registered positional coordinates of a given object, and $\{\theta_4, \phi_4, \psi_4\}$ define the object's orientation in three dimensional space. As shown in FIG. 29d, the manipulator may operate in a fourth coordinate system $C_5$, where each carriage has, for example, four degrees of freedom that relate to the motion of the four steering wires, and one degree of freedom that relates to the translational motion of the carriage $\{\lambda_1, \lambda_2, \lambda_3, \lambda_4, \lambda_T\}$. In two carriage system (i.e., where the manipulator capable of independent catheter and sheath control), each carriage may have, for example, five degrees of freedom, thus providing a manipulator with 10 total degrees of freedom $\{\lambda_1^1, \lambda_2^1, \lambda_3^1, \lambda_4^1, \lambda_T^1, \lambda_1^2, \lambda_2^2, \lambda_3^2, \lambda_4^2, \lambda_T^2\}$.

Figure 29E:
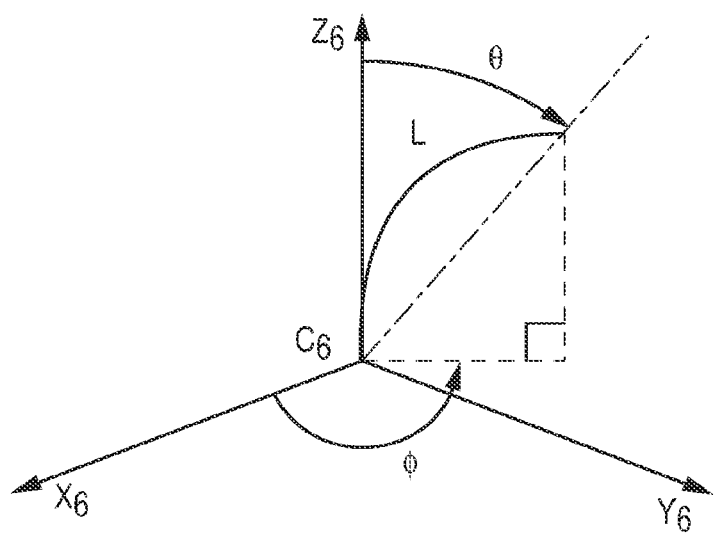

Finally, as shown in FIG. 29e, the distal motion of the catheter may be locally described in a sixth coordinate system, $C_6$, that may be located at the fulcrum point of the catheter. The distal motion within $C_6$ may be described either in a Cartesian space $\{x_6, y_6, z_6\}$ with the z-axis oriented along the longitudinal axis of the catheter, or in a pseudo-spherical space $\{\theta_6, \phi_6, L_6\}$. In addition to the degrees of freedom listed above, the coordinate systems of the computerized model $C_3$ and the positioning system $C_5$ may be configured to record temporal and environmental degrees of freedom, such as, for example, time, ECG phase, ECG rate, respiration rate, respiration phase, and/or respiration magnitude.

Figure 30:
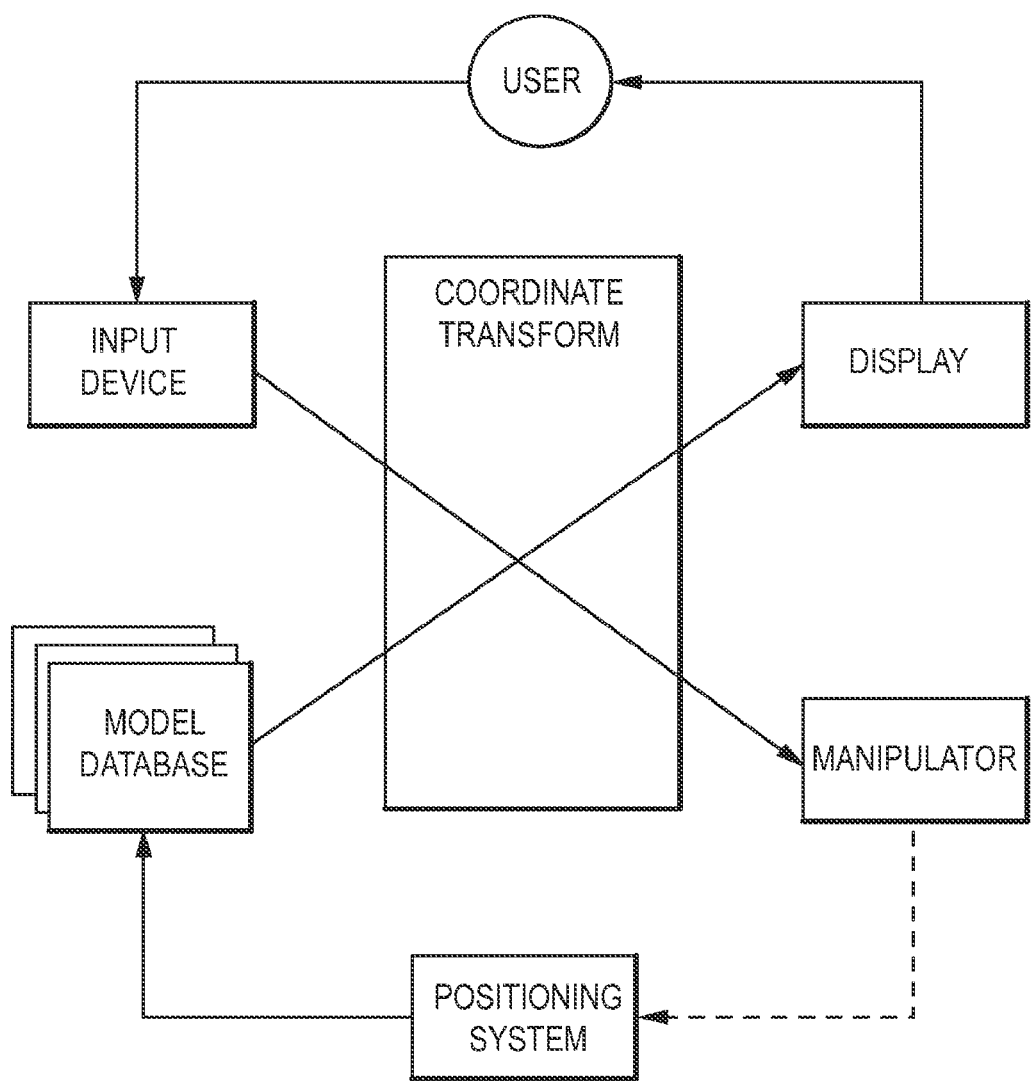
FIG. 30 is a relational diagram for exemplary aspects of a robotic catheter system.

As illustrated in FIG. 30, and described in more detail below, the controller must understand the relationship between the various system elements and coordinate frames and be capable of transforming motions in one coordinate frame into similar motions in another coordinate frame. In the embodiment schematically illustrated in FIG. 30, a user may perform an action at the user input device ($C_1$) while presented with a displayed view ($C_2$) of an anatomical model and distal portion of the catheter. The controller must transform the sensed user input motion into a corresponding motion of the proximal actuators of the manipulator ($C_5$). The proximal actuation of the manipulator causes a movement of the distal catheter tip ($C_6$), which is registered by the positioning system ($C_4$) and fed into the model database (CJ). The controller must then transform the updated three dimensional model ($C_3$) into a particular two dimensional view for display to the user via the display device ($C_2$).

An embodiment of the control scheme will now be discussed with regard to FIG. 31.

Figure 31:
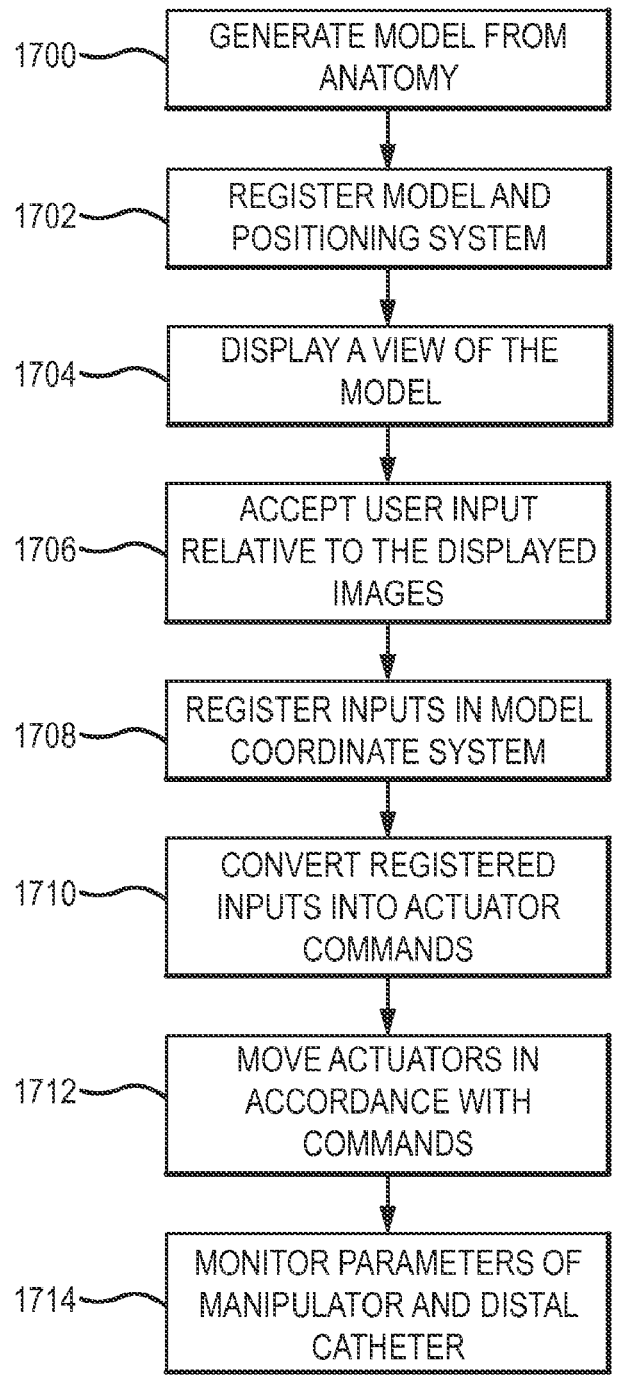
FIG. 31 is a flow chart illustrating an embodiment of a robotic catheter control scheme.

As generally represented by the flowchart in FIG. 31, a model representing the subject's anatomy must first be generated (1700) and registered (1702) to the real-time positioning system. The controller may then display a particular view of the model (1704), and accept user inputs relative to the displayed model (1706) and register them in the model coordinate system (1708). Using the current position of the catheter, along with the registered user input, the controller may compute the necessary manipulator actuation required to move the catheter as intended by the user (1710). The controller then may command the actuators to move in accordance with the computed actuation commands (1712) and monitor parameters of the manipulator and distal catheter tip (1714). Further detail relating to each step will be provided below.

In an embodiment, a model of the operative site is first generated from the physical anatomy of the subject (1702). This generated model may serve as a basis or a reference for the physician's control, and should reflect the features of the subject's anatomy. The model may be generated by, for example, using pre-existing MRI or CT imagery, or may be generated by monitoring the real-time movement of an invasive probe, such as with the EnSite NavX system available from St. Jude Medical. In the case of a probe, axes of a coordinate system may be generated between pairs of patch electrodes located on the skin of the patient (such as described in detail in U.S. Pat. No. 7,263,397, titled "Method and Apparatus for Catheter Navigation and Location and Mapping in the Heart," incorporated by reference in its entirety). A catheter with a position sensing electrode may be swept around the internal geometry while it communicates its position relative to the pairs of electrodes to the controller. Through either contact sensing means or various skinning techniques, a shell may be constructed around the outermost points of the recorded three dimensional data cloud. This shell may then be the basis of the anatomical model maintained by the controller. Likewise, other similar positioning/modeling systems my be used to generate the stored anatomical model. Such systems may include, for example, the Mediguide gMPS system, or the Biosense Webster Carto system.

In an embodiment where the model is generated by a real-time positioning system such as EnSite NavX, the registration (1702) may be implicit (i.e., $C_3=C_4$), where no further registration is needed. If other real-time factors (e.g., breathing and/or respiration) are sensed by the positioning system, however, a registration may still be necessary. Alternatively, in an embodiment where the model is imported from previously acquired CT or MRI imagery, the model may be registered to the coordinate system of the real time positioning system through scaling and/or rotating techniques such as those provided by the EnSite Fusion dynamic registration system, commercialized by St. Jude Medical.

In a configuration where the physician makes input movements with respect to a third person view of a displayed catheter and anatomic model, the physician must first select a viewing perspective from which to perceive the model (1704). This may be accomplished through the use of a display controller. The display controller may allow the physician to manipulate the displayed view of the anatomic model, and may include, for example, a 3D mouse, or spaceball such as those commercially available from 3Dconnexion, or may include various on-screen controls that would allow the user to pan, zoom, and/or rotate the model.

In operation, as generally illustrated in the display controller may serve to manipulate a projection of the 3D model onto the 2D display by first rotating/translating the model in 3D space, and then projecting the model onto a 2D viewing plane. The rotation/translation may be accomplished using a homogeneous model view transformation matrix ($T_V$). In an embodiment, the model view transformation matrix ($T_V$) may be of the form shown in Equation 1, where the 3×3 matrix of $R_{1-9}$ relates to a rotation of the model in three dimensional space, and the 3×1 matrix of $T_{1-3}$ relates to a translation of the model in three dimensional space.

$$T_V = \begin{bmatrix} R_1 & R_2 & R_3 & T_1 \\ R_4 & R_5 & R_6 & T_2 \\ R_7 & R_8 & R_9 & T_3 \\ 0 & 0 & 0 & 1 \end{bmatrix} \quad (eq.\ 1)$$

Figure 32:
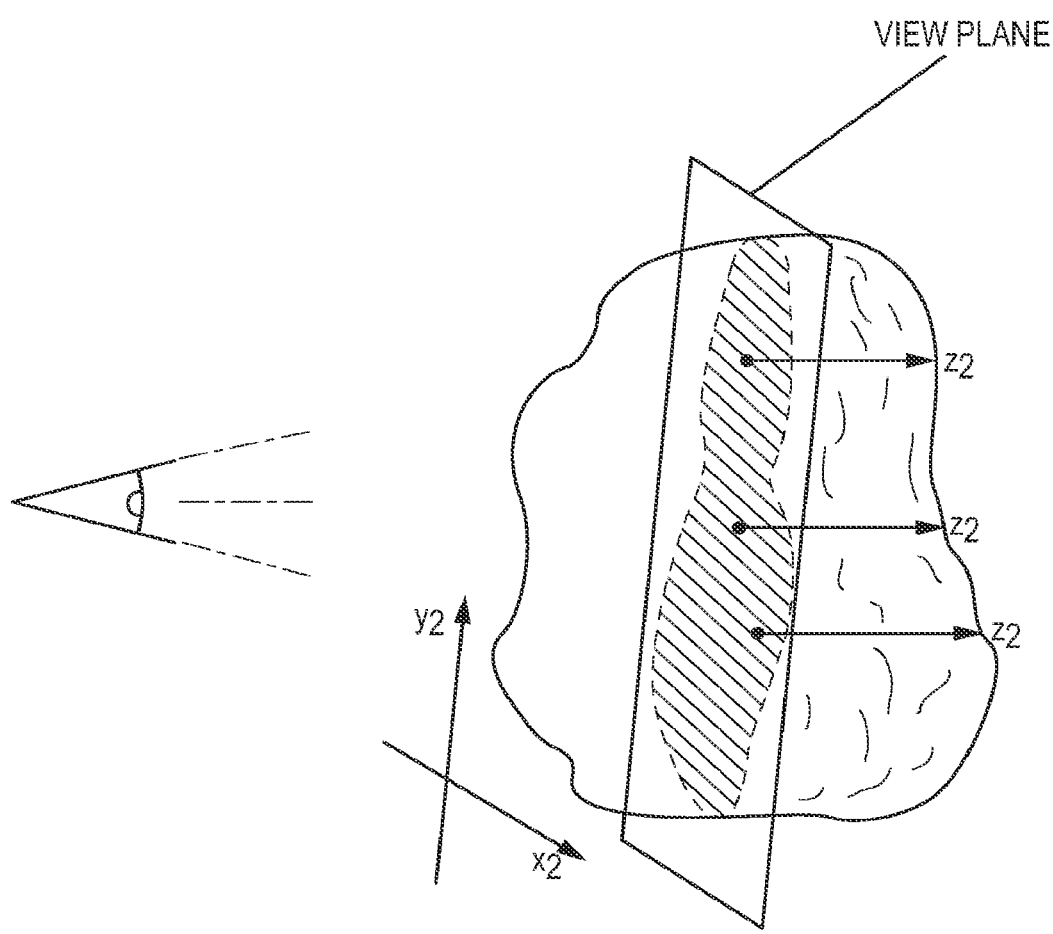
FIG. 32 illustrates a projection of an anatomical model to a viewing plane according to an embodiment.

Such model view transformation matrices are commonly implemented through high-level commands in rendering applications, such as OpenGL, and ultimately have the effect of repositioning or rotating a model in front of a fixed camera. Once the model is positioned in three dimensional space, it may then be projected to a two dimensional viewing plane, as generally illustrated in FIG. 32. At this stage, the system may internally buffer a transverse depth value (i.e., $z_2$) for each two dimensional primitive or point depicted within the viewing plane. Once the model is projected to the viewing plane, it may be displayed to a user on a two dimensional computer monitor. The user then may use the displayed projection of the anatomical model as a reference while providing an input to the input device.

As described above, the user may indicate intended movements of the catheter to the system by using an input device. Potential input devices may include, for example, a two or three dimensional mouse or joystick, a spatially detected stylus, a touch screen, or other similar forms or input. As generally described above, the user may specify this intended movement in a manner that directly moves the catheter tip across the screen similar to controlling a computer pointer arrow with a computer mouse. Alternatively, the user may select a point along the catheter and drag it across the screen similar to dragging an icon across a computer desktop. In yet another embodiment, the user may use the input device to specify way-points or target points within the model for semi-automated or fully-automated movement.

Referring back to FIGS. 29a, 29b, in an embodiment, the coordinate frame of the input device (e.g., $C_1$) may be aligned with the coordinate system of the display (e.g., $C_2$), such that a leftward movement of the input device may cause a corresponding leftward movement of an object on the display (e.g., a negative $x_1$ movement of the input device would correspond to a negative $x_2$ motion within the display). By knowing the relationship between the displayed view ($C_2$) and the model coordinate system ($C_3$) (e.g., via the model view transformation matrix, $T_V$) the system may be configured to then relate the input movement (e.g., $C_1$) into the model coordinate system ($C_3$). This relation may generally be expressed by equation 2, where $T_V^T$ is the transpose of the model view transformation matrix ($T_V$), and s represents an scaling factor that may be applied to scale the user input.

$$\begin{bmatrix} x_3 \\ y_3 \\ z_3 \\ 1 \end{bmatrix} = sT_V^T \begin{bmatrix} x_1 \\ y_1 \\ (z_1) \\ 1 \end{bmatrix} \quad (eq.\ 2)$$

As used in equation 2, ($z_1$) represents the out-of-plane movement of the input device. While in some embodiments, the input device may only be capable of two dimensional movement, this third dimension may be directly obtained from the device if, for example, a three dimensional input device, such as a 3D joystick, is used. Alternatively, when using a two-dimensional input device, this third dimension may be obtained from another input such as the rotation of a wheel. In another embodiment, ($z_1$) may be maintained as a constant that constrains the catheter's orthogonal motion to a plane that bisects the catheter's current position, and is parallel to the current viewing plane. If held as a constant, the catheter may be maneuvered in three dimensions by first rotating the view using the display controller, and then moving the catheter in the new viewing plane. In yet another embodiment, ($z_1$) may be retrieved from the stored $z_2$ buffer (i.e., the stored depth for each displayed point or primitive). In this manner, once a user selects a point on the display, the point may be immediately projected to the surface of the displayed anatomy. In an embodiment, the display may further provide an auxiliary view to aid the user in perceiving depth. It should also be understood that if the input device is configured to convey information regarding its orientation, equation 2 may be expanded to account for such rotation.

In still another embodiment, ($z_1$) may be allowed to vary freely based on the bending mechanics of the catheter while the directional bending of the catheter is controlled by the user. In such an embodiment, the manipulator may be constrained against automatic translation, and a directional movement in, for example, a two-dimensional input space (e.g., $C_1$) or two-dimensional display-space (e.g., $C_2$) would cause an inherent bending motion in the catheter. As such, ($z_1$) may be determined based on a knowledge of the current catheter pose, together with the direction of intended movement $\{x_1, y_1\}$, and an understanding of the bending mechanics of the catheter.

In an embodiment where the user appears to directly control a displayed catheter or sheath, the system may be configured so that the user is actually controlling a dynamic target point that is independent of the catheter. The system may be configured to cause the actual catheter to track this dynamic target point a closely as possible, though to the user, the point may either not be displayed or displayed as a marker. In an alternative embodiment, the target point may be displayed as a catheter, while the real-time catheter position may be displayed as a ghost-catheter (as generally illustrated in FIG. 19b). This indirect control may be necessary in a system where the position and orientation of the displayed catheter reflects the position and orientation of the actual catheter as detected by the positioning system. In an embodiment where the input device incorporates an activation switch, the dynamic target point may initially be set to the current position of the catheter. Upon actuation of the activation switch, the target point may be allowed to moved from the current catheter position based on the motion of the input device. Upon release of the activation switch, the target point may be returned to the new-current position of the device, or locked to it's position at the time of release.

Figure 33:
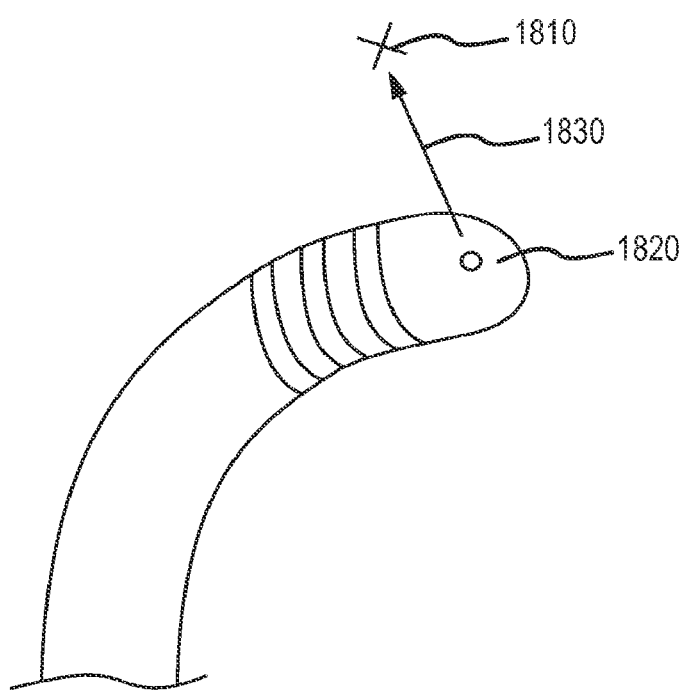
FIG. 33 illustrates an incremental catheter movement vector.

As generally illustrated in FIG. 33, once a desired movement is registered within the model, the dynamic target point (e.g., point 1810) or way-point may be compared to the current position of the actual catheter 1820. The controller may use this comparison to create a desired movement vector 1830 that points in the direction of the intended movement. While the desired movement vector 1830 may reflect the desired movement of the distal portion of the catheter, the manipulator is unable to directly reproduce this motion. Instead, the manipulator must indirectly attempt to achieve such motion by controlling the proximal actuation inputs (e.g., $\{\lambda_1, \lambda_2, \lambda_3, \lambda_4, \lambda_T\}$). To accomplish this, the controller may use a knowledge of the catheter dynamics to determine the proximal actuation that would be required to cause the desired distal motion. In general, as illustrated in FIG. 34, the system's "forward kinematic" relationships describe how known inputs (e.g., $\{\lambda_1, \lambda_2, \lambda_3, \lambda_4, \lambda_T\}$) cause a resulting movement of the distal end of the catheter (e.g., $\{x_6, y_6, z_6\}$ or ($\{\theta_6, \phi_6, L_6\}$). Likewise, "inverse kinematic" relationships operate in an opposite manner, where the system may compute the inputs that would result in a desired movement or pose.

Figure 35:
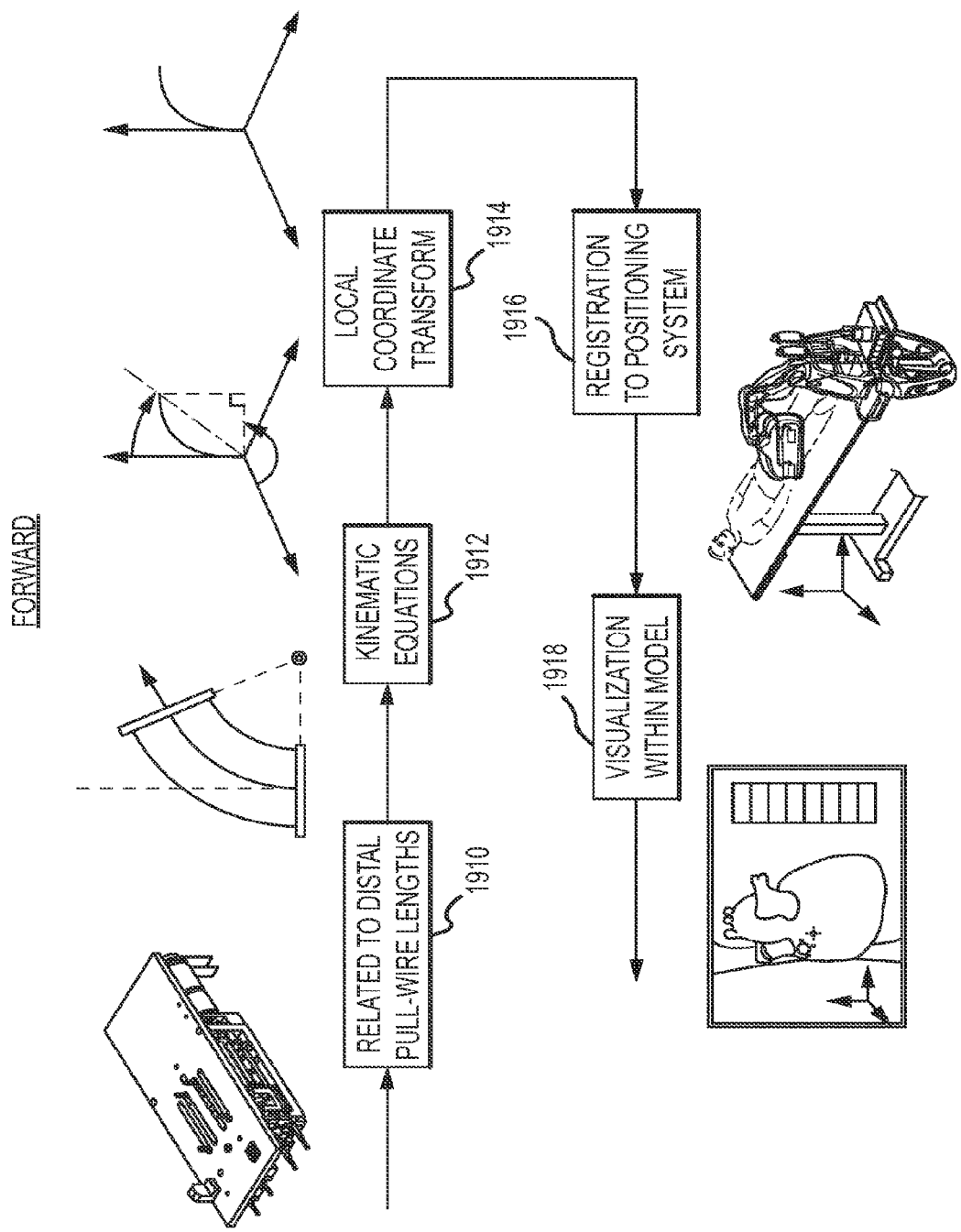
FIG. 35 is an illustration of an embodiment of a forward kinematic relationship.

FIG. 35 further illustrates an embodiment of the forward kinematics of a robotic catheter system. In step 1910, known inputs (e.g., ($\{, \lambda_1, \lambda_2, \lambda_3, \lambda_4, \lambda_T\}$) may be related to steering wires lengths (e.g., $\{L_A, L_B, L_C, L_D\}$) that extend between a distal fulcrum point and a pull ring. Through the use of known kinematic relationships, in step 1912, these steering wire lengths may be used to understand the deflection characteristics of the distal portion of the catheter (e.g., $\{\theta_6, \phi_6, L_6\}$). This characterization of the current pose may then be converted into a local Cartesian reference frame (e.g., $\{x_6, y_6, z_6\}$) through a coordinate transform in step 1914. In step 1916, the local Cartesian reference frame may then be registered to the coordinate system of the positioning system (e.g., $\{x_4, y_4, z_4\}$), which may subsequently be registered to a particular model coordinate system (e.g., $\{x_3, y_3, z_3\}$) in step 1918.

Figure 36:
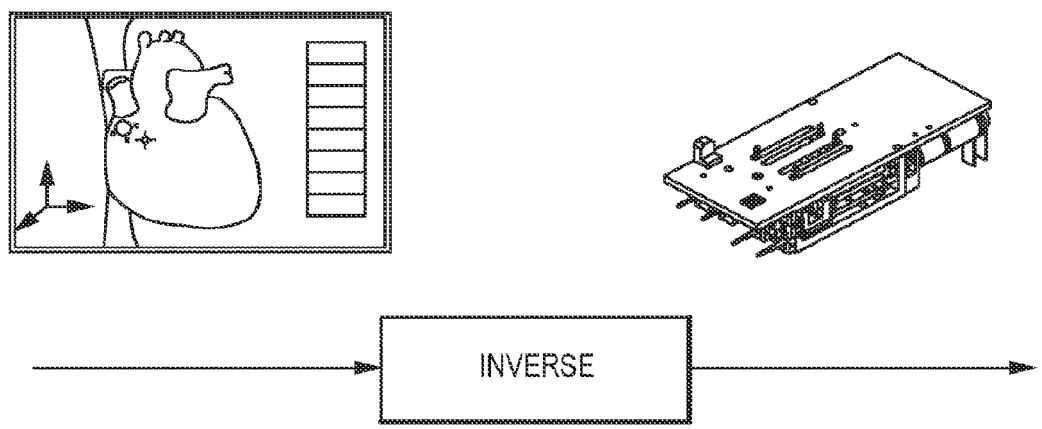
FIG. 36 is an illustration of an embodiment of an inverse kinematic relationship.

Using these "forward" relationships, the system may accurately predict how a particular manipulator actuation (often referred to as "joint variables") would affect the catheter position registered within the model. This, however, is the direct opposite of the relationships needed from a control perspective. As generally illustrated in FIG. 36, in an embodiment of the robotic catheter system, the system must be able to convert desired movements from within the model into actuation inputs that would result in the desired movement. While the inverse kinematic relationships may be theoretically derived, they may also be computed by numerically inverting the forward kinematics. Numerical inversion, such as through pseudo-inverse Jacobian methods, is often a preferred method of determining the inverse kinematic relationships when the system is highly complex or nonlinear.

Beginning with the forward kinematics as shown in FIG. 35, in step 1910, the proximal actuation (e.g., $\{\lambda_1, \lambda_2, \lambda_3, \lambda_4, \lambda_T\}$) must first be related to the behavior of the steering wires between a distal fulcrum point and a pull ring (i.e., within the "bendable portion"). In an embodiment, it may be assumed that the changes in the lengths of the steering wires within the bendable portion directly relate to the proximal steering wire actuation by the manipulator (i.e. $\{\Delta L_A, \Delta L_C\} \approx \{\Delta \lambda_1, \Delta \lambda_3\}$). In another embodiment, length measurements may be taken directly from the steering wires within the bendable portion by, for example, passing a known current through the steering wire and measuring the voltage drop in the wire between a fixed point at the fulcrum and the distal pull ring (described in detail in commonly owned and copending application titled "Catheter With Length Determination Feature" filed 2 Mar. 2010 as U.S. patent application Ser. No. 12/716,056 which is hereby incorporated by reference herein in its entirety). By knowing the applied current, the voltage drop, and the resistance per unit length of the wire, the controller may determine the length of wire between the fixed fulcrum point and the pull ring.

Figure 37A:
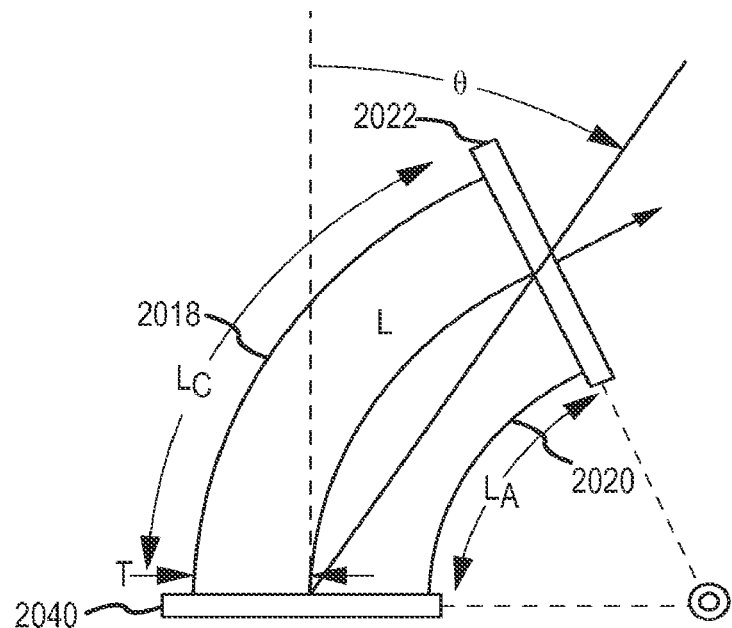
FIGS. 37a-37b are schematic representations of a bendable portion of a catheter illustrating, respectively, a deflection angle and a heading angle.
Figure 37B:
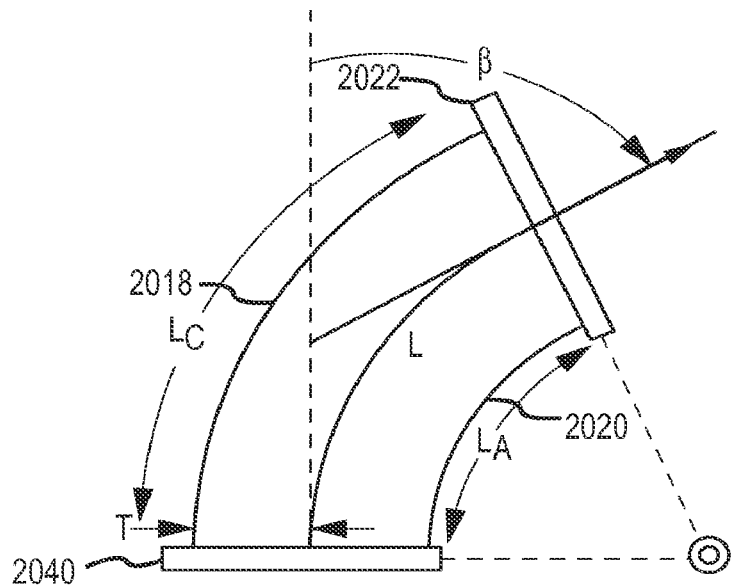

Once the steering wire lengths (e.g., $\{L_A, L_B, L_C, L_D\}$) within the bendable portion are known, the system may use known relationships to compute the deflection characteristics of the distal portion of the catheter. As illustrated in FIGS. 37a, 37b, in a two-steering wire configuration, where a constant curvature is assumed, the planar deflection of the bendable portion of the catheter can generally be expressed as a function of the nominal length (i.e., length L) of the catheter between fulcrum point 2040 and pull ring 2022 (the "bendable portion"), and either a deflection angle θ or heading angle β. Assuming a uniform thickness 2T and a knowledge of the steering wire lengths within the bendable portion (i.e., lengths $L_A$, $L_C$), the nominal length L can be determined using equation 3, and deflection angle θ can be determined using equation 4. Furthermore, in a planar configuration, the heading angle β is generally twice the deflection angle θ.

$$L = \frac{L_A + L_C}{2} \qquad \text{(eq. 3)}$$

$$\theta = \frac{L_C - L_A}{2} \times \frac{1}{2T} \qquad \text{(eq. 4)}$$

Figure 38:
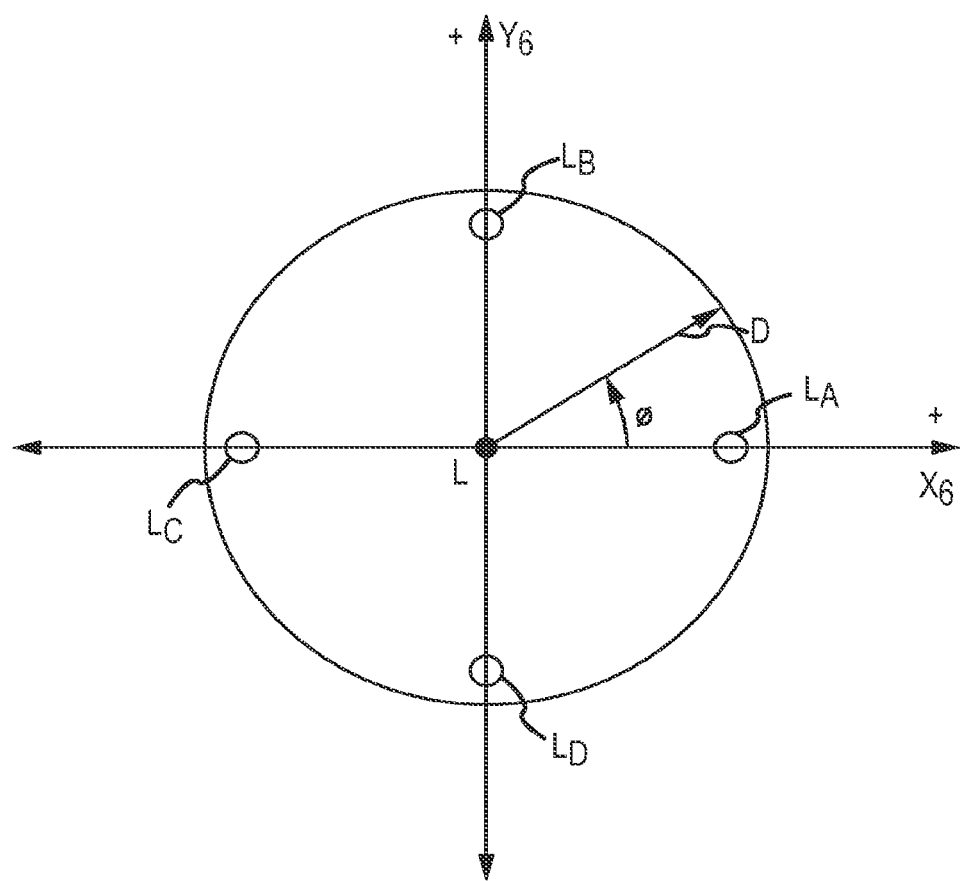
FIG. 38 is an illustration of a cross section of a catheter.

In a four steering wire embodiment, as illustrated in the cross-sectional view shown in FIG. 38 (taken of a four steering wire catheter at fulcrum point 2040), the calculation of the nominal length L may be affected by all four steering wire lengths $\{L_A, L_B, L_C, L_D\}$, as referenced in equation 5. Further, the deflection angle θ, may be determined using the relationship expressed in equation 6, and the azimuth angle ϕ may be determined through the relationship in equation 7.

$$L = \frac{L_A + L_B + L_C + L_D}{4} \quad \text{(eq. 5)}$$

$$\theta = \pm\sqrt{(L_A - L)^2 + (L_B - L)^2} \times \frac{1}{2T} \quad \text{(eq. 6)}$$

$$\phi = \arctan\left(\frac{L_B - L}{\pm\sqrt{(L_A - L)^2 + (L_B - L)^2}}, \frac{L_A - L}{\pm\sqrt{(L_A - L)^2 + (L_B - L)^2}}\right) \quad \text{(eq. 7)}$$

As referenced in Step 1914 of FIG. 35, these local pseudo-spherical coordinates (i.e., $\{\theta_6, \phi_6, L_6\}$) may then be transformed into a local Cartesian coordinate frame $\{x_6, y_6, z_6\}$, where $z_6$ is aligned with the longitudinal axis of the catheter at the fulcrum point, and $x_6$, for example, is aligned with steering wire "A" (as shown in FIG. 38). Alternatively, it should be understood that the local catheter position may directly be computed in a Cartesian reference frame, without the use of any intermediate reference frame.

In another embodiment, instead of using closed-form analytical modeling to understand how inputs (e.g., steering wire lengths $\{L_A, L_B, L_C, L_D\}$) relate to local movement in the bendable section (e.g., $\{x_6, y_6, z_6\}$), the system may employ empirical modeling techniques to model the catheter's behavior. These techniques may use actual observations to describe and predict how an object will behave, rather than relying on mathematically describable relationships. Examples of such empirical modeling techniques include neural network techniques such as without limitation, recurrent neural network modeling, or hysteretic recurrent neural network modeling. A hysteretic recurrent neural network model, for example, may accept the steering wire lengths and past local tip positions as inputs to the network, and may be configured to determine a resultant position from this information. The model may be trained prior to the actual procedure by experimentally manipulating the catheter throughout its full range of motion, or a portion of the full range of motion, and inputting the measured parameters and poses into the network to refine the model. These relationships may be determined from a catheter that is substantially similar in design or construction to the catheter that will be used in the procedure. The empirical model may reflect the kinematic properties of the catheter or sheath, and may be configured to account for material non-linearities, such as plastic deformation or axial compression, that may develop through use.

While local modeling, such as shown in equations, 5-7, may provide a useful insight into the mechanics of the distal catheter bending, the motions (i.e., $\{x_6, y_6, z_6\}$ or $\{\theta_6, \phi_6, L_6\}$) are computed in a catheter-centric relative coordinate frame. As described above, however, the user desired catheter motions are specified in the coordinate system of the model/positioning system. Therefore, as referenced in Step 1916 of FIG. 35, the system may be configured to register the relative catheter-centric coordinate frame $\{x_6, y_6, z_6\}$ to the coordinate frame of the positioning system (i.e., $\{x_4, y_4, z_4\}$). This registration may achieved by computing a homogeneous catheter transformation matrix ($T_C$) of the form shown in equation. 8.

$$T_C = \begin{bmatrix} i_x & i_y & i_z & t_x \\ j_x & j_y & j_z & t_y \\ k_x & k_y & k_z & t_z \\ 0 & 0 & 0 & 1 \end{bmatrix} \quad \text{(eq. 8)}$$

In an embodiment, $T_C$ may be computed empirically by physically moving the catheter through a series of positions and recording the coordinates of the catheter in both the catheter reference frame and the positioning system reference frame. The recorded point pairs may then be used, for example, in a regression analysis, to determine the values for $T_C$ that would satisfy the relationship expressed in equation. 9, where $\vec{C}_4$ represents the points recorded by the positioning system, and $\vec{C}_6$ represents the points in the local catheter-centric reference frame.

$$\vec{C}_4 = T_C \cdot \vec{C}_6 \quad \text{(eq. 9)}$$

Figure 39:
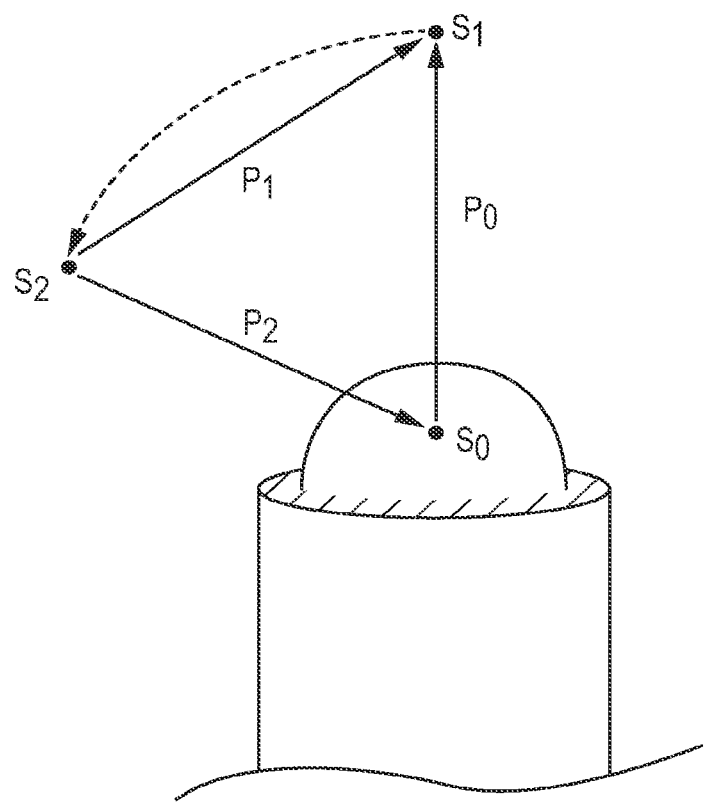
FIG. 39 is a representation of a catheter movement to accomplish a model registration.

In an embodiment, $T_C$ may be computed by recording the point pairs at a series of three points $\{S_0, S_1, S_2\}$ as shown in FIG. 39, and represented in the following table:

| Point | $L_A$ | $L_B$ | $L_C$ | $L_D$ | L |
|---|---|---|---|---|---|
| $S_0$ | 0 | 0 | 0 | 0 | z |
| $S_1$ | 0 | 0 | 0 | 0 | z + Δz |
| $S_2$ | Δa | 0 | auto | 0 | z + Δz |

As used in the table, $L_A, L_B, L_C, L_D$ represent the lengths of four steering wires within the bendable section (in a four steering wire catheter embodiment), while L represents the axial translation of the catheter. Point $S_0$ may be specified such that the catheter is positioned slightly beyond the sheath, though in an undeflected state. The motion from $S_0$ to $S_1$ is accomplished by translating the catheter distally an amount Δz, such as an amount equal to the bendable length of the catheter. The motion from $S_1$ to $S_2$ is then accomplished by displacing pull wire "A" a distance Δa, sufficient to, for example, bring the catheter to a deflection angle of between π/4 and π/2. A value of 'auto,' as used in the table, indicates that while pull wire "A" is being displaced, pull wire C should be moved in such a manner to not impede the deflection of the catheter, though should also be auto-tensioned to prevent slack from developing.

Once points $\{s_0, s_1, s_2\}$ are established, vectors $\{\vec{P}_0, \vec{P}_1, \vec{P}_2\}$ may be defined within the coordinate frame of the positioning system and used to create a set of orthogonal basis vectors represented by equations 10-12.

$$\vec{K} = \vec{P}_0 \quad \text{(eq. 10)}$$

$$\vec{J} = \vec{P}_1 \times \vec{P}_2 \quad \text{(eq. 11)}$$

$$\vec{I} = \vec{K} \times \vec{J} \quad \text{(eq. 12)}$$

These vectors may then be normalized, and used to assemble the rotation portion of the homogeneous catheter transformation matrix referenced in equation 8. This rotation matrix is shown explicitly in equation 13.

$$R = \begin{bmatrix} i_x & i_y & i_z \\ j_x & j_y & j_z \\ k_x & k_y & k_z \end{bmatrix} \quad \text{(eq. 13)}$$

Furthermore, if $S_0$ is defined as the relative origin, for example, the transformation vector included in equation 8 may be determined through equation 14.

$$\vec{t} = -R\vec{s}_0 \quad \text{(eq. 14)}$$

Once the homogeneous catheter transformation matrix is assembled, it may be used via equation 9 to relate the computed local motion of the catheter into the coordinate system of the positioning system, as referenced in step 1918 of FIG. 35. In an embodiment, where the positioning system is registered to the model, the computed catheter motion may therefore be oriented and placed within the model. Thus the forward relationships, illustrated in FIG. 35, may be useful to analytically predict how a given actuation input may move the catheter within the patient, which in turn may be related to a movement of a model of the catheter within the anatomical model.

Using the relationships expressed above, and graphically illustrated in FIG. 35, a Jacobian matrix may then be constructed to directly relate a change in actuation inputs or actuation input motion (e.g., $\{\lambda_1, \lambda_2, \lambda_3, \lambda_4, \lambda_T\}$ or $\{L_A, L_B, L_C, L_D\}$) into a change in distal tip position within the anatomical model (e.g., $\{x_3, y_3, z_3\}$), as illustrated in equations 15-16.

$$J = \begin{bmatrix} \frac{\partial x_3}{\partial L_A} & \frac{\partial x_3}{\partial L_B} & \frac{\partial x_3}{\partial L_C} & \frac{\partial x_3}{\partial L_D} & \frac{\partial x_3}{\partial L} \\ \frac{\partial y_3}{\partial L_A} & \frac{\partial y_3}{\partial L_B} & \frac{\partial y_3}{\partial L_C} & \frac{\partial y_3}{\partial L_D} & \frac{\partial y_3}{\partial L} \\ \frac{\partial z_3}{\partial L_A} & \frac{\partial z_3}{\partial L_B} & \frac{\partial z_3}{\partial L_C} & \frac{\partial z_3}{\partial L_D} & \frac{\partial z_3}{\partial L} \end{bmatrix} \quad \text{(eq. 15)}$$

$$\dot{X}_3 = J\dot{L} \quad \text{(eq. 16)}$$

While a closed solution to the partial derivatives expressed in equation 15 may be difficult to compute, the derivatives may be approximated at a given point, by analyzing how small (delta) changes of the input motions affect the end-effecter coordinates at that point according to the model. To calculate these approximations, the controller may numerically apply a small perturbation to the current position of each of the distal steering wires ($\vec{L}$) in both the positive and negative direction. These perturbed motions may be passed through the forward kinematic model (illustrated in FIG. 35) and related to end effector motions (i.e., $\{x_3, y_3, z_3\}$). The partial differential approximation may then be calculated by dividing the estimated change in position by the change in distal steering wire motions, as shown in equation 17.

While the relationship expressed in equation 16 may be useful to predict a catheter $$J_{approx} = \begin{bmatrix} \frac{\Delta x_3}{\Delta L_A} & \frac{\Delta x_3}{\Delta L_B} & \frac{\Delta x_3}{\Delta L_C} & \frac{\Delta x_3}{\Delta L_D} & \frac{\Delta x_3}{\Delta L} \\ \frac{\Delta y_3}{\Delta L_A} & \frac{\Delta y_3}{\Delta L_B} & \frac{\Delta y_3}{\Delta L_C} & \frac{\Delta y_3}{\Delta L_D} & \frac{\Delta y_3}{\Delta L} \\ \frac{\Delta z_3}{\Delta L_A} & \frac{\Delta z_3}{\Delta L_B} & \frac{\Delta z_3}{\Delta L_C} & \frac{\Delta z_3}{\Delta L_D} & \frac{\Delta z_3}{\Delta L} \end{bmatrix} \quad \text{(eq. 17)}$$

motion for a given input, as explained above, the inverse of this function may be more useful from a control perspective. As shown in equation 18, the inverse Jacobian function may be used to relate a chance in desired catheter movement into the motions needed to obtain that desired result.

$$\dot{\vec{L}} = J^{-1}\dot{X}_3 \quad \text{(eq. 18)}$$

In general, however, the Jacobian Matrix (J) is not directly invertable. Therefore, in an embodiment, an approximation of $J^1$ may be computed using linear algebra techniques. Such an approximation may rely on the pseudo-inverse methodology generally illustrated in equation 19, where A is a regularization value.

$$J^{-1} \approx J^T(JJ^T - \lambda I)^{-1} \quad \text{(eq. 19)}$$

When solving for $J^1$, the controller may use the approximation of J (i.e., $J_{approx}$) calculated from equation 17. Since $J_{approx}$ is only valid at the point where it is computed, $J_{approx}^{-1}$ is also only valid for that same position. As the model catheter moves away from the position, $J_{approx}^{-1}$ may need to be recomputed to remain accurate. It should be recognized that $J_{approx}^{-1}$ may be calculated using various techniques, such as, for example, the singular value decomposition (SVD) technique. Once the matrix $J_{approx}^{-1}$ is calculated for a given catheter position, it may then be used, as shown in equation 20, to convert a desired movement within the model into the necessary actuator input (or distal steering wire movements) required to achieve that desired movement.

$$\dot{\vec{L}} = J_{approx}^{-1}\dot{X}_3 \quad \text{(eq. 20)}$$

Due to the inaccuracies caused by numerical approximations of the Jacobian and inverse Jacobian, in an embodiment where such approximations are used, a computed movement of the catheter may be made in a series of discrete steps, with the Jacobian approximation being recomputed at each discrete interval. In an embodiment where the catheter movement is configured to follow a constructed a trajectory, as generally shown in FIGS. 28*a*-28*b*, the system may divide the trajectory into a series of incremental movements. At each increment, the controller may be configured to re-compute both $J_{approx}^{-1}$ and the incremental heading needed to arrive at the next interval location (such as the movement vector 1830 represented in FIG. 33). These updated values may then be used to compute a series of incremental manipulator inputs or distal steering wire motions that would cause the actual catheter to follow the desired trajectory.

Figure 40A:
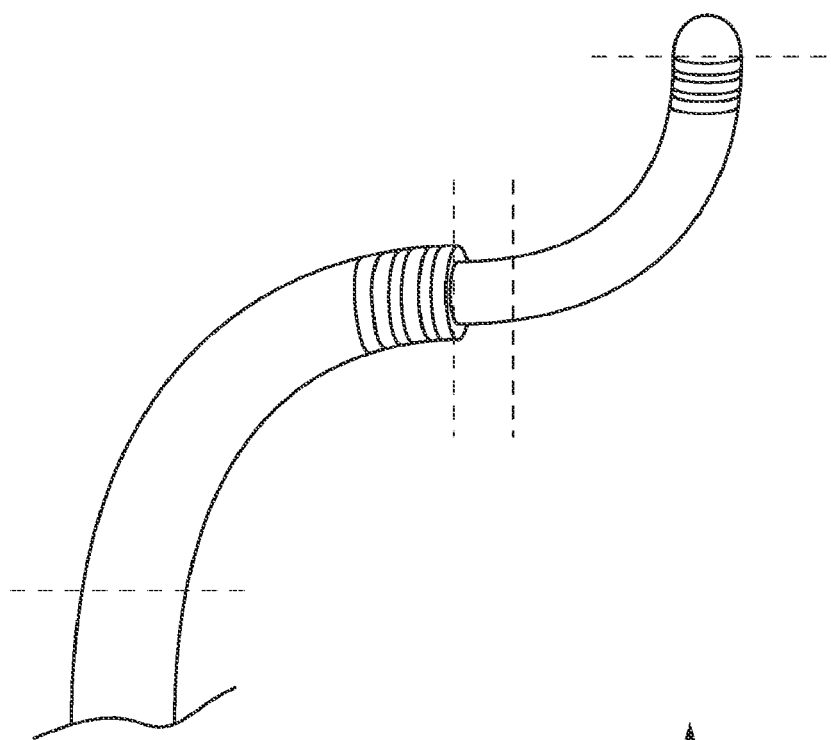
FIG. 40a-40b are illustrations of compound catheter-sheath movement.
Figure 40B:
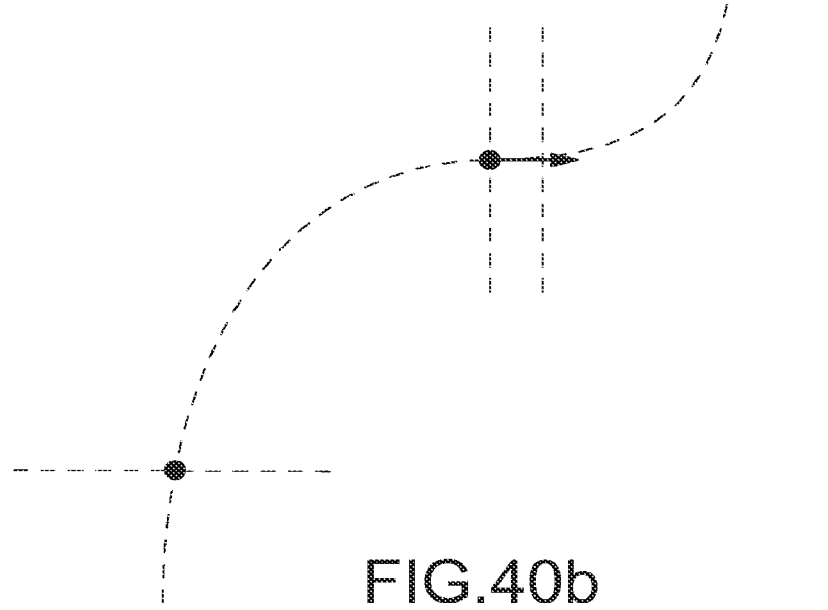

While the above description is made in terms of controlling the position of a point located at or near the pull ring of a catheter, it may likewise be possible to control orientation the catheter at that point. Furthermore, as described above, the system may comprise both an actively controlled catheter and an actively controlled sheath. In such a case, the controller may be configured to account for a greater number of input degrees of freedom, and the model may take into account the compound dynamics of the catheter/sheath combination, as generally shown in FIG. 40*a*-40*b*.

Referring back to FIG. 31, once the desired manipulator inputs or distal steering wire motions are computed (1710), the controller may then instruct the manipulator to move the actuators in accordance with the computed motions (1712). In an embodiment where the controller is configured to compute incremental manipulator actuations $\Delta\vec{\lambda}$, the controller may command each respective actuator to move to a specified absolute location, or may command the respective actuators to move an incremental distance from their current position. In an embodiment that uses linear actuators to manipulate the steering wires, this motion may be achieved by directly monitoring and controlling the current linear position of the actuator in either an absolute or relative sense. In an embodiment where the linear motion is driven by a separate actuator, such as for example, a servomotor driven ball screw, the system may first command the desired motion in terms of a linear position, or a change in a linear position of the actuator (e.g., the finger). Once this position is commanded, a secondary motor controller may receive feedback as to the current position of the actuator from, for example, an absolute or relative linear encoder or a potentiometer, and may then use known control techniques to manipulate the drive-servomotor in a manner that achieves the resultant linear motion.

Figure 41:
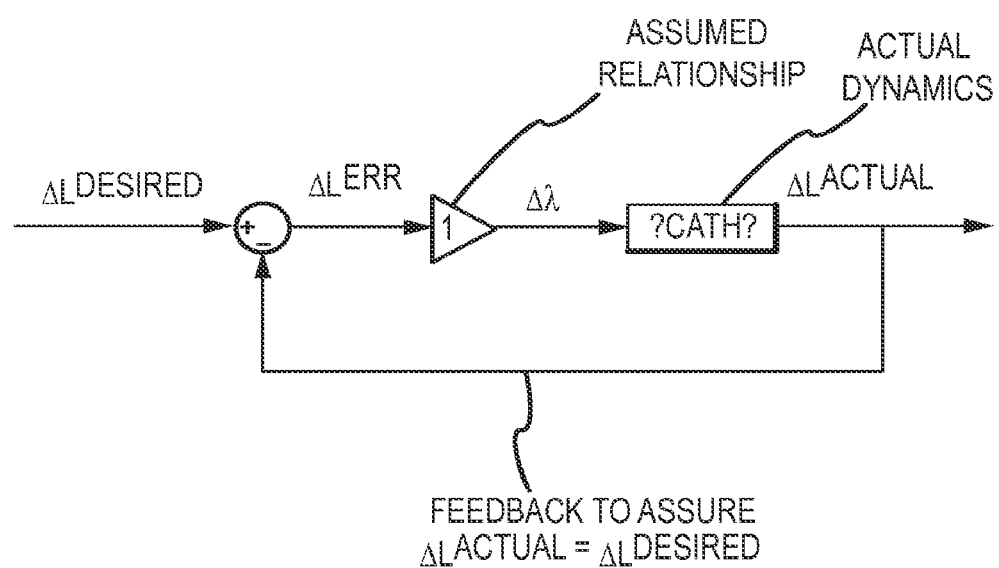
FIG. 41 is an embodiment of a catheter control diagram employing feedback.

In an embodiment where the controller specifies movement commands in terms of distal steering wire lengths (i.e., $\{L_A, L_B, L_C, L_D, L\}$), the controller may be configured to move the proximal actuators (e.g., fingers) while receiving feedback on the actual length change of the distal steering wires, as generally illustrated in FIG. 41. In an embodiment, the controller may initially assume that an incremental manipulator input $\Delta \vec{\lambda}$ directly corresponds to the same motion of the distal steering wire $\Delta \vec{L}$. The controller may then use a distal length measurement system, such as described above, to monitor the actual movement of the distal steering wires for the purpose of reducing any inaccuracies in the assumed relationship between the manipulator inputs and the distal steering wire movement.

Referring back to FIG. 31, after the controller moves the actuators in accordance with the initially computed trajectory, the system may then monitor various parameters of the manipulator and distal catheter. In an embodiment, the real-time position of the catheter, as sensed by the positioning system, may be monitored. This real-time position may be used, for example, to enhance the catheter's ability to accurately track a particular target or path, determine contact with an obstruction, or provide input to or further refine the kinematic model. In an embodiment, the system may monitor parameters generated by the distal portion of the catheter. Such parameters may include indication of physical contact through the use of various force sensors, an indication of electrical coupling through the use of electrical impedance monitoring, or an indication of tissue proximity through, for example, EnSite Contact proximity sensing. In an embodiment, the system may monitor parameters of the manipulator to detect workspace limitations and limitations on the amount of allowable exerted force. Examples of each of these forms of feedback will be described below.

In an embodiment where the real-time position in used to enhance the catheter's ability to track a particular target or path, the monitored position and orientation may be fed back to the controller in a closed-loop manner to account for model inaccuracies, external disturbances, or drift. The controller may be configured such that the system is either critically damped or overdamped and may cause the actual position of the distal catheter tip to rapidly converge to the desired position, though not permit the catheter to overshoot the desired position. Additionally, in an embodiment where the predicted model moves in an open-loop manner, (rather than path-tracking) positional feedback may be employed to dynamically compensate for inaccuracies in the kinematic model by periodically computing a model correction matrix. In an embodiment, the model correction matrix may be applied to the forward kinematic model, and may rotate and/or translate the position of the model catheter to reflect the sensed position/orientation of the actual catheter. This correction matrix may be maintained by the system and continuously adjusted and applied during control/movement iterations.

The catheter's actual position may also be used to infer contact with tissue by comparing the expected position with the actual position. If, during a movement, the system tensions one or more steering wires, as described above, the distal portion of the catheter is expected to bend in a predictable manner. If, during the process of tensioning, the catheter's observed movement does not correspond with the expected movement, it may be inferred that there is an obstruction preventing the expected movement. The system may be configured to likewise analyze the actual movement for changes or discontinuities in other relationships, such as for example, the speed of the movement $$\left(\text{e.g.,} \frac{\partial X}{\partial t}\right),$$

or the rate of movement in view of the actuation inputs $$\left(\text{e.g.,} \frac{\partial X}{\partial \lambda}\right).$$

Figure 42:
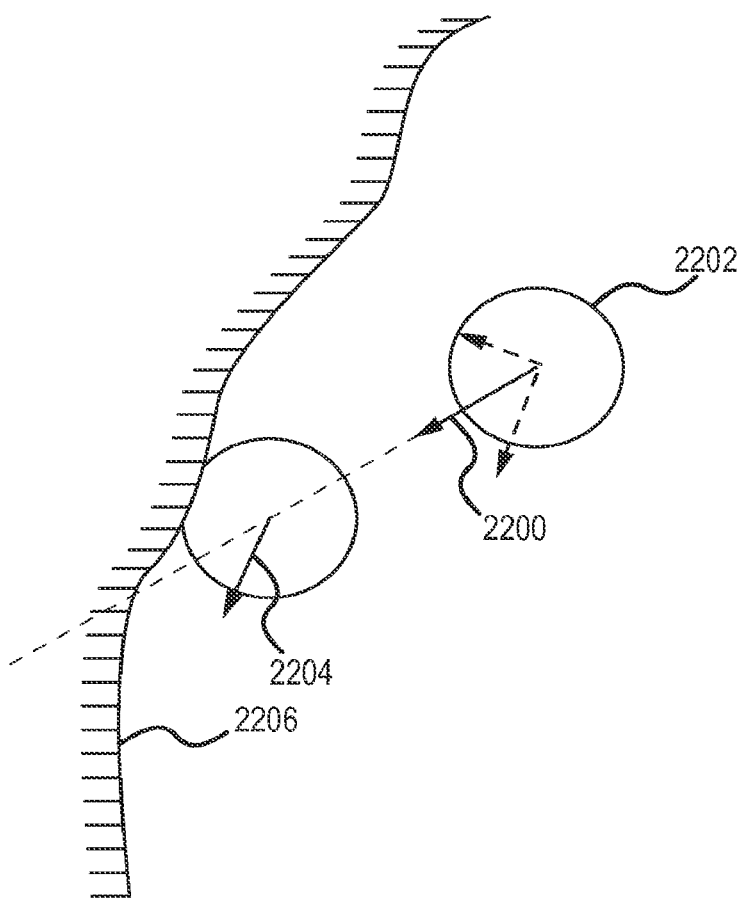
FIG. 42 is an illustration of a catheter movement from which contact may be deduced.

As the rate of movement decreases, potentially approaching zero, it may be inferred that the distal catheter tip has encountered an obstruction. If an obstruction is detected in this manner, the system may be configured to cease further movement or actuation. In an embodiment, the system may be configured to determine the contact direction by analyzing the heading of the catheter movement. If the heading (i.e., movement vector 2200) of the catheter 2202 unexpectedly changes direction (such as to new heading 2204), as shown in FIG. 42, the system may infer that an obstruction is preventing further movement in a direction normal to the surface 2206. In such an example, the component of the movement vector 2204 in a direction normal to the surface may be reduced to zero, while movement parallel to the surface may remain (though may be reduced in magnitude due to contact friction).

In an embodiment where the forward kinematic relationships are constructed through empirical modeling, such as, for example, hysteretic recurrent neural network modeling, the actual positional movement of the catheter in response to the steering wire inputs may be relied on to progressively train the model. Real-time feedback during a procedure may likewise be used to further refine the model if desired. Additionally, in an embodiment where the model is configured to account for past positions or hysteresis, the positional feedback may also be logged and provided to the model as an input.

As described above, the catheter used with the robotic catheter system may incorporate a sensor in the distal tip that is configured to provide an indication of physical contact between the catheter and an obstruction. Such sensors may include load cells, shape memory alloy based force sensors, piezoelectric force sensors, strain gauges, or optical-based or acoustic-based force sensors. If the catheter encounters tissue or another obstruction during operation, the contact or force sensor may be configured to provide an indication to the controller that such contact exists. Similar to contact sensing via position monitoring, if contact is detected, the controller may be configured to refrain from applying further force on the catheter in the direction of the sensed contact. Alternatively, the system may use the indication of the force to provide a controlled amount of force between the catheter and tissue that may be pre-set by the physician.

In an embodiment, the catheter may incorporate an electrode on its distal tip that is configured to provide an indication of the degree of electrical coupling between the catheter and tissue. (described in detail in U.S. patent application Ser. No. 12/622,488, titled "System and Method for Assessing Lesions in Tissue," incorporated by reference in its entirety). Such an indication may be based on a measured impedance and/or phase of a signal transmitted through the tissue, and may allow the system to determine the nature of the electrical coupling that exists. If the catheter is in inadequate electrical contact with the tissue, the system may, for example, alert the user, or automatically refine the position until an adequate measure of electrical coupling exists.

Figure 43:
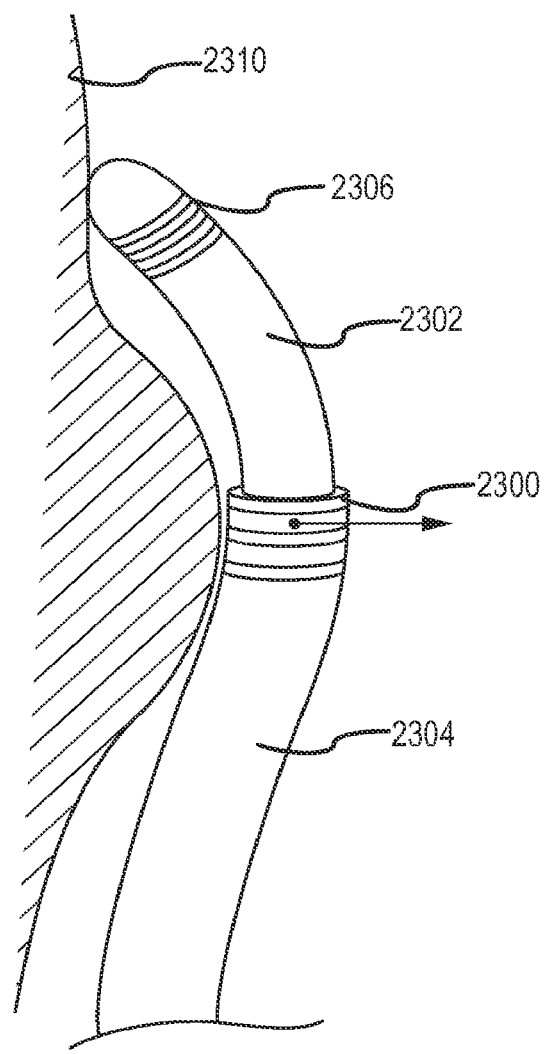
FIG. 43 is an illustration of a compound catheter-sheath movement for avoiding proximal obstructions.

As illustrated in FIG. 43, the catheter 2302 and/or sheath 2304 may further include one or more electrodes 2306, 2308 positioned along a length of the respective catheter and/or sheath to determine the proximity of tissue 2310 from the catheter/sheath body. In an embodiment, each electrode may monitor the impedance and/or phase of a signal transmitted through the tissue, provide it to the controller to compute an electrical coupling index (as described in the above referenced Ser. No. 12/622,488). The controller may use the computed coupling index to determine the relative distance between the catheter/sheath body and the tissue 2310 transmitting the signal. By knowing the location of the catheter/sheath with respect to the detected anatomy, the controller my be able to adjust the behavior of the catheter to favor either increased precision (e.g., when the catheter is immediately proximate to the tissue) or increased speed (e.g., when the catheter is away from the tissue). In an embodiment, the system may be configured to adjust the pose of the catheter/sheath to avoid contacting the tissue with the device body. As generally illustrated in FIG. 43, if proximity is detected between the body of the device and tissue, the device may be configured to translate the distal portion of the sheath near where the protruding obstruction is located. Once in position, the sheath may be caused to bend away from the protrusion, while the catheter is then bent back toward the tissue.

Other forms of feedback that may be available to the controller include feedback from the manipulator about the status of each actuator within the given workspace. As described above, each steering wire actuator and carriage may have a finite range of travel. As each is manipulated, it may draw closer to the limits on its range of travel. Therefore, the manipulator may be able to convey each actuator's current position with respect to the actuator's total range of motion. If an actuator nears or reaches a limit of its individual workspace or range of motion, the controller may be configured to prevent further attempted actuation and may alert the physician so that appropriate action may be taken. The manipulator may be configured to understand the full range of each actuator motion through, for example, the use of linear encoders coupled with each actuator, or the use of sensors, such as hall effect sensors, at or near the limits of the available travel. In an embodiment, the limits may be hard coded as an absolute encoder count, or may be detected through an initialization routine prior to use.

In another embodiment, the manipulator may be configured to monitor the force exerted by each actuator. This indication of force may convey to the controller that the catheter or sheath have encountered an obstruction if the force becomes too great. Alternatively if the force applied on an actuator is lower than an acceptable range, it may signify a loss of contact between, for example, the actuator finger and the slider block. It may also signify that, for example, a steering wire's integrity has been compromised in some manner. One example of this may be a break in the coupling between the steering wire and the pull ring.

The robotic catheter system may be a useful tool in increasing the speed, precision, repeatability, and effectiveness of a particular procedure. It may allow the physician to control the catheter motion in intuitive ways that enable dynamic path planning and may allow for certain automated motions or procedures. It is necessary that during any automated movement, the actual catheter must traverse a given space without unintentionally contacting or attempting to pass through tissue. Therefore, the system may be configured to use a knowledge of the anatomical model geometry, a knowledge of the catheter dynamics, and/or available real-time feedback from the actual catheter to circumnavigate any obstacles or anatomical features. Additionally, while it is important to prevent the robotic catheter tip from unintentionally passing through tissue, contact between the tissue and a proximal portion of the catheter or sheath may serve to prevent the distal tip from reaching certain locations. In such a case, the catheter may be configured to account for proximal contact between the catheter or sheath and a particular anatomical feature.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

The invention claimed is:

1. A method of determining the path of a robotically manipulated catheter within an anatomical model, the method comprising:
   selecting a plurality of target points within the anatomical model;
   determining a minimum transverse distance between each of the plurality of points and an anatomical surface in the anatomical model, wherein the minimum transverse distance automatically circumnavigates an anatomical feature in the anatomical model;
   defining allowable catheter movement speeds as a function of the minimum transverse distance;
   registering the current position of a robotically manipulated catheter within the anatomical model; and specifying a destination point for the robotically manipulated catheter, wherein the destination point comprises one of the plurality of target points moving the robotically manipulated catheter to the destination point, wherein the robotically manipulated catheter is moved to the destination point within the allowable catheter movement speeds.

2. The method according to claim 1, further comprising computing a projected travel time based on the current catheter position, the destination point, and the allowable catheter speed function.

3. The method according to claim 2, further comprising determining a preferred trajectory for the catheter to minimize total travel time.

4. The method according to claim 1, wherein moving the robotically manipulated catheter comprises using optimized path planning routines and a closed-loop positioning control.

5. The method according to claim 1, further comprising performing a treatment after the robotically manipulated catheter is moved to the destination point.

6. The method according to claim 5, further comprising pulling the robotically manipulated catheter across a surface of the anatomical model while performing the treatment.

7. The method according to claim 1, wherein the destination point comprises a location on a surface of the anatomical model.

8. The method according to claim 7, further comprising moving the robotically manipulated catheter to the destination point, and wherein the robotically manipulated catheter makes contact with the surface of the anatomical model at an oblique angle.

9. The method according to claim 1, wherein the destination point comprises a location a fixed distance from a surface of the anatomical model.

10. The method according to claim 1, further comprising a user selecting the plurality of target points.

11. The method according to claim 10, wherein the plurality of target points are selected using a multi-touch interface.

12. A method of automatically moving a robotically manipulated catheter within an anatomical model, the method comprising:
    determining at least one target location;
    determining a minimum transverse distance between a starting location and the at least one target location, wherein the minimum transverse distance automatically circumnavigates an anatomical feature in the anatomical model;
    determining a minimum distance between the starting location and an anatomical surface of the anatomical model;
    defining allowable catheter movement speeds as a function of the minimum distance;
    registering the current position of a robotically manipulated catheter within the anatomical model; and
    determining a preferred trajectory for the catheter between the starting location and the at least one target location to minimize total travel time
    moving the robotically manipulated catheter to the at least one target location, wherein the robotically manipulated catheter is moved to the at least one target location within the allowable catheter movement speeds.

13. The method according to claim 12, wherein the preferred trajectory is determined based on a projected travel time of the robotically manipulated catheter.

14. The method according to claim 12, further comprising performing a treatment after the robotically manipulated catheter is moved to a final location of the at least one target location.

15. The method according to claim 12, wherein the at least one target location comprises at least one location on a surface of the anatomical model.

16. A method of automatically moving a robotically manipulated catheter within an anatomical model, the method comprising:
    determining a target location;
    determining a minimum transverse distance between a starting location and the target location, wherein the minimum transverse distance automatically circumnavigates an anatomical feature in the anatomical model;
    determining a minimum distance between the starting location and an anatomical surface of the anatomical model;
    defining an allowable catheter movement speed as a function of the minimum distance;
    registering the current position of a robotically manipulated catheter within the anatomical model;
    computing a projected travel time based on the starting location, the target location, and the allowable catheter movement speed; and
    determining a preferred trajectory for the catheter between the starting location and the at least one target location
    moving the robotically manipulated catheter to the target location.

17. The method according to claim 16, further comprising performing a treatment after the robotically manipulated catheter is moved to the target location.

* * * * *